United States Patent
Tian et al.

(10) Patent No.: US 11,008,286 B2
(45) Date of Patent: May 18, 2021

(54) AMINO MERCAPTAN COMPOUND AND PREPARATION METHOD THEREFOR AND USE THEREOF IN PROTECTION AGAINST RADIATION

(71) Applicant: Institute of Radiation Medicine Chinese Academy of Medical Sciences, Tianjin (CN)

(72) Inventors: Hongqi Tian, Tianjin (CN); Ying Cheng, Tianjin (CN); Qianru Zhang, Tianjin (CN); Zhimei Zhu, Tianjin (CN); Yueying Wang, Tianjin (CN)

(73) Assignee: SHANGHAI KECHOW PHARMA, INC, Shanghai (CN)

( * ) Notice: Subject to any disclaimer, the term of this patent is extended or adjusted under 35 U.S.C. 154(b) by 0 days.

(21) Appl. No.: 16/330,474

(22) PCT Filed: Sep. 1, 2017

(86) PCT No.: PCT/CN2017/100158
§ 371 (c)(1),
(2) Date: Mar. 5, 2019

(87) PCT Pub. No.: WO2018/041245
PCT Pub. Date: Mar. 8, 2018

(65) Prior Publication Data
US 2019/0202779 A1   Jul. 4, 2019

(30) Foreign Application Priority Data

Sep. 5, 2016 (CN) .......................... 201610802313.8

(51) Int. Cl.
| | |
|---|---|
| *C07C 323/44* | (2006.01) |
| *C07C 321/04* | (2006.01) |
| *C07C 319/12* | (2006.01) |
| *C07C 319/06* | (2006.01) |
| *C07C 323/25* | (2006.01) |
| *A61P 39/02* | (2006.01) |
| *A61P 35/00* | (2006.01) |
| *A61K 31/16* | (2006.01) |

(52) U.S. Cl.
CPC ............ *C07C 323/44* (2013.01); *A61K 31/16* (2013.01); *A61P 35/00* (2018.01); *A61P 39/02* (2018.01); *C07C 319/06* (2013.01); *C07C 319/12* (2013.01); *C07C 321/04* (2013.01); *C07C 323/25* (2013.01)

(58) Field of Classification Search
CPC ... C07C 323/44; C07C 323/25; C07C 321/04; C07C 319/06; A61P 39/02
See application file for complete search history.

(56) References Cited

U.S. PATENT DOCUMENTS

| | | | | |
|---|---|---|---|---|
| 5,877,212 A | * | 3/1999 | Yu .......................... | A61K 8/365 514/178 |
| 2002/0045653 A1 | | 4/2002 | Shih et al. | |
| 2004/0018983 A1 | * | 1/2004 | Rice ...................... | A61K 31/00 514/3.5 |
| 2004/0229815 A1 | | 11/2004 | Nagasawa et al. | |
| 2006/0013784 A1 | | 1/2006 | Philippe et al. | |
| 2006/0287398 A1 | | 12/2006 | Higuchi et al. | |
| 2013/0316942 A1 | | 11/2013 | Mograbi et al. | |
| 2014/0193340 A1 | | 7/2014 | Miller | |
| 2016/0101150 A1 | * | 4/2016 | Jaynes ................... | A61K 38/10 514/3.8 |

FOREIGN PATENT DOCUMENTS

| | | |
|---|---|---|
| CN | 1423528 A | 6/2003 |
| CN | 1679488 A | 10/2005 |
| CN | 1921876 A | 2/2007 |
| CN | 103415532 A | 11/2013 |

(Continued)

OTHER PUBLICATIONS

Atkinson et al, Journal of Medicinal Chemistry, Potential Antiradiation Drugs. I. Amide, Hydroxamic Acid, and Hydrazine Derivatives of Mercapto Acids. Amino Thioacids, 1965, pp. 29-32. (Year: 1965).*

PCT International Search Report and Written Opinion dated Nov. 29, 2017 in corresponding Application No. PCT/CN2017/100158 with unofficial English translation, 15 pages.

"STN Registry", STN on the web, Jun. 14, 2015 RN: 1779639-66-5, 1779601-62-5, 1779600-46-2, non-official translation ("STN Regisry Database Search Record").

(Continued)

*Primary Examiner* — Paul A Zucker
(74) *Attorney, Agent, or Firm* — Dilworth IP, LLC

(57) ABSTRACT

The present invention discloses an amino mercaptan compound, preparation method thereof and use thereof in radiation protection. The compound has the structure of formula I, wherein $A_1$, $A_2$, $R^1$, $R^2$, $R^5$, $R^6$, and $R^3$ and $R^4$ are defined herein. The compound has the effects of reducing the biological damage caused by ionizing radiation, extending the survival period and survival rate of the radiated animals, and significantly alleviating the side effects of radiotherapy, and has a low toxicity. The present invention opens up a new way for protection and treatment of ionizing radiation damage.

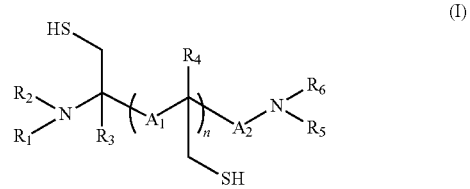

(I)

11 Claims, 8 Drawing Sheets

(56) References Cited

FOREIGN PATENT DOCUMENTS

| CN | 103772245 A | 5/2014 |
| CN | 106432014 A | 2/2017 |
| JP | 04321674 A | 11/1992 |

OTHER PUBLICATIONS

"STN Columbus", InfoChem, Jul. 31, 2017 RN: 2105952-7, 6 pages.
N. Haruki, et al.: Syntheses of Aminothiol Derivatives, Journal of Pharmaceutical Society of Japan, vol. 84, No. 10, Oct. 1964, pp. 944-955.
J. R. Piper, et al.: S-2,.omega.-Diaminoalkyl dihydrogen phosphorothioates as antiradiation agents, Journal of Medicinal Chemistry, vol. 22, No. 6, Jun. 1, 1979 (Jun. 1, 1979), pp. 631-639.
Extended European Search Report, European Application No. 17845547.3, dated May 26, 2020, 10 pages.

* cited by examiner

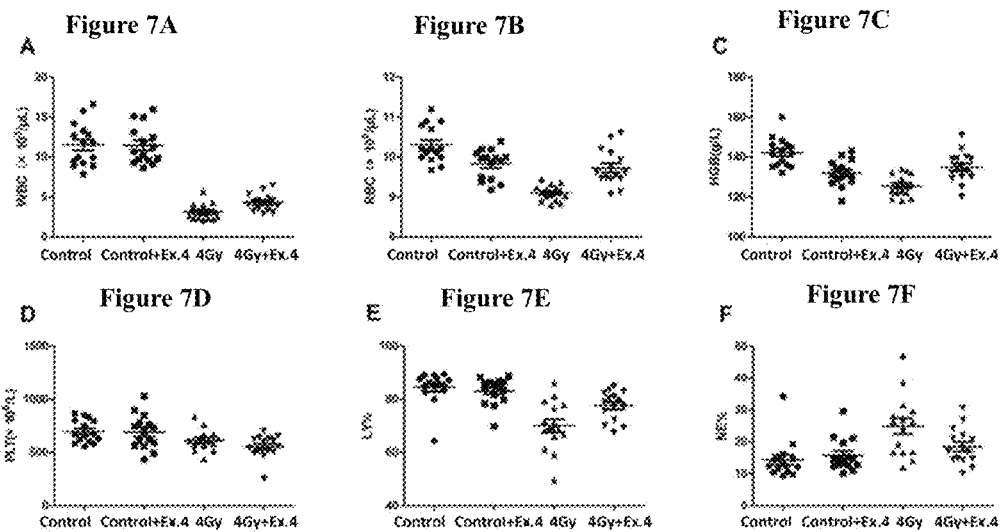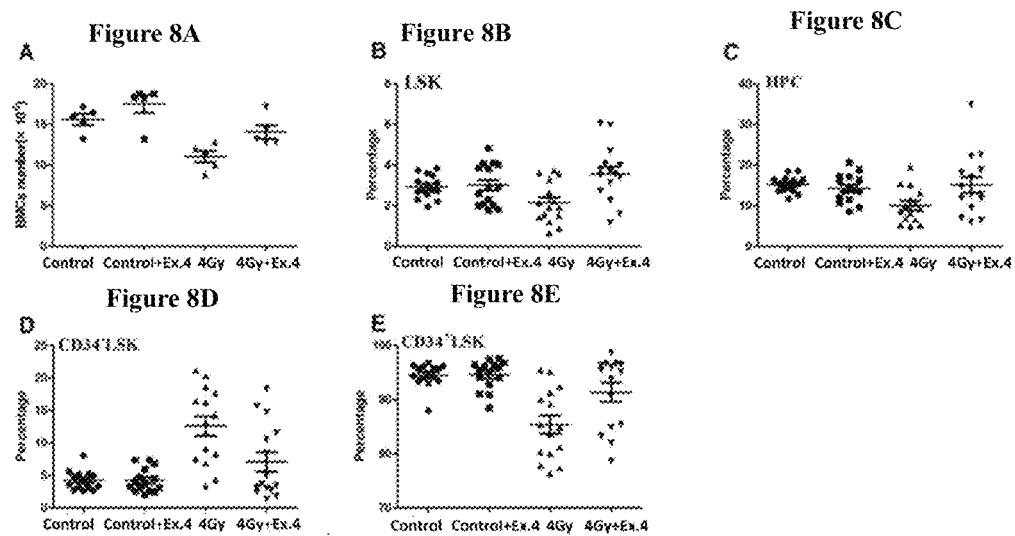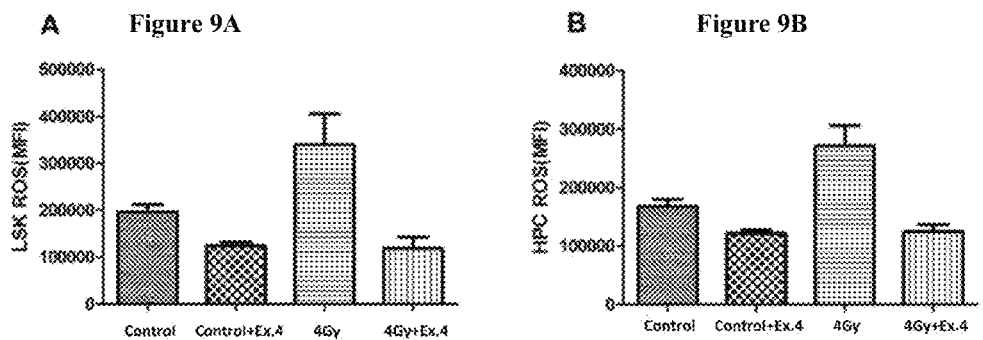

AMINO MERCAPTAN COMPOUND AND PREPARATION METHOD THEREFOR AND USE THEREOF IN PROTECTION AGAINST RADIATION

TECHNICAL FIELD

The present invention relates to the field of medicine, in particular to the protection against ionizing radiation damage, in particular to a new class of compounds having the effect of radiation protection. The present invention also relates to a method for preparing the compound. The present invention also relates to the use of the compound in the prevention and treatment of damages and diseases caused by ionizing radiation.

BACKGROUND ART

With the vigorous development of the global nuclear cause, the nuclear technology has been widely used in various fields such as nuclear power plants, aerospace, national defense and biomedicine, and the chance of human exposure to ionizing radiation and thus causing damage has increased. In the meantime, with the nuclear war and hidden nuclear terror incident worries brought about by the world's tense nuclear security situation, the protection and treatment of body damage caused by ionizing radiation (referred to as radiation damage) is receiving more and more attention.

On the other hand, the incidence of malignant tumors and the number of patients has been increasing in recent years. Radiation therapy plays an indispensable role as one of the main treatments. However, high-dose radiation exposure inevitably leads to acute radiation damage to normal tissues and organs surrounding the tumor and even to the whole body. The side effects of radiation damage seriously restrict the wide application of radiotherapy in tumor therapy, and also significantly affect the efficacy and quality of life of cancer patients after radiotherapy.

At present, there are mainly related drugs for radiation damage treatment: sulfur compounds, hormones, cytokines and Chinese herbal medicines, which have their own inherent defects. For example, sulfur compounds are generally associated with greater side effects, such as amifostine, a representative of such compounds, is currently recognized as the best protective compound and is the first selective broad-spectrum cytoprotective agent approved by the international regulatory agencies, but the extremely short half-life (7 min) and high price (the domestic medical market price is 400-500 yuan per dose) limit its application. The prevention and treatment of radiation damage by hormone drugs are mainly for the nucleated cells, hematopoietic stem cells and progenitor cells in bone marrow, and the effects of such drugs on the sexual and reproductive systems limit their widespread use. Cytokine drugs such as interleukins and colony stimulating factor drugs can alleviate and treat radiation-induced bone marrow hematopoietic system damage, but their radiation protection effect is closely related to the time of administration (in the medical practice for prevention and treatment, such drugs require a high level of medical testing and attention), with obvious inflammatory effect, and it is expensive and difficult to store at room temperature. The anti-radiation components of Chinese herbal medicines mainly comprise phenols, polysaccharides and natural flavones, which have the characteristics of unclear active ingredients and low toxicity, and after years of research, there are no similar drugs on the market or to be marketed.

SUMMARY OF THE INVENTION

One purpose of the present invention is to provide a new class of compounds with radiation protection. It has the effects of prolonging the survival period and reducing the death rate of animals after sublethal dose irradiation. It can be used alone as a radiation damage protection and treatment drug, or in combination with radiotherapy, which can alleviate and prevent the adverse reactions caused by radiotherapy.

Another purpose of the present invention is to provide a method for preparing the compound.

The further purpose of the present invention is to provide the use of the compound in the preparation of drugs for the prevention and/or treatment of damages and diseases related to ionizing radiation.

According to an aspect of the present invention, a compound having the following chemical structural formula is provided

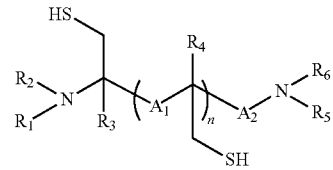

(I)

wherein $A_1$ is selected from: —C(O)NR$^8$—, —S(O)$_2$—NR$^8$—, —S(O)NR$^8$—, and —R$^7$—NR$^8$—;

$A_2$ is selected from: carbonyl, sulfonyl, sulfinyl, substituted or unsubstituted $C_{1-6}$ alkyl;

$R^1$, $R^2$, $R^5$, and $R^6$ may be the same or different and are selected from: hydrogen, substituted or unsubstituted $C_1$-$C_5$ alkyl or heteroalkyl;

n is an integer from 0 to 20,000;

$R^3$ and $R^4$ are independently selected from: hydrogen, X, substituted or unsubstituted $C_1$-$C_6$ alkyl; X is selected from: F, Cl, Br and I;

$R^7$ is selected from: substituted or unsubstituted $C_1$-$C_6$ alkyl; $R^8$ is selected from: hydrogen, substituted or unsubstituted $C_1$-$C_6$ alkyl;

and stereoisomers thereof or pharmaceutically acceptable salts, prodrugs and solvates thereof.

Preferably, the above compound of formula I does not comprise (R)-2-amino-N—((R)-1-amino-3-mercapto-1-oxopropan-2-yl)-3-mercaptopropionamide.

Preferably, $A_1$ is selected from: —C(O)NR$^8$—, and —R$^7$—NR$^8$—; more preferably, $A_1$ is selected from: —C(O)NR$^8$—, and —CH$_2$—NR$^8$—;

preferably, $A_2$ is selected from: carbonyl, sulfonyl, sulfinyl, and substituted or unsubstituted $C_{1-3}$ alkyl; more preferably, $A_2$ is selected from: carbonyl, sulfonyl, sulfinyl, and methylene; further preferably, $A_2$ is selected from: carbonyl, and methylene;

preferably, $R^1$, $R^2$, $R^5$, and $R^6$ may be the same or different and are selected from: hydrogen, $C_{1-3}$ alkyl, and hydroxy or amino substituted $C_1$-$C_3$ alkyl or heteroalkyl; more preferably, $R^1$, $R^2$, $R^5$, and $R^6$ may be the same or different and are selected from: hydrogen, methyl, and ethyl; more preferably, one of $R^1$ and $R^2$ is hydrogen, and the other is $C_1$-$C_3$ alkyl (e.g., methyl, ethyl or propyl), as well as one of $R^5$ and $R^6$ is hydrogen, and the other is $C_1$-$C_3$ alkyl (e.g., methyl, ethyl or propyl); even more preferably, one of W and $R^2$ is hydrogen, and the other is methyl, as well as one of $R^5$ and $R^6$ is hydrogen, and the other is methyl; or alternatively, W and $R^2$ are methyl or ethyl, as well as $R^5$ and $R^6$ are methyl or ethyl;

preferably, n is an integer from 0 to 2,000; more preferably, n is an integer from 1 to 200; further preferably, n is an integer from 1 to 200; still further preferably, n is an integer from 1 to 50; more preferably an integer from 1 to 10 (including 1, 2, 3, 4, 5, 6, 7, 8, 9 and 10);

preferably, $R^3$ and $R^4$ are independently selected from: hydrogen, X, substituted or unsubstituted $C_{1-3}$ alkyl; more preferably, $R^3$ and $R^4$ are independently selected from: hydrogen, X, and methyl;

preferably, X is selected from F and Cl; more preferably, X is F;

preferably, $R^7$ is selected from: substituted or unsubstituted $C_1$-$C_3$ alkyl; more preferably, $R^7$ is methylene;

preferably, $R^8$ is selected from: hydrogen, substituted or unsubstituted $C_1$-$C_3$ alkyl; more preferably, $R^8$ is selected from: hydrogen, methyl, and ethyl; further preferably, $R^8$ is hydrogen;

in the compound, the chiral carbon directly attached to $R^3$ and $R^4$ is in the R configuration or the S configuration. Preferably, the chiral carbon directly attached to $R^3$ and $R^4$ is in the R configuration.

More preferably, the chiral carbon directly attached to $R^3$ and $R^4$ is in the R configuration; one of $R^1$ and $R^2$ is hydrogen, and the other is methyl, as well as one of $R^5$ and $R^6$ is hydrogen, and the other is methyl.

In a preferred embodiment of the present invention, the compound has the following general formula

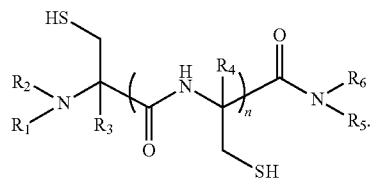

(II)

In another preferred embodiment of the present invention, the compound has the following general formulas

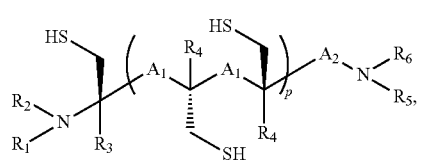

(III)

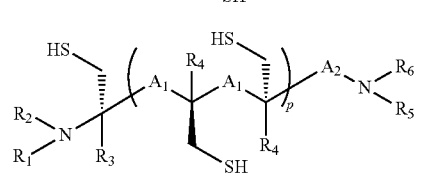

(IV)

wherein p is an integer of from 1 to 10,000, preferably an integer of from 1 to 1,000, more preferably an integer of from 1 to 100, further preferably an integer of from 1 to 10; more preferably an integer of from 1 to 5 (including 1, 2, 3, 4 and 5);

in a preferred embodiment of the present invention, the $R^1$, $R^2$, $R^5$, $R^6$, and $R^8$ are all hydrogen;

In another preferred embodiment of the present invention, $R^1$ and $R^5$ are hydrogen, and $R^2$ and $R^6$ are selected from: methyl and ethyl; in a preferred embodiment of the present invention, the above compounds may preferably be the following compounds, but are not limited to the following compounds:

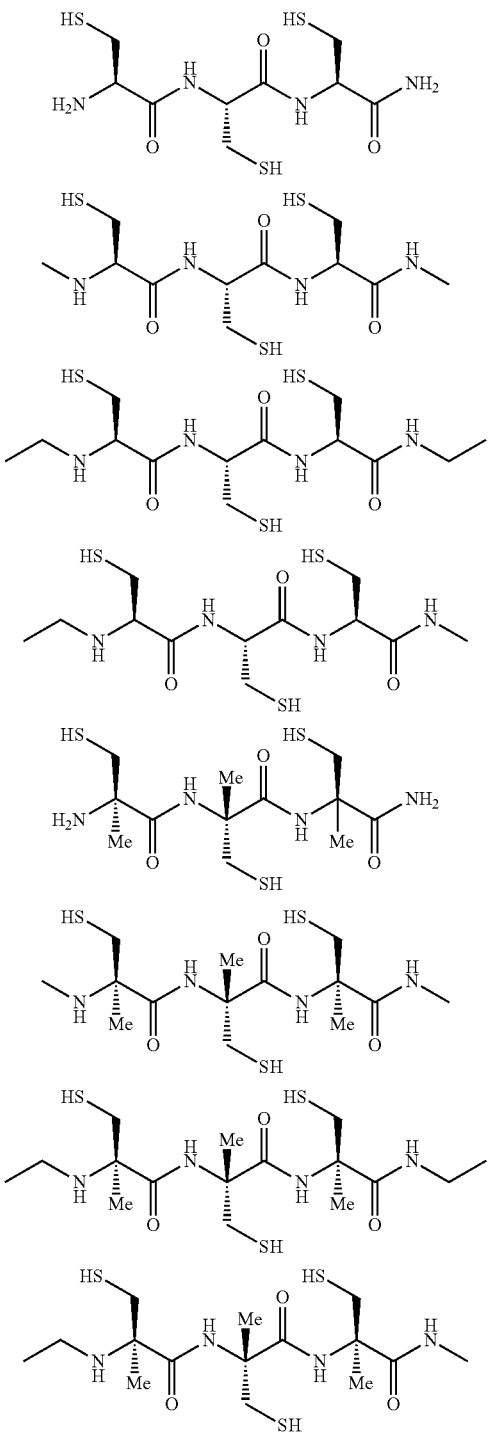

5
-continued
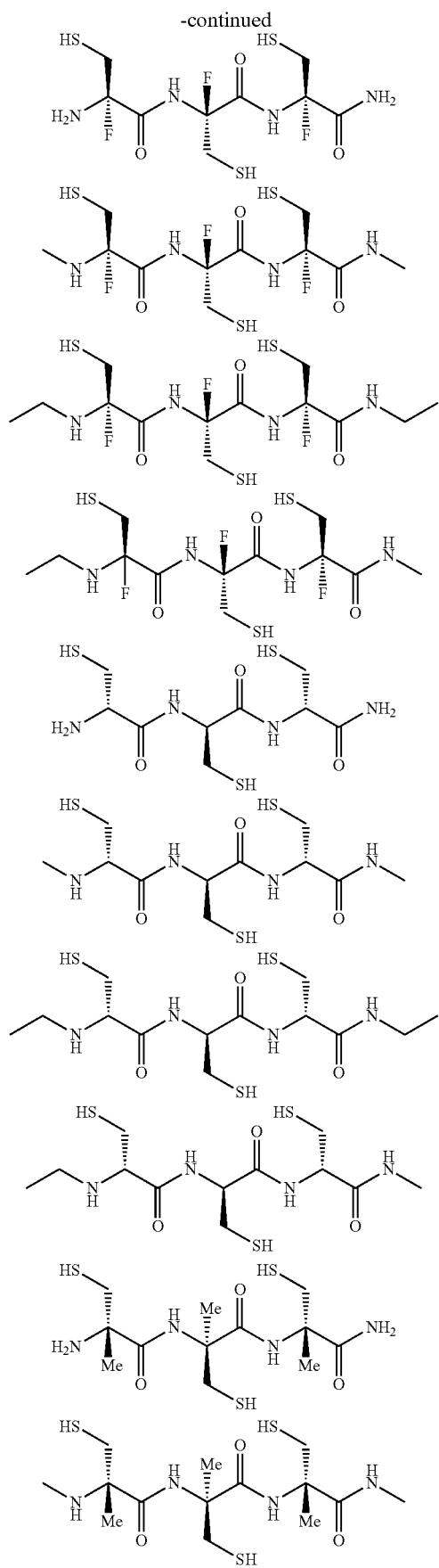
6
-continued
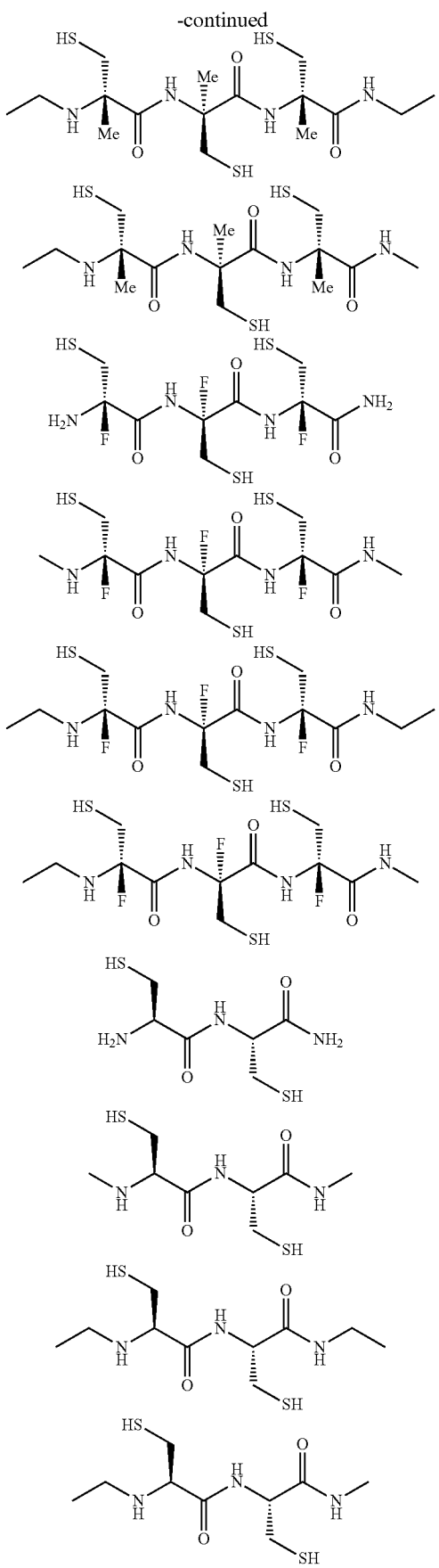

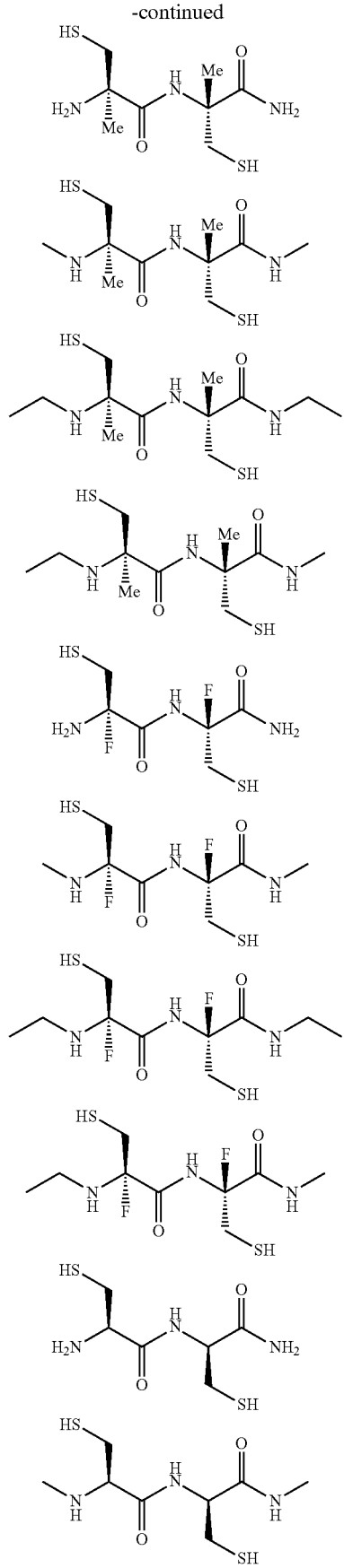

-continued
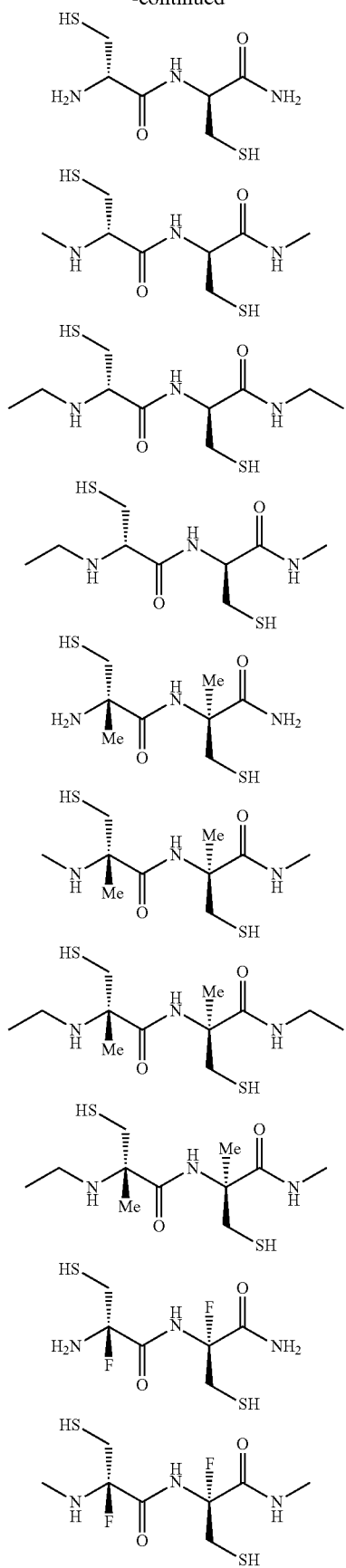
-continued
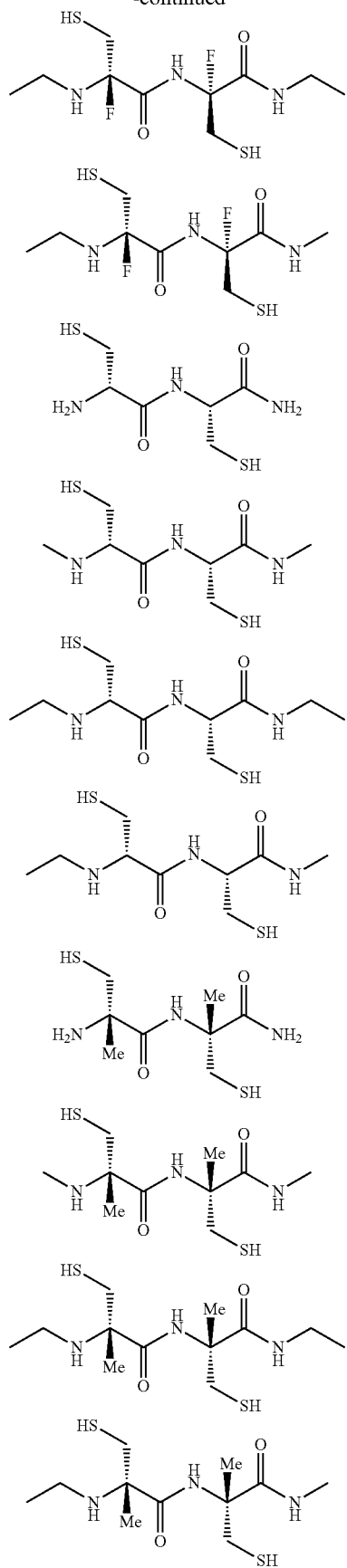

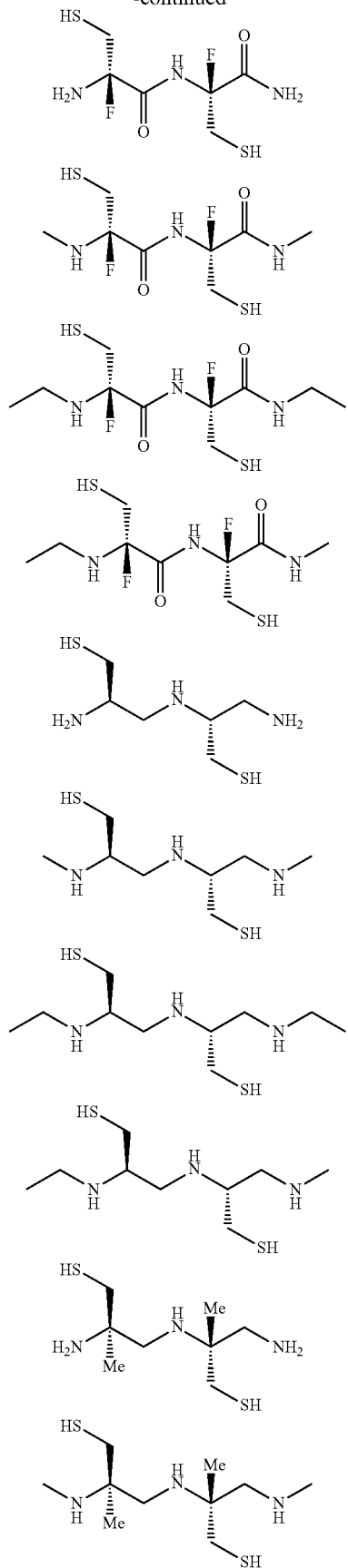
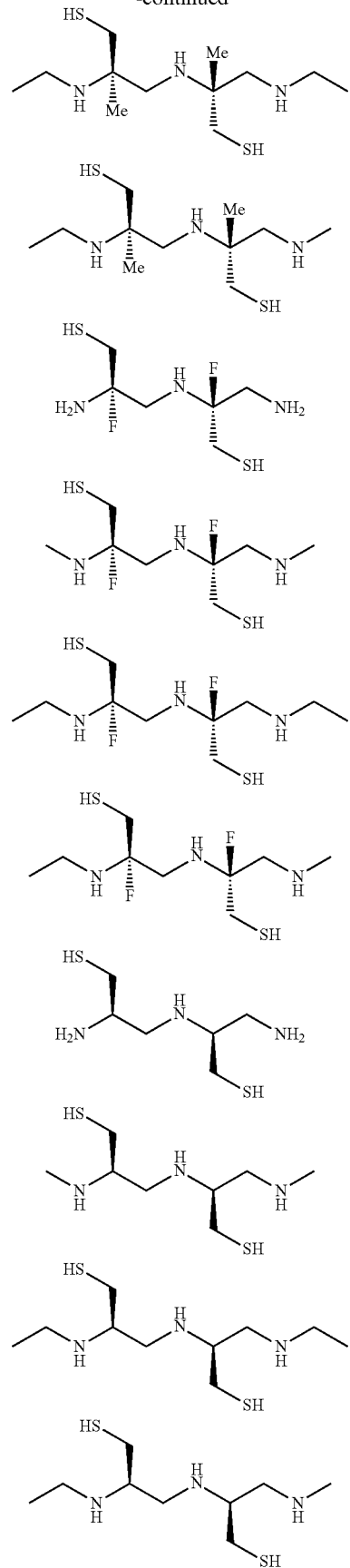

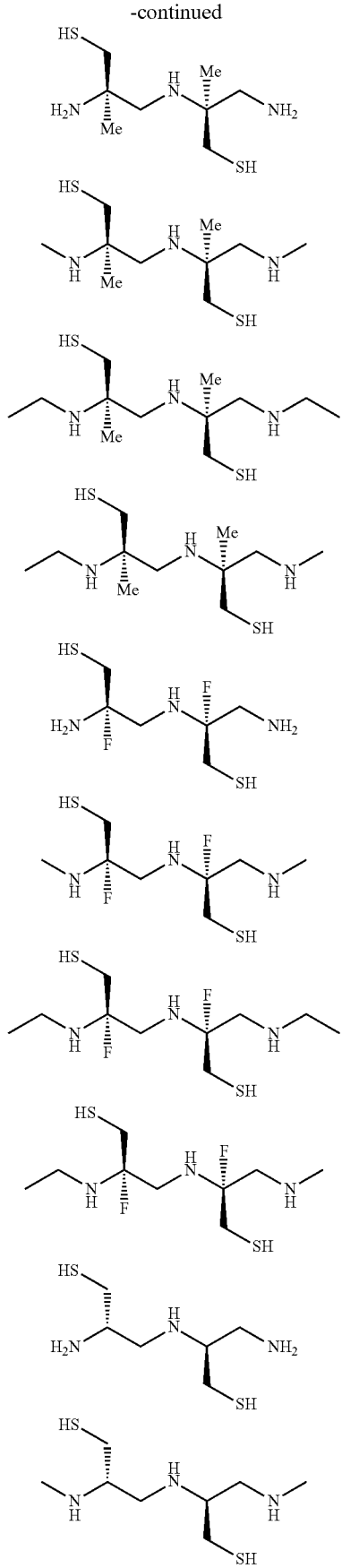
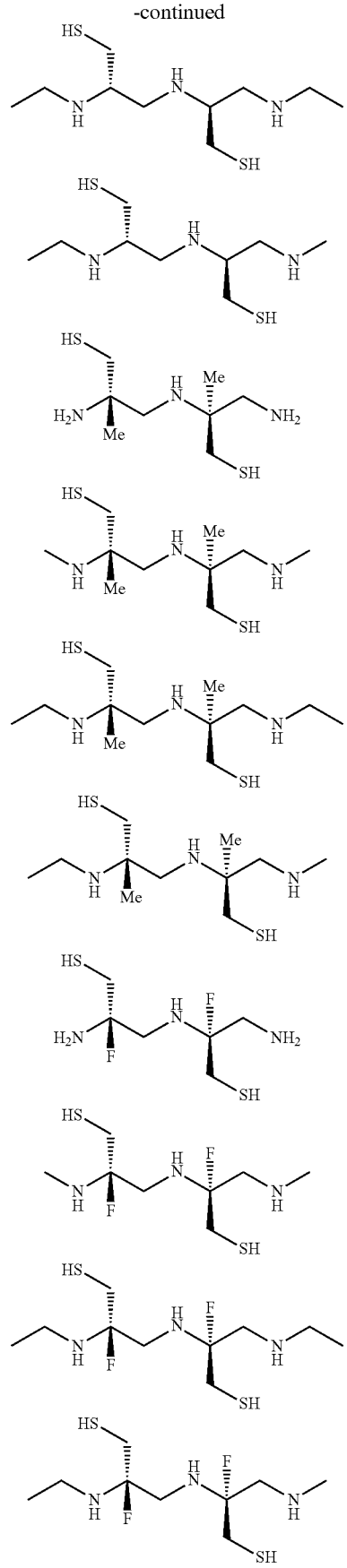

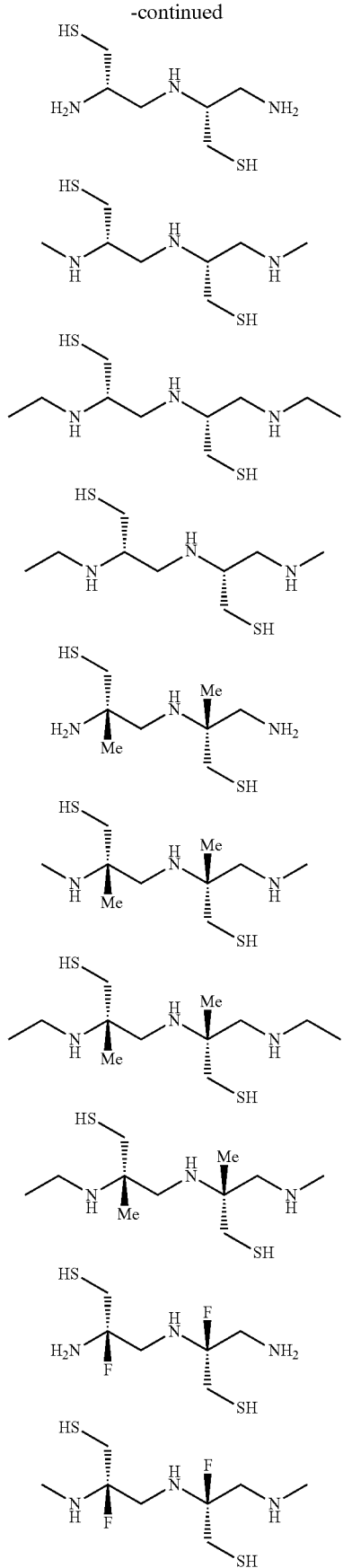
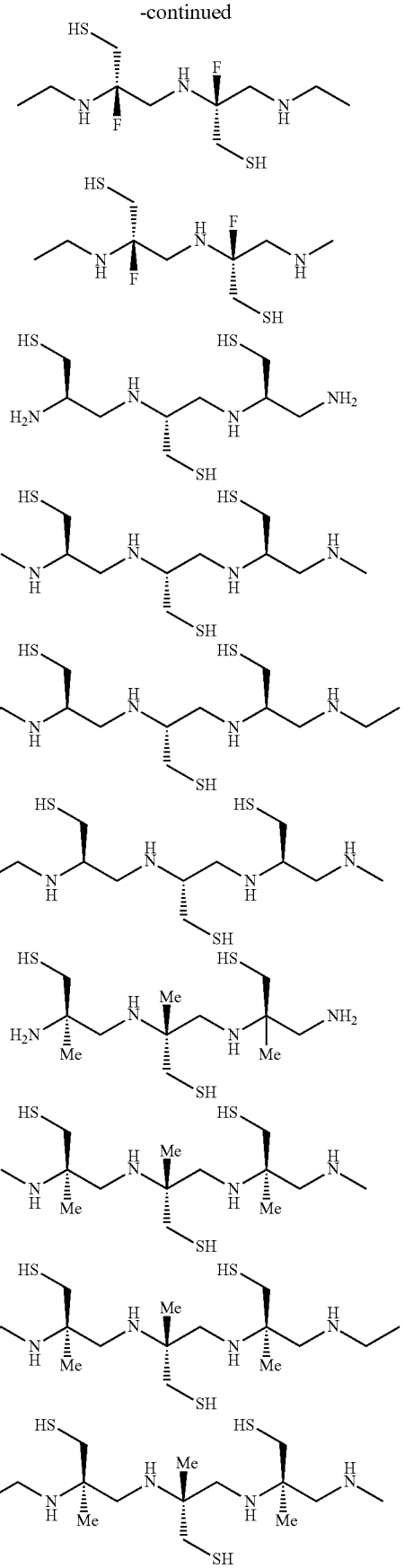

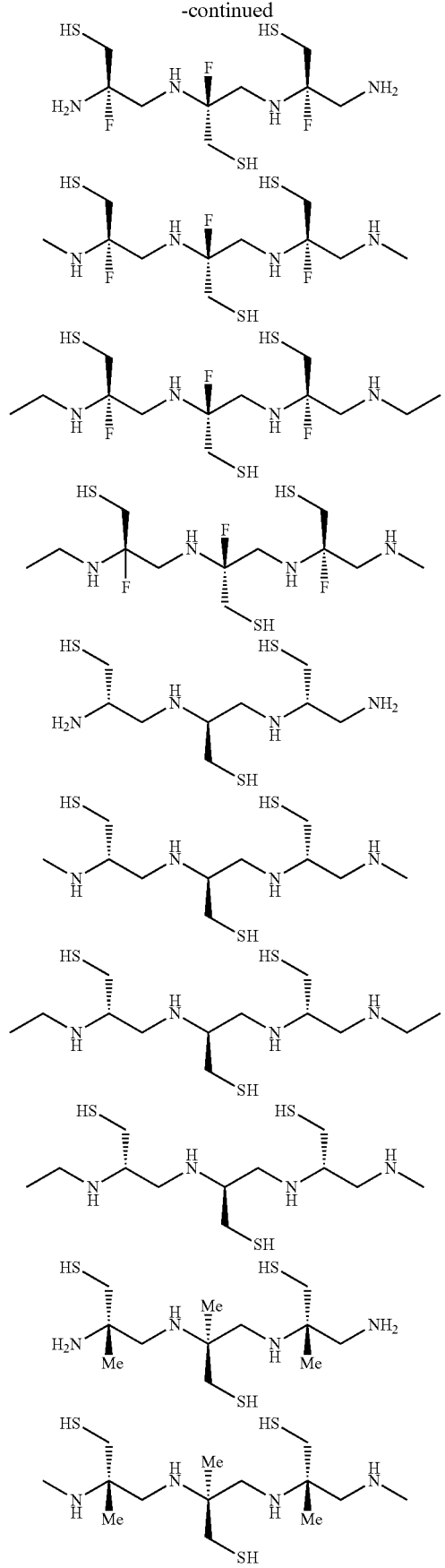
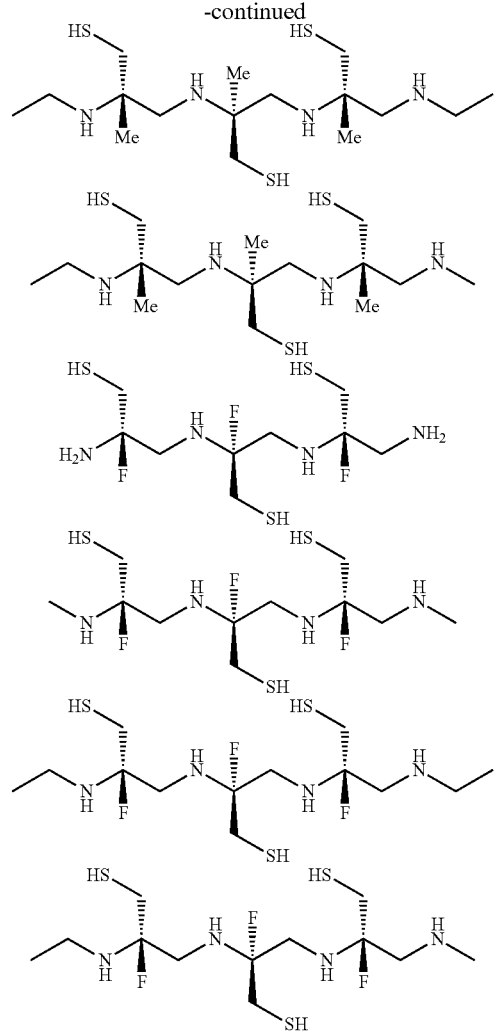
In a preferred embodiment of the present invention, the above compounds may preferably be the following compounds, but are not limited to the following compounds
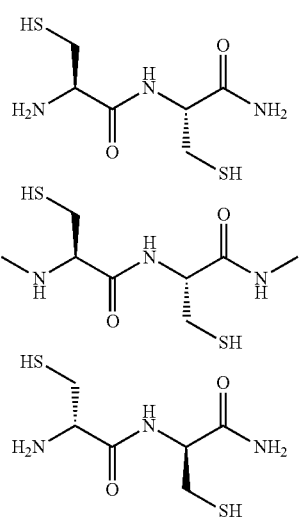

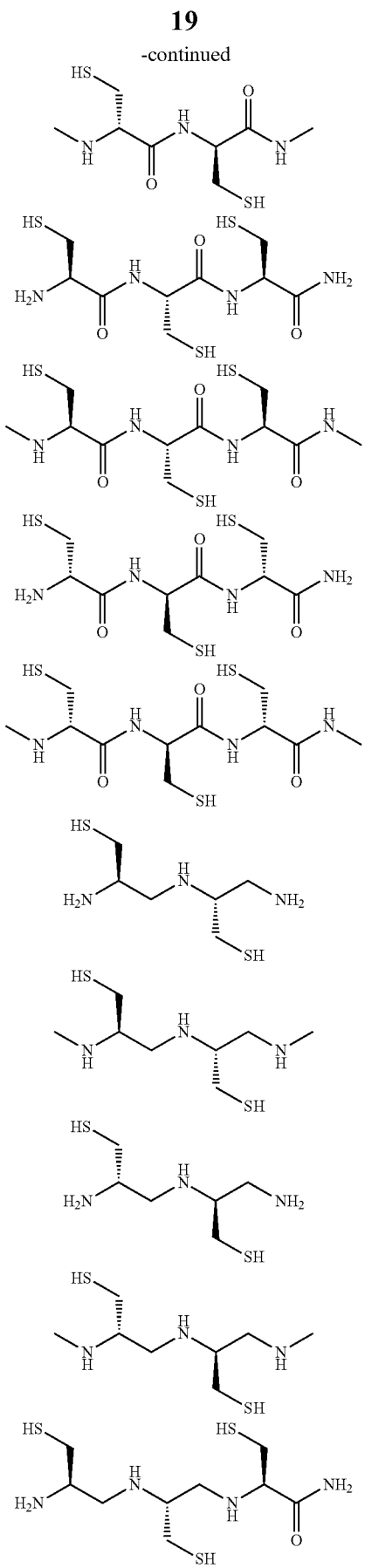
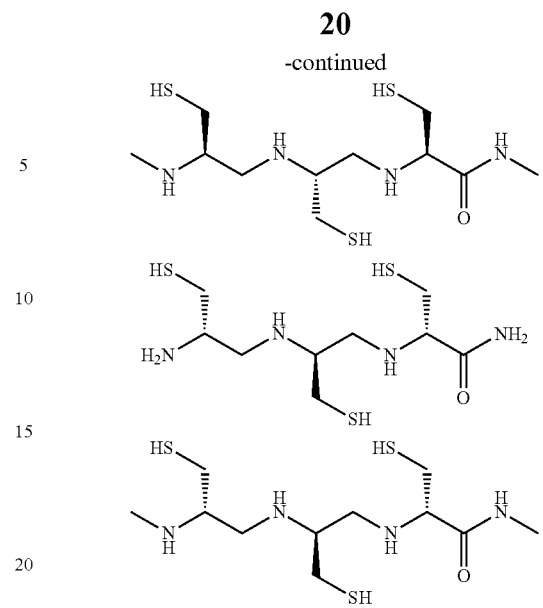
According to another aspect of the present invention, the method for preparing the compound of the present invention is provided:
preferably, as in route 1:
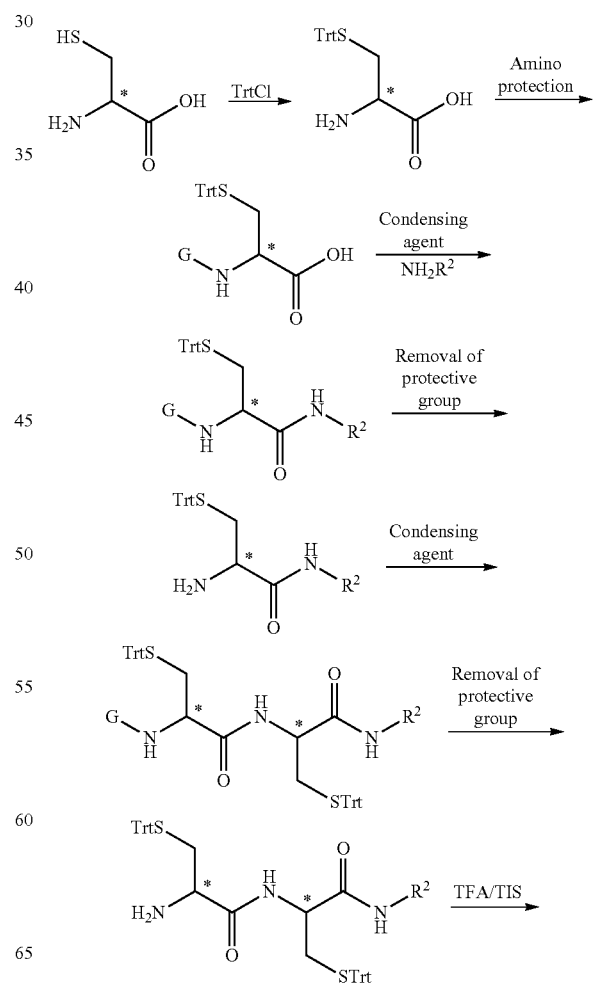

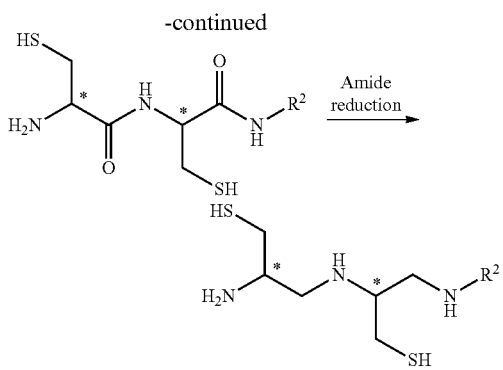

as in route 2

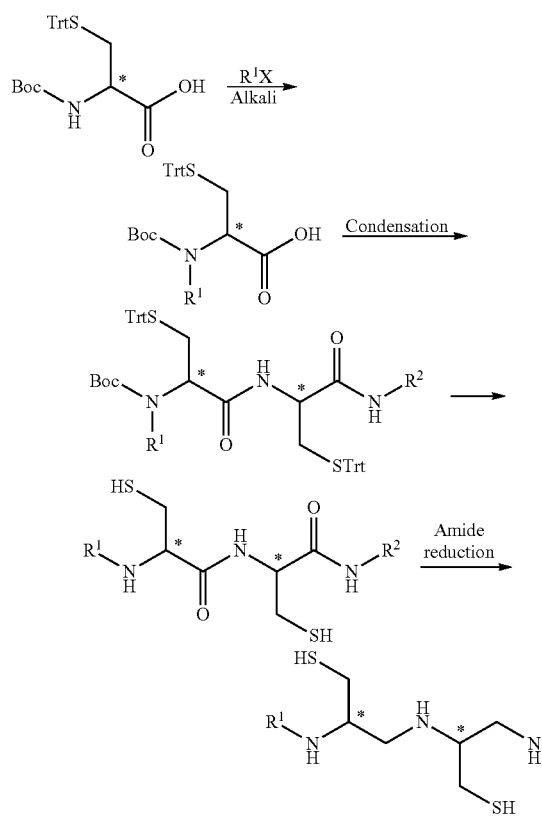

wherein R¹ and R² may be the same or different and are selected from: hydrogen, substituted or unsubstituted $C_1$-$C_5$ alkyl or heteroalkyl;

preferably, the amino-protecting group G is selected from: tert-butyloxycarbonyl, fluorenylmethoxycarbonyl (Fmoc), benzyloxycarbonyl, benzyl, and the like;

X is a halogen;

preferably, the condensing agent is selected from: Carbonyldiimidazole (CDI), 1-hydroxybenzotriazole (HOBT), 2-(7-oxidized benzotriazole)-N,N,N',N'-tetramethyluronium hexafluorophosphate (HATU), N,N'-dicyclohexylcarbodiimide (DCC), BOP, PyBOP, HBTU, TBTU, EDCI, etc.;

the corresponding amino-protecting group may be removed by an acid method such as formic acid, hydrochloric acid and trifluoroacetic acid or an alkali method such as piperidine, aqueous ammonia and triethylamine, or the corresponding amino-protecting group may also be removed by hydrogenation; and amide can be reduced to amine by borane, $NaBH_4$, $NaBH_4$-Lewis acid, lithium aluminum hydride and other methods.

According to a further aspect of the present invention, a pharmaceutical composition comprising the compound of the present invention and a derivative thereof are provided; preferably, the above pharmaceutical composition further comprises one or more pharmaceutically acceptable vehicles, carriers, adjuvants, auxiliaries or diluents;

preferably, the dosage forms of the pharmaceutical composition comprise but are not limited to: injections, emulsions, microemulsions, submicro-emulsions, nanoparticles, tablets, capsules, pills, inhalants, lozenges, gels, powder, suppositories, suspensions, creams, jellies, sprays, etc.;

preferably, the pharmaceutical composition can be administered by means of, but not limited to: subcutaneous injection, intramuscular injection, intravenous injection, oral administration, rectal administration, vaginal administration, nasal administration, transdermal administration, subconjunctival administration, intraocular administration, eyelid administration, retrobulbar administration, retinal administration, choroidal administration, intrathecal injection, and the like.

According to a further aspect of the present invention, the use of the compound of the present invention (e.g., a compound of formula I) and the pharmaceutical composition thereof in the preparation of drugs and/or cosmetics for the treatment and/or prevention of radiation damage and chemotherapy damage is provided.

The radiation comprises ionizing radiation, non-ionizing radiation or a combination of various types of radiation;

the ionizing radiation includes but is not limited to: alpha rays, beta rays, gamma rays, X rays, and neutron radiation;

the radiation damage comprises direct damage and indirect damage caused by radiation; preferably, the radiation damage comprises radiation-induced reduction of peripheral blood leukocytes, platelets and erythrocytes in mammals;

the chemotherapeutic drugs refer to the anti-tumor drugs that act on DNA, RNA, and tubulin, and that are vital to the survival of cells;

preferably, the use comprises the use of the above compound and the pharmaceutical composition thereof in the preparation of drugs and/or cosmetics for the treatment and/or prevention of sunburn damage; more preferably, the use comprises the use of the above compound and the pharmaceutical composition thereof in the preparation of cosmetics for the treatment and/or prevention of sunburn damage.

The compound of the present invention or a pharmaceutical composition thereof can be used alone as a radiation damage protection and treatment drug, or can be used in combination with a known radioprotectant, or can be combined with radiation therapy or chemotherapy to treat tumors, thereby reducing the adverse reactions of radiotherapy to surrounding tissues and organs and even the whole body, and alleviating and preventing the adverse reactions caused by radiotherapy.

The present invention also provides the use of the above compound or the pharmaceutical composition thereof in the preparation of anti-tumor drugs.

The present invention provides a novel stable compound which has the effects of reducing biological damage caused by ionizing radiation, extending the survival period and survival rate of the radiated animals, and significantly alleviating the side effects of radiotherapy, and has a low toxicity. The present invention opens up a new way for protection and treatment of ionizing radiation damage, wherein the radiation damage comprises direct damage and indirect damage caused by radiation; including radiation-induced reduction of peripheral blood leukocytes, platelets and erythrocytes in mammals. The chemotherapeutic drugs refer to the anti-tumor drugs that act on DNA, RNA, and tubulin, and that are vital to the survival of cells. The compounds provided by the present invention and derivatives thereof can also be used in combination with known radioprotectants.

BRIEF DESCRIPTION OF THE DRAWINGS

FIGS. 1A and 1B show the effect of compound 1 on the mice irradiated with 6.8Gy γ rays, wherein FIG. 1A shows the effect of compound 1 on 30-day survival rate of mice irradiated with 6.8Gy γ rays, FIG. 1B shows the effect of compound 1 on the body weight of mice irradiated with 6.8Gy γ rays.

FIGS. 2A-2J show the effect of compound 1 on organs and white blood cells in mice 30 days after irradiation with 6.8Gy γ rays, wherein FIG. 2A shows the effect of compound 1 on heart in mice 30 days after irradiation with 6.8Gy γ rays, FIG. 2B shows the effect of compound 1 on liver in mice 30 days after irradiation with 6.8Gy γ rays, FIG. 2C shows the effect of compound 1 on spleen in mice 30 days after irradiation with 6.8Gy γ rays, FIG. 2D shows the effect of compound 1 on lung in mice 30 days after irradiation with 6.8Gy γ rays, FIG. 2E shows the effect of compound 1 on kidney in mice 30 days after irradiation with 6.8Gy γ rays, FIG. 2F shows the effect of compound 1 on thymus in mice 30 days after irradiation with 6.8Gy γ rays, FIG. 2G shows the effect of compound 1 on testis in mice 30 days after irradiation with 6.8Gy γ rays, FIG. 2H shows the effect of compound 1 on splenic nodules in mice 30 days after irradiation with 6.8Gy γ rays, FIG. 2I shows the effect of compound 1 on unilateral femoral bone marrow leukocytes in mice 30 days after irradiation with 6.8Gy γ rays, FIG. 2J shows the effect of compound 1 on white blood cells in blood of mice 30 days after irradiation with 6.8Gy γ rays.

FIGS. 3A and B show the effect of compounds 1-4 on the survival rate and body weight of mice 30 days after irradiation with 7.2Gy γ rays, wherein FIG. 3A shows the effect of compounds 1-4 on survival rate of mice 30 days after irradiation with 7.2Gy γ rays.

FIGS. 4A-4J show the effect of compounds 1-4 on organs and white blood cells in mice 30 days after irradiation with 7.2Gy γ rays, wherein FIG. 4A shows the effect of compounds 1-4 on heart in mice 30 days after irradiation with 7.2Gy γ rays, FIG. 4B shows the effect of compounds 1-4 on liver in mice 30 days after irradiation with 7.2Gy γ rays, FIG. 4C shows the effect of compounds 1-4 on spleen in mice 30 days after irradiation with 7.2Gy γ rays, FIG. 4D shows the effect of compounds 1-4 on lung in mice 30 days after irradiation with 7.2Gy γ rays, FIG. 4E shows the effect of compounds 1-4 on kidney in mice 30 days after irradiation with 7.2Gy γ rays, FIG. 4F shows the effect of compounds 1-4 on thymus in mice 30 days after irradiation with 7.2Gy γ rays, FIG. 4G shows the effect of compounds 1-4 on testis in mice 30 days after irradiation with 7.2Gy γ rays, FIG. 4H shows the effect of compounds 1-4 on splenic nodules in mice 30 days after irradiation with 7.2Gy γ rays, FIG. 4I shows the effect of compounds 1-4 on unilateral femoral bone marrow leukocytes in mice 30 days after irradiation with 7.2Gy γ rays, FIG. 4J shows the effect of compounds 1-4 on white blood cells in blood of mice 30 days after irradiation with 7.2Gy γ rays.

FIGS. 5A and 5B show the effect of compound 1 on survival rate and body weight of mice 30 days after irradiation with 7.5Gy γ rays, wherein FIG. 5A shows the effect of compound 1 on survival rate of mice 30 days after irradiation with 7.5Gy γ rays, FIG. 5B shows the effect of compound 1 on the body weight of mice irradiated with 7.5Gy γ rays.

FIGS. 6A-6J show the effect of amifostine on organs and white blood cells in mice 30 days after irradiation with 7.5Gy γ rays, wherein FIG. 6A shows the effect of amifostine on heart in mice 30 days after irradiation with 7.5Gy γ rays, FIG. 6B shows the effect of amifostine on liver in mice 30 days after irradiation with 7.5Gy γ rays, FIG. 6C shows the effect of amifostine on spleen in mice 30 days after irradiation with 7.5Gy γ rays, FIG. 6D shows the effect of amifostine on lung in mice 30 days after irradiation with 7.5Gy γ rays, FIG. 6E shows the effect of amifostine on kidney in mice 30 days after irradiation with 7.5Gy γ rays, FIG. 6F shows the effect of amifostine on thymus in mice 30 days after irradiation with 7.5Gy γ rays, FIG. 6G shows the effect of amifostine on testis in mice 30 days after irradiation with 7.5Gy γ rays, FIG. 6H shows the effect of amifostine on splenic nodules in mice 30 days after irradiation with 7.5Gy γ rays, FIG. 6I shows the effect of amifostine on unilateral femoral bone marrow leukocytes in mice 30 days after irradiation with 7.5Gy γ rays, FIG. 6J shows the effect of amifostine on white blood cells in blood of mice 30 days after irradiation with 7.5Gy γ rays.

FIGS. 7A-7F show the effects of irradiation on peripheral blood, wherein FIG. 7A shows the peripheral white blood cell (WBC) count, FIG. 7B shows the peripheral red blood cell (RBC) count, FIG. 7C shows the peripheral hemoglobin (HGB) concentration, FIG. 7D shows the peripheral platelet (PLT) count, FIG. 7E shows the peripheral blood lymphocyte ratio (LY %), FIG. 7F shows the peripheral blood neutrophil ratio (NE %).

FIGS. 8A-8E show the effect of irradiation on bone marrow cells, wherein FIG. 8A shows the number of leukocytes in bone marrow, FIG. 8B shows the ratio of hematopoietic stem cell (LSK) in bone marrow cells, FIG. 8C shows the ratio of hematopoietic progenitor cells (HPC) in bone marrow cells, FIG. 8D shows the ratio of CD34−LSK in bone marrow cells, FIG. 8E shows the ratio of CD34+ LSK in bone marrow cells.

FIGS. 9A and 9B show the effect of irradiation on the levels of reactive oxygen species (ROS) in LSK cells and the levels of ROS in HPC cells, wherein FIG. 9A shows the levels of reactive oxygen species (ROS) in LSK cells, FIG. 9B shows the levels of ROS in HPC cells.

DETAILED DESCRIPTION OF EMBODIMENTS

Figure 1A:
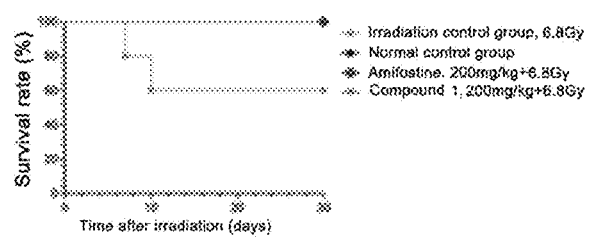

According to the present invention, the term "radiation damage" in the present invention refers to the injury caused by various rays in the electromagnetic spectrum, such as microwave, infrared ray, visible light, ultraviolet ray, X ray, beta ray and gamma ray. Neutron or proton beam irradiation can also cause such damage.

The term "pharmaceutically acceptable salt" refers to any salt (generally referred to as non-toxic) that is physiologically compatible when used in an appropriate manner for treatment, use, or especially in humans and/or mammals. Unless otherwise stated, salts of acidic groups which may be present in the compounds of the present invention (for example, but not limited to, potassium salts, sodium salts, magnesium salts, calcium salts, etc.) or salts of basic groups (for example, but not limited to, sulfates, hydrochlorides, phosphates, nitrates, carbonates, etc.).

The term "solvate" refers to a complex compound of molecules of solute or ions in a solution, formed by attracting neighboring solvent molecules through intermolecular forces such as coulomb force, van der Waals force, charge transfer force, and hydrogen bond. In one embodiment, the solvent is water, that is, the compound of the invention forms a hydrate.

Depending on the substituent, the compound in formula (I) may be in the form of optically active isomers or mixtures of isomers of different compositions, and the mixtures may be separated by conventional means if appropriate. The present invention provides pure isomers and mixtures of isomers, methods for preparation and uses, and compositions comprising them. For the sake of simplicity, it is referred to below as a compound of formula (I), which refers to both pure optical isomers and, where appropriate, mixtures of different proportions of isomers.

A person skilled in the art will have a better understanding of the above and other purposes, advantages and characteristics of the present invention according to the following and the detailed description of the specific embodiments of the present invention in conjunction with the accompanying drawings. A person skilled in the art will have a better understanding of the above and other purposes, advantages and characteristics of the present invention according to the following and the detailed description of the specific embodiments of the present invention in conjunction with the accompanying drawings.

Synthesis

Suitable solvents commonly used in organic reactions can be used in the following various steps of the preparation method of the present invention, such as, but not limited to, aliphatic and aromatic, optionally hydrocarbon or halogenated hydrocarbons (e.g., pentane, hexane, heptane, cyclohexane, petroleum ether, gasoline, volatile oil, benzene, toluene, xylene, dichloromethane, dichloroethane, chloroform, carbon tetrachloride, chlorobenzene and o-dichlorobenzene); aliphatic and aromatic, optional alcohols (e.g., methanol, ethanol, propanol, isopropanol, tertiary butanol, ethylene glycol, etc.), ethers (e.g., diethyl ether and dibutyl ether, ethylene glycol dimethyl ether and diglyme, tetrahydrofuran and dioxane, etc.), esters (e.g., methyl acetate or ethyl acetate, etc.), nitriles (e.g., acetonitrile or propionitrile, etc.), ketone (e.g., acetone, methyl ethyl ketone, etc.), amides (e.g., dimethylformamide, dimethylacetamide, N-methylpyrrolidone, etc.); as well as dimethyl sulfoxide, tetramethylene sulfone and hexamethylphosphoric triamide and N,N-dimethyl propylene urea (DMPU), etc.

SYNTHESIS EXAMPLES

The present invention may be further explained by the following examples which do not imply any limitation to the present invention.

Example 1: Synthesis of (R)-2-amino-N—((R)-1-amino-3-mercapto-1-oxopropan-2-yl)-3-mercapto-propanamide trifluoroacetate

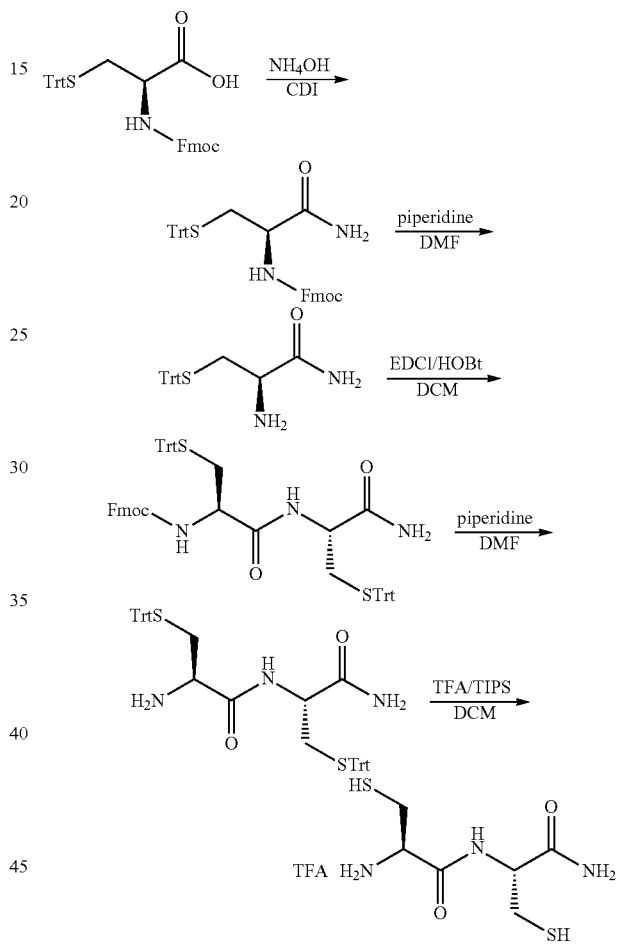

Step 1: Synthesis of (9H-fluoren-9-yl) methyl (R)-(1-amino-1-oxo-3-(tritylthio)propan-2-yl) carbamate

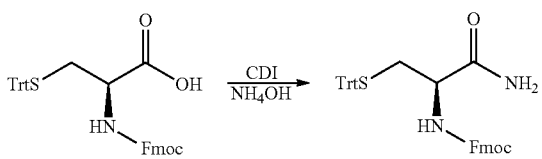

The compound (R)-2-(((9H-fluoren-9-yl)methoxy)carbonyl)amino)-3-(tritylthio) propionic acid (10 g, 17.07 mmol) was dissolved in tetrahydrofuran (50 ml). N,N'-carbonyldiimidazole (5.59 g, 34.48 mmol) was added at 0-5° C. After stirring for 2 hours under nitrogen protection, aqueous ammonia (5 ml, 68.28 mmol) was added, and reacted at 0-5° C. for 30 minutes. After the reaction was completed as detected by TLC, 2 M hydrochloric acid (60 ml) was added for quenching. The reaction mixture was extracted with ethyl acetate, the organic phase was washed with a saturated saline, then dried with sodium sulfate, and concentrated to obtain a crude product. After adding anhydrous methanol (20 ml) and stirring at room temperature overnight, white solids were precipitated, and filtered to obtain the product in the filter cake. The methanol phase was concentrated and separated by column chromatography (methanol:dichloromethane: 1%-5%) to obtain the target product as a white solid (9.3 g, yield: 93.19%). $^1$H NMR (400 MHz, DMSO-d6) δ 7.89 (d, 2H), 7.74 (d, 2H), 7.58 (d, 1H), 7.3 (m, 18H), 7.11 (s, 1H), 4.24 (m, 3H), 4.01 (m, 1H), 2.39 (m, 2H).

Step 2: Synthesis of (R)-2-amino-3-(tritylthio) propionamide

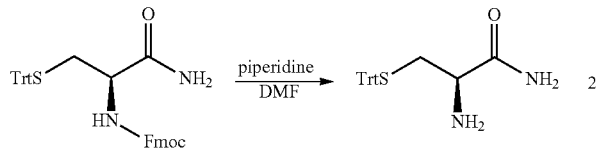

The compound (9H-fluoren-9-yl) methyl (R)-(1-amino-1-oxo-3-(tritylthio)propan-2-yl) carbamate (4 g, 6.84 mmol) was dissolved in N,N-dimethylformamide (20 ml). Piperidine (0.14 ml, 1.368 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane=1%-5%) to obtain the target product as a yellow oil (2.3 g, yield: 92%). $^1$H NMR (400 MHz, DMSO-d6) δ 7.29 (m, 17H), 3.08 (d, 1H), 2.33 (d, 1H), 2.18 (s, 1H), 1.85 (s, 2H).

Step 3: Synthesis of (9H-fluoren-9-yl) methyl ((R)-1-(((R)-1-amino-1-oxo-3-(tritylthio)propan-2-yl) amino)-1-oxo-3-(tritylthio)propan-2-yl) carbamate

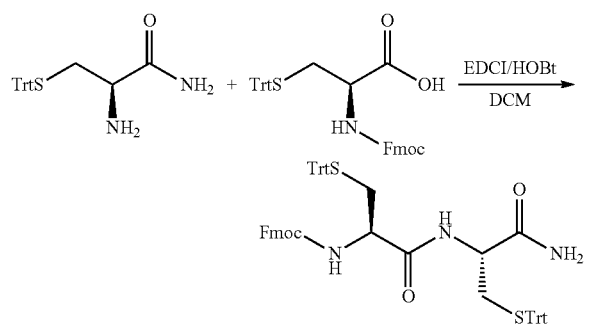

The compound (R)-2-((((9H-fluoren-9-yl)methoxy)carbonyl)amino)-3-(tritylthio) propanoic acid (1.29 g, 2.21 mmol) was dissolved in dichloromethane (15 ml). 1-hydroxybenzotriazole (448 mg, 3.315 mmol) and EDCI (635 mg, 3.315 mmol) were added, and stirred at room temperature for 5 min. (9H-fluoren-9-yl) methyl (R)-(1-amino-1-oxo-3-(tritylthio)propan-2-yl) carbamate (960 mg, 2.65 mmol) was added and reacted at room temperature for 30 minutes. After the reaction was completed as detected by TLC, the mixture was washed with a saturated saline and extracted with dichloromethane. The organic phase was dried with sodium sulfate, concentrated, and separated by column chromatography (methanol:dichloromethane: 1%-5%) to obtain the product as a white solid (2.05 g, yield: 99.76%). $^1$H NMR (400 MHz, DMSO-d6) δ 7.89 (m, 3H), 7.7 (m, 3H), 7.4 (m, 2H), 7.24 (m, 34H), 4.21 (m, 4H), 4.10 (m, 1H), 2.33 (m, 4H).

Step 4: Synthesis of (R)-2-amino-N—((R)-1-amino-1-oxo-3-(tritylthio) propan-2-yl)-3-(tritylthio) propionamide

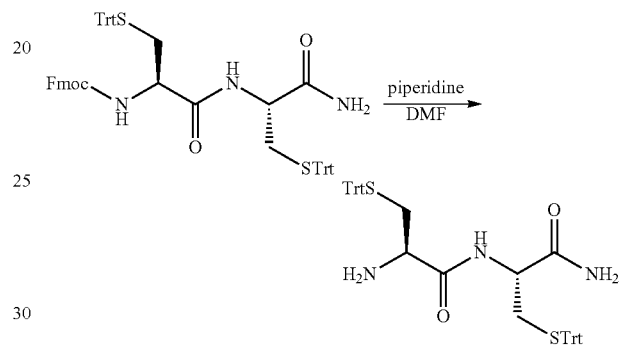

The compound (9H-fluoren-9-yl) methyl ((R)-1-(((R)-1-amino-1-oxo-3-(tritylthio)propan-2-yl) amino)-1-oxo-3-(tritylthio)propan-2-yl) carbamate (2.05 g, 2.2 mmol) was dissolved in N,N-dimethylformamide (20 ml). Piperidine (0.04 ml, 0.44 mmol) was added and stirred at room temperature for 4 hours. After the reaction was completed as detected by TLC detection, the reaction mixture was washed with a saturated saline and extracted with dichloromethane. The organic phase was dried with sodium sulfate, concentrated, and separated by column chromatography (methanol:dichloromethane: 1%-5%) to obtain the product as a white solid (600 mg, yield: 38.54%). $^1$H NMR (400 MHz, DMSO-d6) δ 8.1 (s, 1H), 7.37-7.14 (m, 32H), 4.23 (m, 1H), 3.17 (m, 1H), 2.39 (dd, 1H), 2.33 (d, 2H), 2.19 (m, 1H).

Step 5: Synthesis of (R)-2-amino-N—((R)-1-amino-3-mercapto-1-oxopropan-2-yl)-3-mercaptopropanamide trifluoroacetate

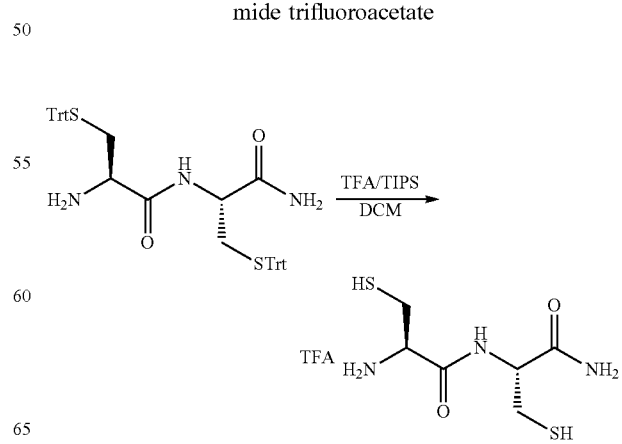

The compound (R)-2-amino-N—((R)-1-amino-1-oxo-3-(tritylthio)propan-2-yl)-3-(tritylthio) propionamide (150 mg, 0.21 mmol) was dissolved in dichloromethane (5 ml). Triisopropylsilane (0.11 ml, 0.525 mmol) and trifluoroacetic acid (1 ml) were added at 0° C. under a nitrogen atmosphere and stirred in an ice bath for 2 hours. After the reaction was completed as detected by TLC, the mixture was concentrated, diethyl ether was added, and stirred in the ice bath. White solids were precipitated, filtered and dried to obtain the product (60 mg, yield: 84.7%). $^1$H NMR (400 MHz, DMSO-d6) δ 8.72 (d, 1H), 8.23 (s, 3H), 7.56 (s, 1H), 7.32 (s, 1H), 4.43 (m, 1H), 4.09 (m, 1H), 2.99 (d, 2H), 2.89 (m, 1H), 2.74 (m, 1H); HESI: 224.05 [M+H]$^+$.

Example 2: Synthesis of (R)-3-mercapto-N—((R)-3-mercapto-1-(methylamino)-1-oxopropan-2-yl)-2-(methylamino) propionamide trifluoroacetate

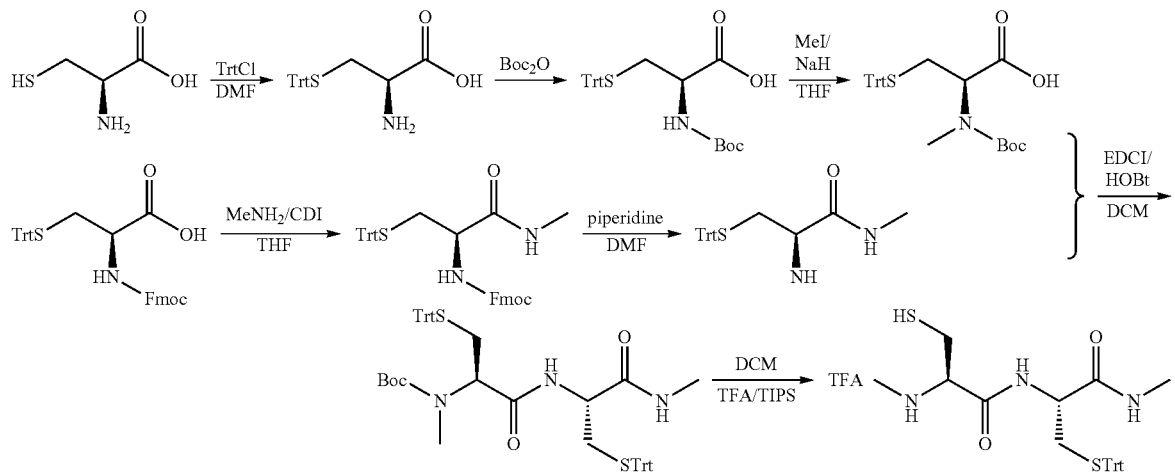

Step 1: Synthesis of S-trityl-L-cysteine

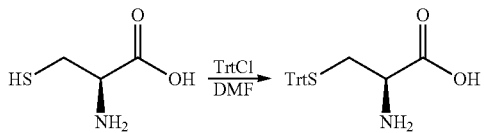

The compound L-cysteine hydrochloride (10 g, 63.45 mmol) was dissolved in N,N-dimethylformamide (120 ml). Triphenylchloromethane (19.46 g, 69.795 mmol) was added, heated to 60-65° C., and reacted for 8 h. After the reaction was completed as detected by TLC, the reaction was cooled to room temperature, and 10% sodium acetate solution (300 ml) was added. White solids were then precipitated and filtered. Filter residue was washed with pure water (300 ml), then washed with acetone (200 ml), and dried to obtain the product as a white solid (17.56 g, yield: 76.15%). $^1$H NMR (400 MHz, DMSO-d6) δ 7.28 (m, 18H), 2.92 (dd, 1H), 2.59 (dd, 1H), 2.41 (dd, 1H).

Step 2: Synthesis of N-(tert-butoxycarbonyl)-S-trityl-L-cysteine

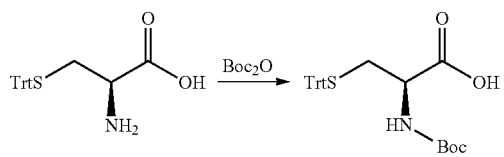

The compound S-trityl-L-cysteine (5 g, 13.76 mmol) was dissolved in a mixture of dioxane (40 ml), water (20 ml) and 1M sodium hydroxide solution (14 ml), and stirred in an ice bath. Boc-anhydride (3.5 ml, 15.14 mmol) was added, then reacted until the mixture was naturally warmed to room temperature, and stirred for 8 hours. After the reaction was completed as detected by TLC, the reaction mixture was concentrated to 20-25 ml. Ethyl acetate was added, and the sodium bisulfate solution was added dropwise under the ice bath while stirring. After pH was adjusted to 2-3, ethyl acetate was used for extraction. The organic layer was washed with a saturated saline, then dried with sodium sulfate, concentrated, and separated by column chromatography (methanol:dichloromethane: 1%-5%) to obtain the product as a white solid (5.5 g, yield: 86.21%). $^1$H NMR (400 MHz, DMSO-d6) δ 7.26 (m, 16H), 3.78 (d, 1H), 2.51 (m, 1H), 2.36 (dd, 1H), 1.4 (d, 9H).

Step 3: Synthesis of N-(tert-butoxycarbonyl)-N-methyl-S-trityl-L-cysteine

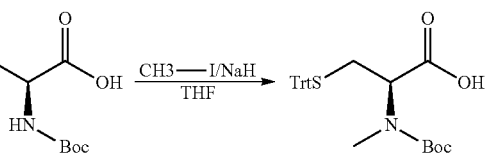

The compound N-(tert-butoxycarbonyl)-S-trityl-L-cysteine (2.1 g, 4.53 mmol) was dissolved in anhydrous tetrahydrofuran (6 ml). Sodium hydride (436 mg, 10.9 mmol) was dissolved in anhydrous tetrahydrofuran (14 ml). The solution of amino acid in tetrahydrofuran was added dropwise to the solution of sodium hydride in tetrahydrofuran in an ice bath. Then, methyl iodide (0.93 ml, 14.95 mmol) was slowly added dropwise and stirred overnight. After the reaction was completed as detected by TLC, phosphate buffer at pH=7 was added for quenching. pH was adjusted to 6-7 with a saturated ammonium chloride solution, and was extracted with ethyl acetate. The organic layer was washed with a saturated saline, then dried with sodium sulfate, concentrated, and separated by column chromatography (methanol:dichloromethane: 1%-5%) to obtain the product as a white solid (1.3 g, yield: 60.19%). $^1$H NMR (400 MHz, DMSO-d6) δ 7.3 (m, 15H), 3.75 (s, 1H), 2.8 (s, 1H), 2.66 (d, 4H), 1.4 (d, 9H).

Step 4: Synthesis of (9H-fluoren-9-yl) methyl (R)-(1-(methylamino)-1-oxo-3-(tritylthio)propan-2-yl) carbamate

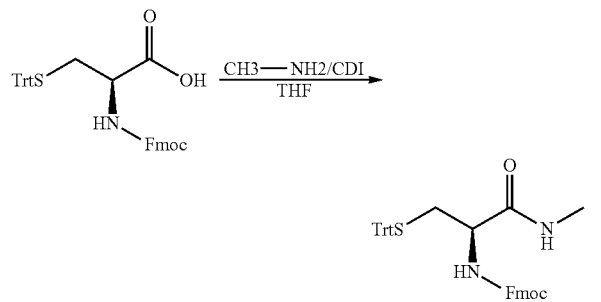

The compound (R)-2-(((9H-fluoren-9-yl)methoxy)carbonyl)amino)-3-(tritylthio) propionic acid (10 g, 17.07 mmol) was dissolved in tetrahydrofuran (50 ml). N,N'-carbonyldiimidazole (5.59 g, 34.48 mmol) was added at 0-5° C. After stirring for 2 hours under nitrogen atmosphere, methylamine (3.03 ml, 68.28 mmol) was added, and reacted at 0-5° C. for 2 hours. After the reactants were consumed, 2M hydrochloric acid (60 ml) was added for quenching, and the reaction mixture was extracted with dichloromethane. The organic layer was washed with a saturated saline, then dried with sodium sulfate and concentrated to obtain a crude product. Methanol (20 ml) was added and stirred overnight at room temperature. White solids were precipitated, and filtered to obtain the product in filter residue. The methanol phase was concentrated, and separated by column chromatography (methanol:dichloromethane: 1%-5%) to obtain a white solid (9.44 g, yield: 92.37%). $^1$H NMR (400 MHz, DMSO) δ 7.89 (d, 2H), 7.81 (d, 1H), 7.74 (d, 2H), 7.66 (d, 1H), 7.41 (t, 2H), 7.29 (m, 17H), 4.31 (d, 1H), 4.22 (t, 2H), 4.00 (d, 1H), 2.53 (d, 3H), 2.39 (d, 2H).

Step 5: Synthesis of (R)-2-amino-N-methyl-3-(tritylthio) propionamide

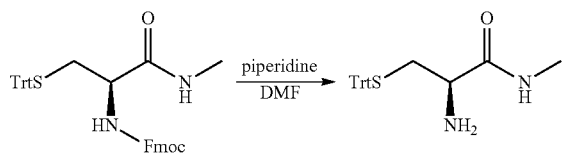

The compound (9H-fluoren-9-yl) methyl (R)-(1-(methylamino)-1-oxo-3-(tritylthio)propan-2-yl) carbamate (2 g, 3.34 mmol) was dissolved in N,N-dimethylformamide (20 ml). Piperidine (0.07 ml, 0.668 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane: 1%-5%) to obtain the product as a yellowish white solid (879 mg, yield: 69.76%). $^1$H NMR (400 MHz, CDCl$_3$) δ 7.77 (d, 1H), 7.29 (m, 15H), 3.08 (m, 1H), 2.55 (d. 3H), 2.37 (dd, 1H), 2.19 (dd, 1H), 1.80 (s, 2H).

Step 6: Synthesis of tert-butyl methyl ((R)-1-(((R)-1-(methylamino)-1-oxo-3-(tritylthio)propan-2-yl)amino)-1-oxo-3-(tritylthio)propan-2-yl) carbamate

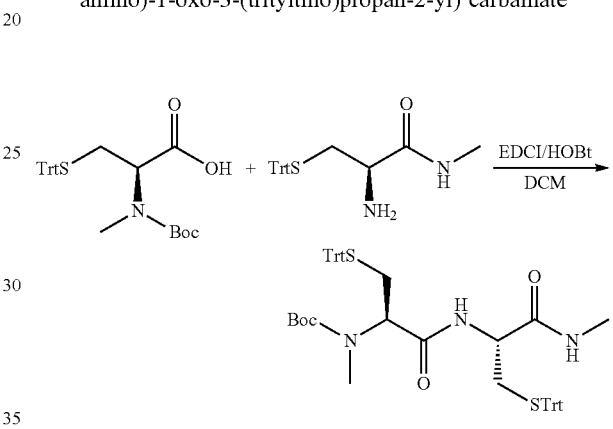

The compound N-(tert-butoxycarbonyl)-N-methyl-S-trityl-L-cysteine (150 g, 0.314 mmol) was dissolved in dichloromethane (5 ml). 1-hydroxybenzotriazole (63.7 mg, 0.471 mmol) and EDCI (90.3 mg, 0.471 mmol) were added, and stirred at room temperature for 5 min. (R)-2-amino-N-methyl-3-(tritylthio) propanamide (141.9 mg, 0.377 mmol) was added and stirred at room temperature for 30 minutes. After the reaction was completed as detected by TLC, the mixture was washed with a saturated saline and extracted with dichloromethane. The organic phase was dried with sodium sulfate, then concentrated and purified with TLC (dichloromethane:methanol: 15:1) to obtain the product as a white solid (260 mg, yield: 99.2%). $^1$H NMR (400 MHz, CDCl$_3$) δ 7.39 (m, 12H), 7.22 (m, 20H), 4.1 (d, 1H), 3.95 (s, 1H), 2.61 (dd, 10H), 1.39 (s, 9H).

Step 7: Synthesis of (R)-3-mercapto-N—((R)-3-mercapto-1-(methylamino)-1-oxopropan-2-yl)-2-(methylamino) propionamide trifluoroacetate

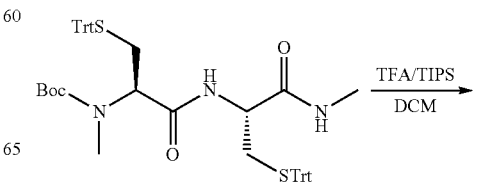

-continued

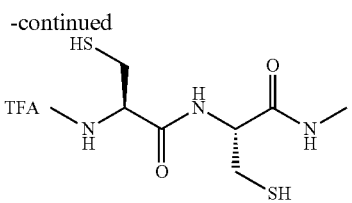

The compound tert-butyl methyl ((R)-1-(((R)-1-(methyl-amino)-1-oxo-3-(tritylthio)propan-2-yl)amino)-1-oxo-3-(tritylthio)propan-2-yl) carbamate (1.1 g, 1.32 mmol) was dissolved in dichloromethane:trifluoroacetic acid:triisopropylsilane (50:47:3 by volume) (25 ml), stirred at room temperature for 5 min. After the reaction was completed as detected by TLC, the mixture was concentrated, diethyl ether was added, and stirred in an ice bath. White solids were precipitated, filtered and dried to obtain the product (400 mg, yield: 86.9%). $^1$H NMR (400 MHz, MeOD) δ 4.5 (m, 1H), 4.07 (t, 1H), 3.18-2.96 (m, 3H), 2.82 (m, 1H), 2.78 (s, 3H), 2.74 (s, 3H); HESI: 252.08[M+H]$^+$.

Example 3: Synthesis of (R)-2-amino-N—((R)-1-(((R)-1-amino-3-mercapto-1-oxopropan-2-yl)amino)-3-mercapto-1-oxopropan-2-yl)-3-mercapto-propanamide trifluoroacetate

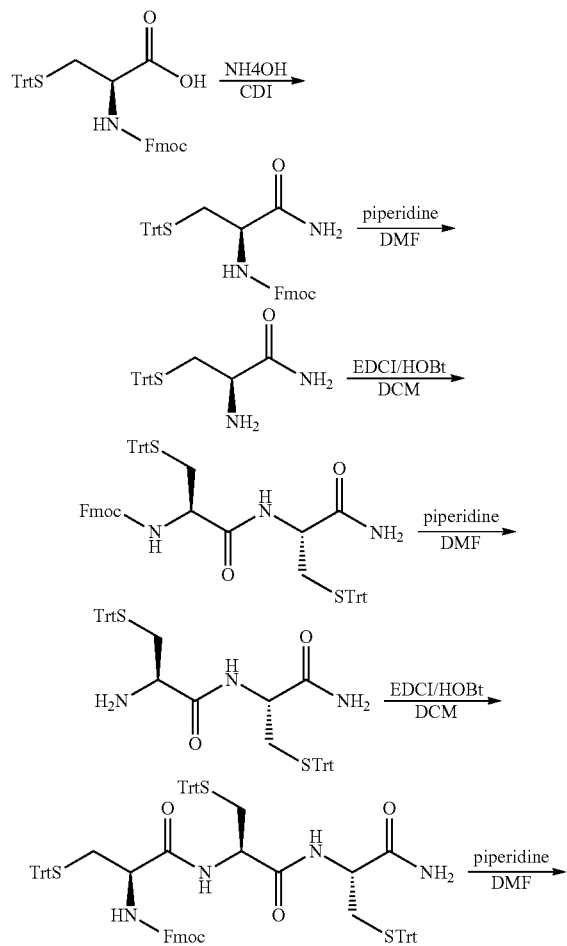

-continued

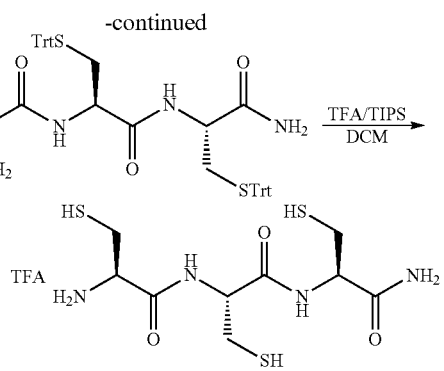

Step 1: Synthesis of (9H-fluoren-9-yl) methyl (R)-(1-amino-1-oxo-3-(tritylthio)propan-2-yl) carbamate

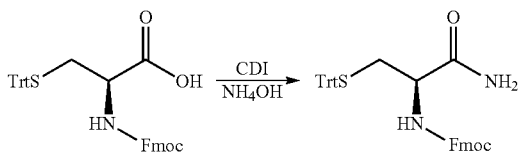

The compound (R)-2-(((9H-fluoren-9-yl)methoxy)carbonyl)amino)-3-(tritylthio) propionic acid (10 g, 17.07 mmol) was dissolved in tetrahydrofuran (50 ml). N,N'-carbonyldiimidazole (5.59 g, 34.48 mmol) was added at 0-5° C. After stirring for 2 hours under nitrogen atmosphere, aqueous ammonia (5 ml, 68.28 mmol) was added, and reacted at 0-5° C. for 30 minutes. After the reactants were consumed, 2M hydrochloric acid (60 ml) was added for quenching. The reaction mixture was extracted with ethyl acetate. The organic layer was washed with a saturated saline, then dried with sodium sulfate, evaporated under reduced pressure to remove the solvent, thereby obtaining a crude product. After adding anhydrous methanol (20 ml) and stirring at room temperature overnight, white solids were precipitated, and filtered to obtain a product in the filter residue. The methanol phase was concentrated and separated by column chromatography (methanol:dichloromethane: 1%-5%) to obtain a white solid (a total of 9.3 g products, yield: 93.19%). $^1$H NMR (400 MHz, DMSO-d6) δ 7.89 (d, 2H), 7.74 (d, 2H), 7.58 (d, 1H), 7.3 (m, 18H), 7.11 (s, 1H), 4.24 (m, 3H), 4.01 (m, 1H), 2.39 (m, 2H).

Step 2: Synthesis of (R)-2-amino-3-(tritylthio) propionamide

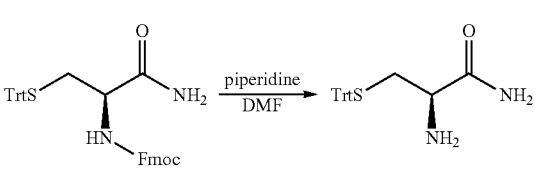

The compound (9H-fluoren-9-yl) methyl (R)-(1-amino-1-oxo-3-(tritylthio)propan-2-yl) carbamate (4 g, 6.84 mmol) was dissolved in N,N-dimethylformamide (20 ml). Piperidine (0.14 ml, 1.368 mmol) was added and reacted at room temperature for 4 hours. After the reaction was completed as detected by TLC, the reaction mixture was washed with a saturated saline and extracted with dichloromethane. The organic phase was dried with sodium sulfate, then concentrated, and separated by column chromatography (methanol:dichloromethane: 1%-5%) to obtain the product as a yellow oil (2.3 g, yield: 92%). $^1$H NMR (400 MHz, DMSO-d6) δ 7.29 (m, 17H), 3.08 (d, 1H), 2.33 (d, 1H), 2.18 (s, 1H), 1.85 (s, 2H).

Step 3: Synthesis of (9H-fluoren-9-yl) methyl ((R)-1-(((R)-1-amino-1-oxo-3-(tritylthio)propan-2-yl)amino)-1-oxo-3-(tritylthio)propan-2-yl) carbamate

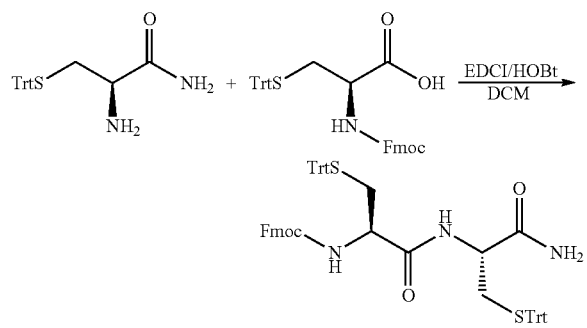

The compound (R)-2-((((9H-fluoren-9-yl)methoxy)carbonyl)amino)-3-(tritylthio) propanoic acid (1.29 g, 2.21 mmol) was dissolved in dichloromethane (15 ml). 1-hydroxybenzotriazole (448 mg, 3.315 mmol) and EDCI (635 mg, 3.315 mmol) were added, and stirred at room temperature for 5 min. (9H-fluoren-9-yl) methyl (R)-(1-amino-1-oxo-3-(tritylthio)propan-2-yl) carbamate (960 mg, 2.65 mmol) was added and reacted at room temperature for 30 minutes. After the reaction was completed as detected by TLC, the mixture was washed with a saturated saline and extracted with dichloromethane. The organic phase was dried with sodium sulfate, then concentrated, and separated by column chromatography (methanol:dichloromethane: 1%-5%) to obtain the product as a white solid (2.05 g, yield: 99.76%). $^1$H NMR (400 MHz, DMSO-d6) δ 7.89 (m, 3H), 7.7 (m, 3H), 7.4 (m, 2H), 7.24 (m, 34H), 4.21 (m, 4H), 4.10 (m, 1H), 2.33 (m, 4H).

Step 4: Synthesis of (R)-2-amino-N—((R)-1-amino-1-oxo-3-(tritylthio) propan-2-yl)-3-(tritylthio) propionamide

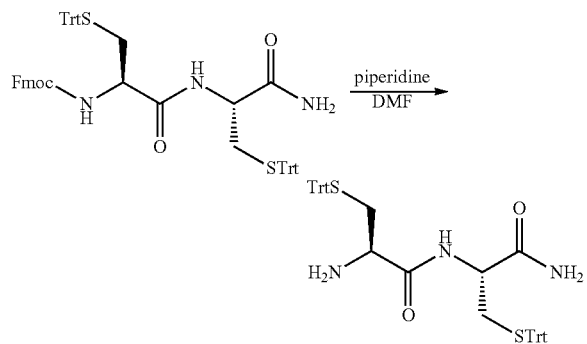

The compound (9H-fluoren-9-yl) methyl ((R)-1-(((R)-1-amino-1-oxo-3-(tritylthio)propan-2-yl) amino)-1-oxo-3-(tritylthio)propan-2-yl) carbamate (2.05 g, 2.2 mmol) was dissolved in N,N-dimethylformamide (20 ml). Piperidine (0.04 ml, 0.44 mmol) was added and stirred at room temperature for 4 hours. After the reaction was completed as detected by TLC detection, the reaction mixture was washed with a saturated saline and extracted with dichloromethane. The organic phase was dried with sodium sulfate, then concentrated, and separated by column chromatography (methanol:dichloromethane: 1%-5%) to obtain a white solid (600 mg, yield: 38.54%). $^1$H NMR (400 MHz, DMSO-d6) δ 8.1 (s, 1H), 7.37-7.14 (m, 32H), 4.23 (m, 1H), 3.17 (m, 1H), 2.39 (dd, 1H), 2.33 (d, 2H), 2.19 (m, 1H).

Step 5: Synthesis of (9H-fluoren-9-yl) methyl ((4R,7R,10R)-4-carbamoyl-6,9-dioxo 1,1,1,13,13,13-hexaphenyl-7-((tritylthio)methyl)-2,12-dithia-5,8-diazatridec-10-yl) carbamate

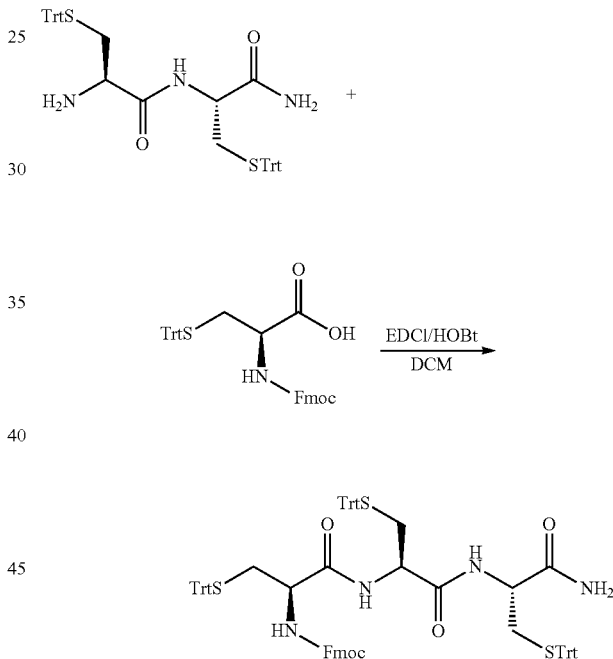

The compound (R)-2-((((9H-fluoren-9-yl)methoxy)carbonyl)amino)-3-(tritylthio) propanoic acid (688.21 mg, 1.175 mmol) was dissolved in dichloromethane (5 ml). 1-hydroxybenzotriazole (237.95 mg, 1.76 mmol) and EDCI (337.39 mg, 1.76 mmol) were added, and stirred at room temperature for 5 min. (R)-2-amino-N—((R)-1-amino-1-oxo-3-(tritylthio)propan-2-yl)-3-(tritylthio) propanamide (1 g, 1.41 mmol) was added and reacted at room temperature for 30 minutes. After the reaction was completed as detected by TLC, the mixture was washed with a saturated saline and extracted with dichloromethane. The organic phase was dried with sodium sulfate, then concentrated, and separated by column chromatography (methanol:dichloromethane: 1%-5%) to obtain the product as a white solid (1.4 g, yield: 93.33%). $^1$H NMR (400 MHz, DMSO) δ 8.03 (s, 3H), 7.87 (d, 2H), 7.55 (d, 2H), 7.38-7.26 (m, 49H), 4.81-4.70 (m, 5H), 4.46 (m, 1H), 3.28-2.81 (m, 6H).

Step 6: Synthesis of (R)-2-amino-N—((R)-1-(((R)-1-amino-1-oxo-3-(tritylthio)propan-2-yl)amino)-1-oxo-3-(tritylthio)propan-2-yl)-3-(tritylthio) propionamide

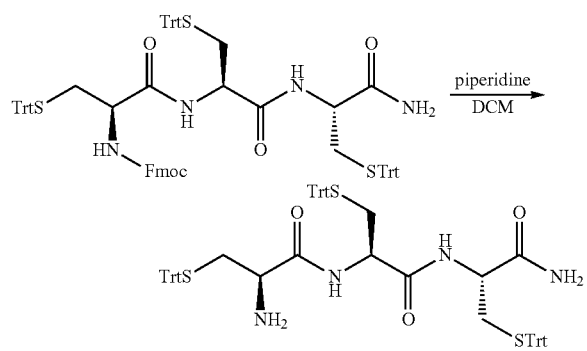

The compound (9H-fluoren-9-yl) methyl ((4R,7R,10R)-4-carbamoyl-6,9-dioxo 1,1,1,13,13,13-hexaphenyl-7-((tritylthio)methyl)-2,12-dithia-5,8-diazatridec-10-yl) carbamate (1.4 g, 1.1 mmol) was dissolved in N,N-dimethylformamide (10 ml). Piperidine (0.02 ml, 0.22 mmol) was added and stirred at room temperature for 4 hours. After the reaction was completed as detected by TLC, the reaction mixture was washed with a saturated saline and extracted with dichloromethane. The organic phase was dried with sodium sulfate, then concentrated, and separated by column chromatography (methanol:dichloromethane: 1%-5%) to obtain a white solid (748 mg, yield: 64.48%). $^1$H NMR (400 MHz, DMSO) δ 8.03 (s, 2H), 7.33-7.16 (m, 45H), 4.81 (m, 2H), 3.84 (m, 1H), 3.26-2.78 (m, 6H).

Step 7: Synthesis of (R)-2-amino-N—((R)-1-(((R)-1-amino-3-mercapto-1-oxopropan-2-yl)amino)-3-mercapto-1-oxopropan-2-yl)-3-mercaptopropanamide trifluoroacetate

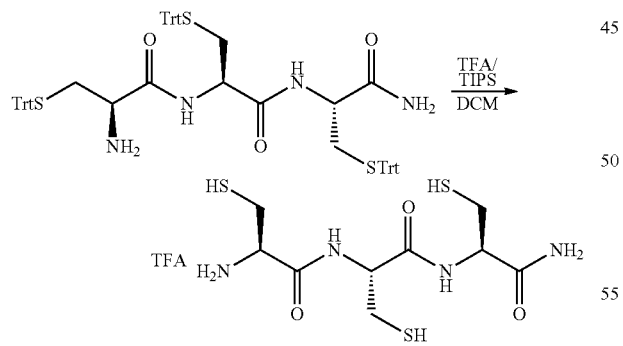

The compound (R)-2-amino-N—((R)-1-(((R)-1-amino-1-oxo-3-(tritylthio)propan-2-yl)amino)-1-oxo-3-(tritylthio) propan-2-yl)-3-(tritylthio) propionamide (1.2 g, 1.1 mmol) was dissolved in dichloromethane (10 ml). Triisopropylsilane (0.56 ml, 2.75 mmol) and trifluoroacetic acid (2 ml) were added at 0° C. under a nitrogen atmosphere and stirred in an ice bath for 2 hours. After the reaction was completed as detected by TLC, the mixture was concentrated, diethyl ether was added, and stirred in the ice bath. White solids were precipitated, filtered and dried to obtain the product (62 mg, yield: 17.27%). $^1$H NMR (400 MHz, DMSO-d6) δ 8.49-8.14 (m, 2H), 7.50-7.16 (m, 3H), 4.63-4.05 (m, 3H), 2.85-2.63 (m, 5H), 2.32-2.23 (m, 1H). HESI: 327.06[M+H]$^+$.

Example 4: Synthesis of (R)-3-mercapto-N—((R)-3-mercapto-1-(((R)-3-mercapto-1-(methylamino)-1-oxopropan-2-yl)amino)-1-oxopropan-2-yl)-2-(methylamino) propanamide trifluoroacetate

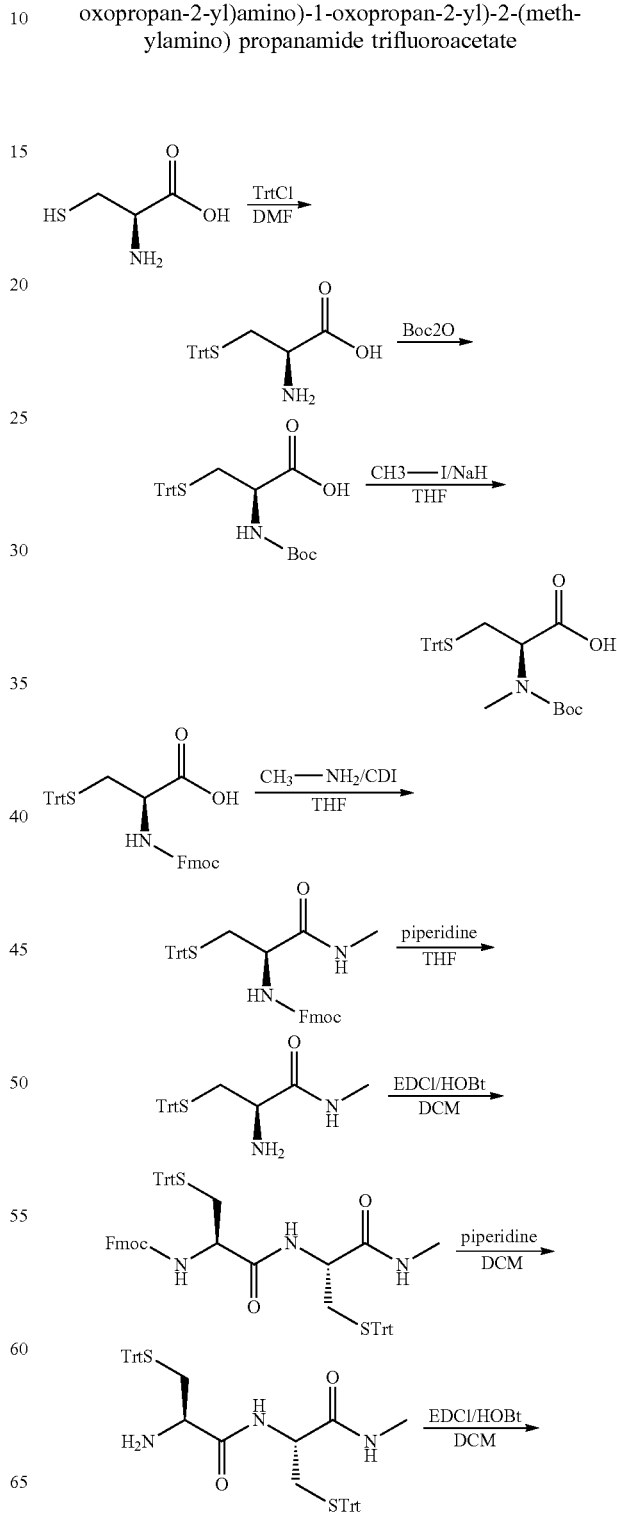

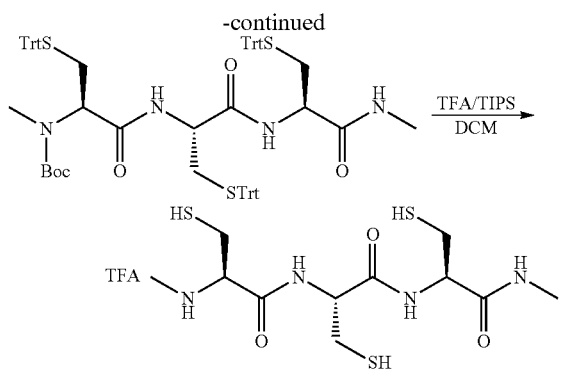

TFA/TIPS
DCM

Step 1: Synthesis of S-trityl-L-cysteine

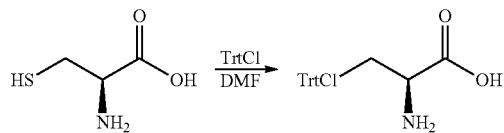

The compound L-cysteine hydrochloride (10 g, 63.45 mmol) was dissolved in N,N-dimethylformamide (120 ml). Triphenylchloromethane (19.46 g, 69.795 mmol) was added, heated to 60-65° C., and reacted for 8 h. After the reaction was completed as detected by TLC, the reaction was cooled to room temperature, and 10% sodium acetate solution (300 ml) was added. White solids were then precipitated and filtered. Filter residue was washed with pure water (300 ml), then washed with acetone (200 ml), and dried to obtain the product as a white solid (17.56 g, yield: 76.15%). $^1$H NMR (400 MHz, DMSO) δ 7.28 (m, 18H), 2.92 (dd, 1H), 2.59 (dd, 1H), 2.41 (dd, 1H).

Step 2: Synthesis of N-(tert-butoxycarbonyl)-S-trityl-L-cysteine

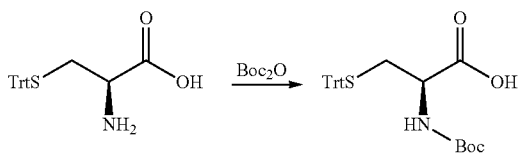

The compound S-trityl-L-cysteine (5 g, 13.76 mmol) was dissolved in a mixture of dioxane (40 ml), water (20 ml) and 1M sodium hydroxide solution (14 ml), and stirred in an ice bath. Boc-anhydride (3.5 ml, 15.14 mmol) was added, then reacted until the mixture was naturally warmed to room temperature, and stirred for 8 hours. After the reaction was completed as detected by TLC, the reaction mixture was concentrated to 20-25 ml. Ethyl acetate was added, and the sodium bisulfate solution was added dropwise under the ice bath while stirring. After pH was adjusted to 2-3, ethyl acetate was used for extraction. The organic layer was washed with a saturated saline, then dried with sodium sulfate, concentrated, and separated by column chromatography (methanol:dichloromethane: 1%-5%) to obtain the product as a white solid (5.5 g, yield: 86.21%). $^1$H NMR (400 MHz, DMSO-d6) δ 7.26 (m, 16H), 3.78 (m, 1H), 2.51 (m, 1H), 2.36 (dd, 1H), 1.4 (s, 9H).

Step 3: Synthesis of N-(tert-butoxycarbonyl)-N-methyl-S-trityl-L-cysteine

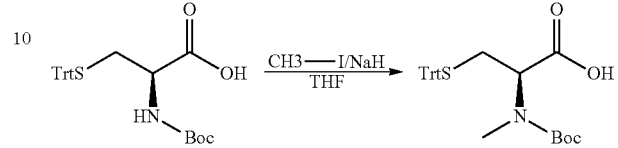

The compound N-(tert-butoxycarbonyl)-S-trityl-L-cysteine (2.1 g, 4.53 mmol) was dissolved in anhydrous tetrahydrofuran (6 ml). Sodium hydride (436 mg, 10.9 mmol) was dissolved in anhydrous tetrahydrofuran (14 ml). The solution of amino acid in tetrahydrofuran was added dropwise to the solution of sodium hydride in tetrahydrofuran in an ice bath. Then, methyl iodide (0.93 ml, 14.95 mmol) was slowly added dropwise and stirred overnight. After the reaction was completed as detected by TLC, phosphate buffer at pH of 7 was added for quenching. pH was adjusted to 6-7 with a saturated ammonium chloride solution, and was extracted with ethyl acetate. The organic layer was washed with a saturated saline, then dried with sodium sulfate, concentrated, and separated by column chromatography (methanol:dichloromethane: 1%-5%) to obtain the product as a white solid (1.3 g, yield: 60.19%). $^1$H NMR (400 MHz, DMSO-d6) δ 7.3 (m, 15H), 3.75 (s, 1H), 2.8 (s, 1H), 2.66 (d, 4H), 1.4 (d, 9H).

Step 4: Synthesis of (9H-fluoren-9-yl) methyl (R)-(1-(methylamino)-1-oxo-3-(tritylthio)propan-2-yl) carbamate

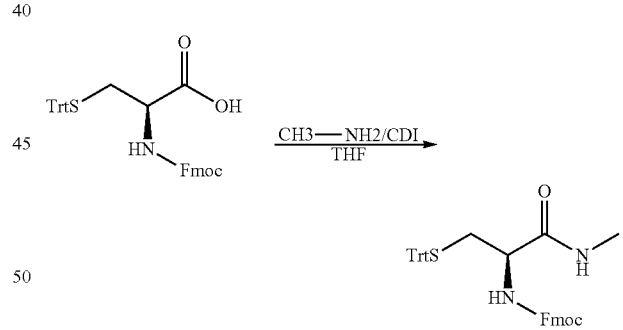

The compound (R)-2-(((9H-fluoren-9-yl)methoxy)carbonyl)amino)-3-(tritylthio) propanoic acid (10 g, 17.07 mmol) was dissolved in tetrahydrofuran (50 ml). N,N'-carbonyldiimidazole (5.59 g, 34.48 mmol) was added at 0-5° C. After stirring for 2 hours under nitrogen atmosphere, methylamine (3.03 ml, 68.28 mmol) was added, and reacted at 0-5° C. for 2 hours. After the reactants were consumed, 2M hydrochloric acid (60 ml) was added for quenching, and the reaction mixture was extracted with dichloromethane. The organic layer was washed with a saturated saline, then dried with sodium sulfate and then concentrated to obtain a crude product. Methanol (20 ml) was added and stirred overnight at room temperature. White solids were precipitated, and filtered to obtain the product in filter residue. The methanol phase was concentrated, and separated by column chromatography (methanol:dichloromethane: 1%-5%) to obtain a white solid (9.44 g, yield: 92.37%). ¹H NMR (400 MHz, DMSO-d6) δ 7.89 (d, 2H), 7.81 (d, 1H), 7.74 (d, 2H), 7.66 (d, 1H), 7.41 (t, 2H), 7.29 (m, 17H), 4.31 (d, 1H), 4.22 (t, 2H), 4.00 (d, 1H), 2.53 (d, 3H), 2.39 (d, 2H).

Step 5: Synthesis of (R)-2-amino-N-methyl-3-(tritylthio) propionamide

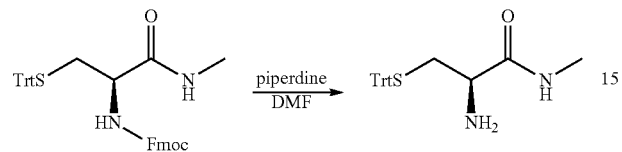

The compound (9H-fluoren-9-yl) methyl (R)-(1-(methylamino)-1-oxo-3-(tritylthio)propan-2-yl) carbamate (2 g, 3.34 mmol) was dissolved in N,N-dimethylformamide (20 ml). Piperidine (0.07 ml, 0.668 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane: 1%-5%) to obtain the product as a yellowish white solid (879 mg, yield: 69.76%). ¹H NMR (400 MHz, DMSO-d6) δ 7.77 (d, 1H), 7.29 (m, 15H), 3.08 (m, 1H), 2.55 (d, 3H), 2.37 (m, 1H), 2.19 (m, 1H), 1.80 (s, 2H).

Step 6: Synthesis of (9H-fluoren-9-yl) methyl ((R)-1-(((R)-1-(methylamino)-1-oxo-3-(tritylthio)propan-2-yl)amino)-1-oxo-3-(tritylthio)propan-2-yl)carbamate

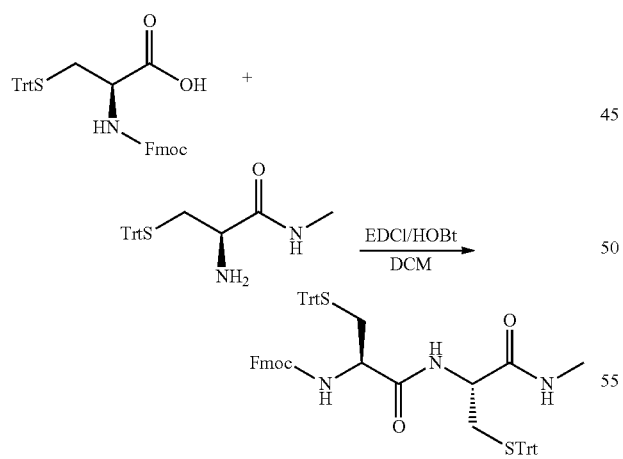

The compound (R)-2-((((9H-fluoren-9-yl)methoxy)carbonyl)amino)-3-(tritylthio) propanoic acid (100 mg, 0.17 mmol) was dissolved in dichloromethane (5 ml). 1-hydroxybenzotriazole (34.5 mg, 0.255 mmol) and EDCI (48.9 mg, 0.255 mmol) were added, and stirred at room temperature for 5 min. (R)-2-amino-N-methyl-3-(tritylthio) propanamide (76.8 mg, 0.204 mmol) was added and reacted at room temperature for 30 minutes. After the reaction was completed as detected by TLC, the mixture was washed with a saturated saline and extracted with dichloromethane. The organic phase was dried with sodium sulfate, then concentrated, and separated by column chromatography (methanol:dichloromethane: 1%-5%) to obtain the product as a white solid (160 mg, yield: 99.68%). ¹H NMR (400 MHz, DMSO-d6) δ 7.89 (d, 2H), 7.71 (m, 4H), 7.40 (m, 2H), 7.38-7.25 (m, 30H), 4.25 (m, 4H), 4.01 (m, 1H), 2.50-2.33 (m, 7H).

Step 7: Synthesis of (R)-2-amino-N—((R)-1-(methylamino)-1-oxo-3-(tritylthio)propan-2-yl)-3-(tritylthio) propionamide

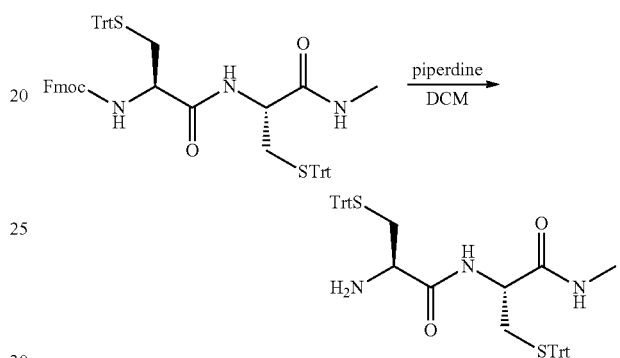

The compound (9H-fluoren-9-yl) methyl ((R)-1-(((R)-1-(methylamino)-1-oxo-3-(tritylthio)propan-2-yl) amino)-1-oxo-3-(tritylthio)propan-2-yl) carbamate (3.6 g, 3.8 mmol) was dissolved in N,N-dimethylformamide (15 ml). Piperidine (0.07 ml, 0.76 mmol) was added and reacted at room temperature for 4 hours. After the reaction was completed as detected by TLC detection, the reaction mixture was washed with a saturated saline and extracted with dichloromethane. The organic phase was dried with sodium sulfate, then concentrated, and separated by column chromatography (methanol:dichloromethane: 1%-5%) to obtain the product as a white solid (1.3 g, yield: 47.44%). ¹H NMR (400 MHz, DMSO-d6) δ 8.12 (s, 1H), 7.83 (d, 1H), 7.27 (m, 30H), 4.25 (s, 1H), 3.29 (m, 2H), 3.20 (s, 1H), 2.65-2.23 (m, 5H).

Step 8: Synthesis of tert-butyl methyl((4R,7R,10R)-3,6,9-trioxo-13,13,13-triphenyl-4,7-bis((tritylthio) methyl)-12-thia-2,5,8-triazatridec-10-yl) carbamate

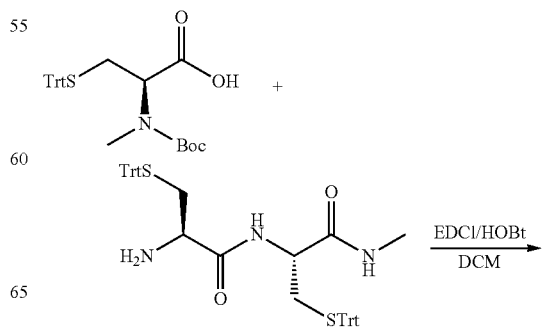

-continued

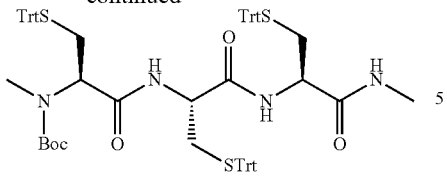

The compound N-(tert-butoxycarbonyl)-N-methyl-S-trityl-L-cysteine (509 mg, 1.07 mmol) was dissolved in dichloromethane (10 ml). 1-hydroxybenzotriazole (218 mg, 1.61 mmol) and EDCI (309 mg, 1.61 mmol) were added, and stirred at room temperature for 5 min. (R)-2-amino-N—((R)-1-(methylamino)-1-oxo-3-(tritylthio)propan-2-yl)-3-(tritylthio) propanamide (924 mg, 1.28 mmol) was added and reacted at room temperature for 30 minutes. After the reaction was completed as detected by TLC, the mixture was washed with a saturated saline and extracted with dichloromethane. The organic phase was dried with sodium sulfate, concentrated, and separated by column chromatography (methanol:dichloromethane: 1%-5%) to obtain the product as a white solid (985 mg, yield: 77.93%). $^1$H NMR (400 MHz, DMSO-d6) δ 8.11 (d, 1H), 7.73 (d, 2H), 7.32-7.21 (m, 45H), 4.25 (m, 3H), 2.62 (m, 1H), 2.49 (m, 6H) 2.47-2.23 (m, 5H), 1.35-1.21 (d, 9H).

Step 9: Synthesis of (R)-3-mercapto-N—((R)-3-mercapto-1-(((R)-3-mercapto-1-(methylamino)-1-oxopropan-2-yl)amino)-1-oxopropan-2-yl)-2-(methylamino) propanamide trifluoroacetate

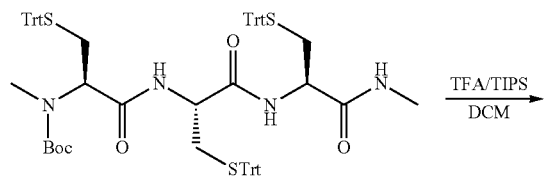

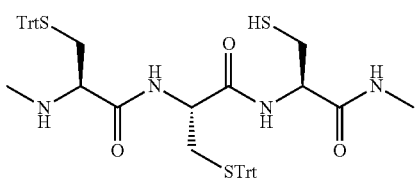

The compound tert-butyl methyl((4R,7R,10R)-3,6,9-trioxo-13,13,13-triphenyl-4,7-bis((tritylthio)methyl)-12-thia-2,5,8-triazatridec-10-yl) carbamate (1.5 g, 1.27 mmol) was dissolved in dichloromethane:trifluoroacetic acid:triisopropylsilane (50:47:3 by volume) (40 ml), stirred at room temperature for 5 min. After the reaction was completed as detected by TLC, the mixture was concentrated, diethyl ether was added, and stirred in an ice bath. White solids were precipitated, filtered and dried to obtain the product (446 mg, yield: 77.77%). $^1$H NMR (400 MHz, MeOD) δ 4.54 (m, 1H), 4.42 (m, 1H), 4.05 (t, J=5.2 Hz, 1H), 3.13 (m, 1H), 2.99 (m, 2H), 2.85 (m, 2H), 2.79 (m, 1H), 2.73 (s, 3H), 2.70 (s, 3H). MS: $C_{11}H_{22}N_4O_3S_3$, the calculated value is 354.51, and the measured value is 355.1, [M+H]$^+$.

Example 5: Synthesis of (S)-2-amino-N—((S)-1-amino-3-mercapto-1-oxopropan-2-yl)-3-mercaptopropanamide trifluoroacetate

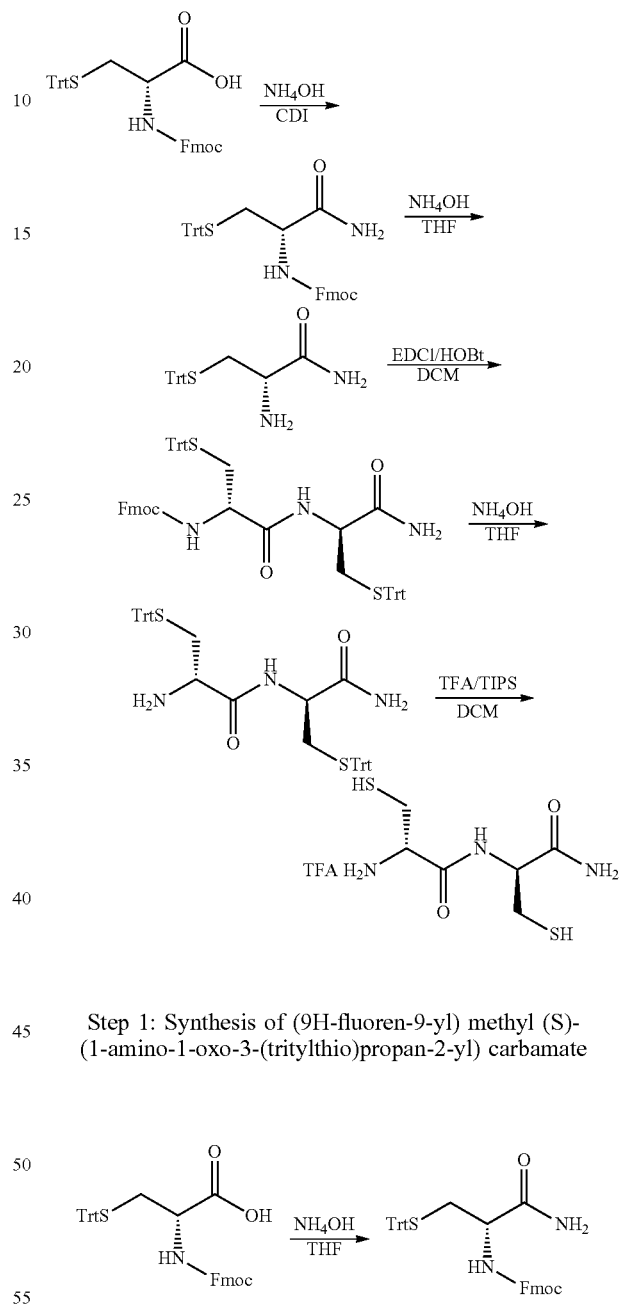

Step 1: Synthesis of (9H-fluoren-9-yl) methyl (S)-(1-amino-1-oxo-3-(tritylthio)propan-2-yl) carbamate

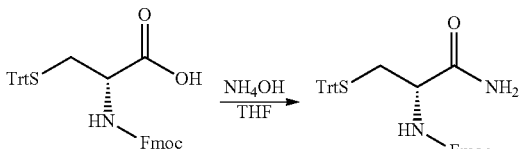

CDI (1.64 g, 10.1 mmol) was dissolved in a double-neck flask of DCM (50 ml) and stirred at room temperature for 2 h under $N_2$ protective conditions. The compound N-(((9H-fluoren-9-yl)methoxy)carbonyl)-S-trityl-D-cysteine (2.93 g, 5 mmol) was added to a reaction flask and stirred for 15 min. After the completion of the reaction, a saturated saline was added for washing (20 ml×3). Anhydrous $Na_2SO_4$ was used to dry the organic phase, and the reaction liquid was concentrated by distillation under reduced pressure. After adding anhydrous methanol (50 ml) and stirring for about 1 h, the product was precipitated and filtered, and the filter cake was repeatedly washed twice to obtain the white crystalline powder (2.2 g, yield: 75.30%). $^1$H NMR (400 MHz, CDCl$_3$) δ 7.73 (m, 2H), 7.54 (d, J=7.6 Hz, 2H), 7.37 (m, 8H), 5.69 (s, 1H), 5.25 (s, 1H), 4.93 (d, J=5.6 Hz 1H), 4.43 (m, 2H), 4.17 (t, J=6.4 Hz, 1H), 3.80 (s, 1H), 2.64 (m, 2H).

Step 2: Synthesis of (S)-2-amino-3-(tritylthio) propionamide

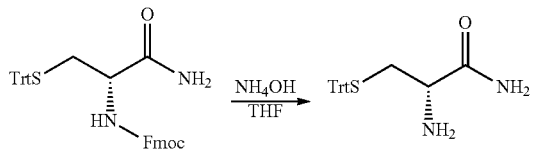

The compound (9H-fluoren-9-yl) methyl (S)-(1-amino-1-oxo-3-(tritylthio)propan-2-yl) carbamate (2.2 g, 3.76 mmol) was dissolved in a single-neck flask of THF (50 ml), NH$_4$OH (25%, 11.6 ml) was added, and stirred at room temperature overnight. After completion of the reaction, the mixture was washed with a saturated saline (30×3 ml) and extracted with EA (30 ml). The organic phases were combined and dried with anhydrous Na$_2$SO$_4$. After concentrating by distillation under reduced pressure, the crude product was separated and purified by silica gel column to obtain a colorless oily product (1.20 g, yield: 88.24%). $^1$H NMR (400 MHz, CDCl$_3$) δ 7.44 (m, 6H), 7.24 (m, 9H), 6.80 (s, 1H), 5.46 (s, 1H), 2.98 (m, 1H), 2.70 (m, 1H), 2.55 (m, 1H).

Step 3: Synthesis of (9H-fluoren-9-yl) methyl ((S)-1-(((S)-1-amino-1-oxo-3-(tritylthio)propan-2-yl) amino)-1-oxo-3-(tritylthio)propan-2-yl) carbamate

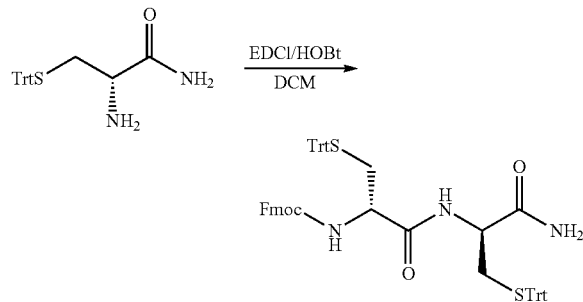

The compound N-(((9H-fluoren-9-yl)methoxy)carbonyl)-S-trityl-D-cysteine (10.33 g, 17.64 mmol) was dissolved in a single-neck flask of DCM (200 ml), EDCI (5.10 g, 26.46 mmol) and HOBT (3.58 g, 26.46 mmol) were added, the compound (S)-2-amino-3-(tritylthio)propanamide (7.0 g, 19.40 mmol) was added, and stirred at room temperature for 20 min. After completion of the reaction, the mixture was washed with a saturated saline (100×3 ml) and extracted with DCM (20 ml). The organic phase was dried with anhydrous Na$_2$SO$_4$. After concentrating by distillation under reduced pressure, the crude product was purified by silica gel column chromatography to obtain a colorless oily product (15.0 g, yield: 91.46%). $^1$H NMR (400 MHz, CDCl$_3$) δ 7.88 (m, 3H), 7.70 (m, 3H), 7.40 (m, 2H), 7.24 (m, 30H), 4.25 (m, 3H), 2.35 (m, 3H).

Step 4: Synthesis of (S)-2-amino-N—((S)-1-amino-1-oxo-3-(tritylthio)propan-2-yl)-3-(tritylthio) propionamide

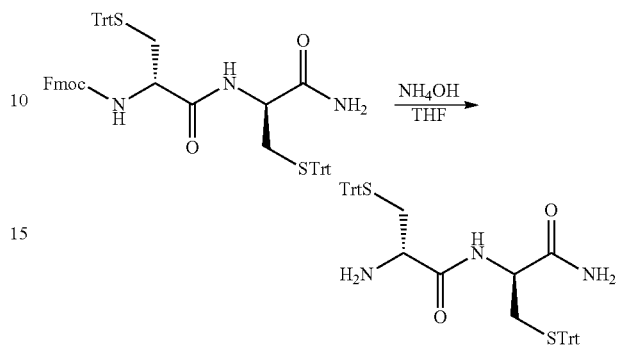

The compound (9H-fluoren-9-yl) methyl ((S)-1-(((S)-1-amino-1-oxo-3-(tritylthio)propan-2-yl)amino)-1-oxo-3-(tritylthio)propan-2-yl) carbamate (3.5 g, 3.76 mmol) was dissolved in a single-neck flask of THF (30 ml), NH$_4$OH (25%, 11.60 ml) was added, and stirred at room temperature overnight. After completion of the reaction, the mixture was washed with a saturated saline (30×3 ml) and extracted with EA (30 ml). The organic phases were combined and dried with anhydrous Na$_2$SO$_4$. After concentrating by distillation under reduced pressure, the crude product was separated and purified by silica gel column to obtain a colorless oily product (1.64 g, yield: 61.65%). $^1$H NMR (400 MHz, CDCl$_3$) δ 7.90 (m, 12H), 7.23 (m, 18H), 6.07 (s, 1H), 5.15 (s, 1H), 3.92 (m, 1H), 2.66 (m, 2H), 2.94 (m, 2H).

Step 5: Synthesis of (S)-2-amino-N—((S)-1-amino-3-mercapto-1-oxopropan-2-yl)-3-mercaptopropanamide trifluoroacetate

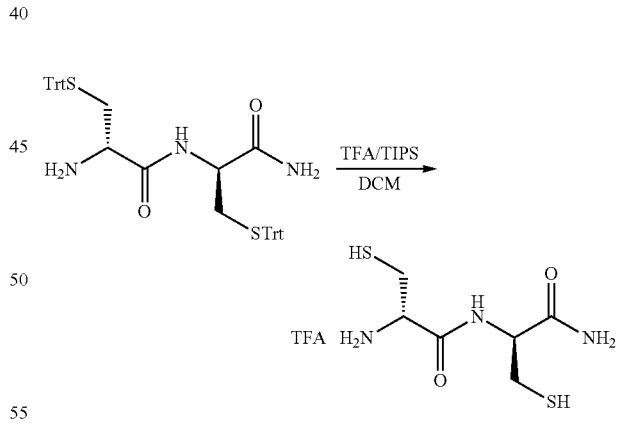

The compound (S)-2-amino-N—((S)-1-amino-1-oxo-3-(tritylthio)propan-2-yl)-3-(tritylthio) propionamide (2.8 g, 3.96 mmol) was dissolved in a single-neck flask of DCM (30 ml), TFA (18 g, 158.4 mmol) and triethyl silicane (2.76 g, 23.8 mmol) were added, and stirred at room temperature for about 30 min. After the completion of reaction, white solids appeared in the reaction liquid concentrated by distillation under reduced pressure, and anhydrous diethyl ether (50 ml×3) was added for stirring and washing, and then filtered to obtain a white-like solid (710 mg, yield: 80%). $^1$H NMR (400 MHz, MeOD) δ 4.50 (m, 1H), 4.10 (t, J=5.6 Hz, 1H), 3.28 (m, 2H), 2.85 (m, 2H). MS: C$_6$H$_{13}$N$_3$O$_2$S$_2$, the calculated value was 223.04, and the measured value was 244.1, [M+H]$^+$.

Example 6: Synthesis of (S)-2-amino-N—((S)-1-(((S)-1-amino-3-mercapto-1-oxopropan-2-yl)amino)-3-mercapto-1-oxopropan-2-yl)-3-mercaptopropionamide

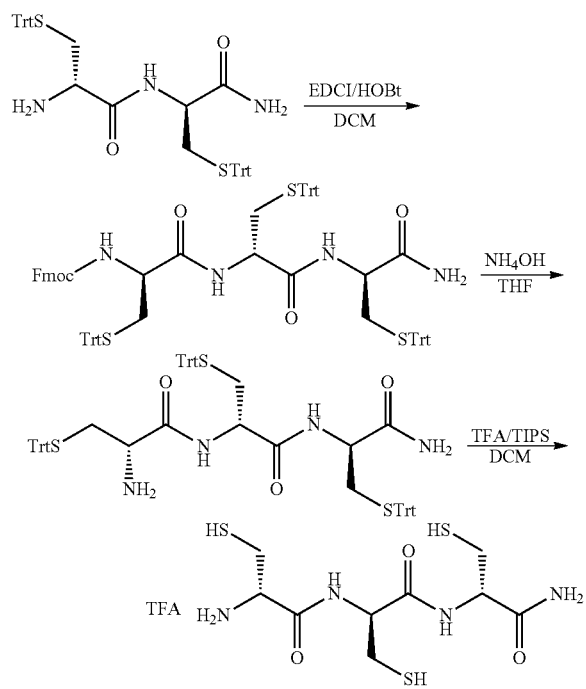

Step 1: Synthesis of (9H-fluoren-9-yl) methyl ((4S, 7S,10S)-4-carbamoyl-6,9-dioxo-1,1,1,13,13,13-hexaphenyl-7-((tritylthio)methyl)-2,12-dithia-5,8-diazatridec-10-yl) carbamate

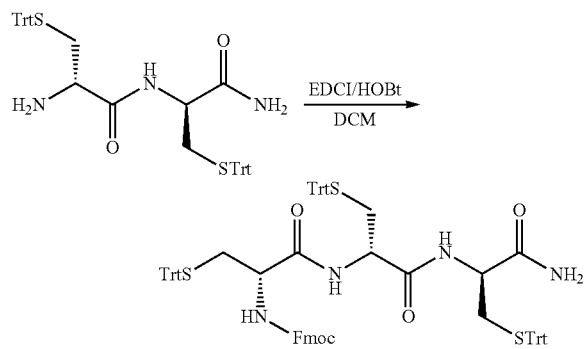

The compound N-(((9H-fluoren-9-yl)methoxy)carbonyl)-S-trityl-D-cysteine (1.24 g, 2.12 mmol) was dissolved in a single-neck flask of DCM (50 ml), EDCI (609.6 mg, 3.18 mmol) and HOBT (429.94 mg, 3.18 mmol) were added, the compound (S)-2-amino-N—((S)-1-amino-1-oxo-3-(tritylthio)propan-2-yl)-3-(tritylthio) propanamide (1.65 g, 2.33 mmol) was added, and stirred at room temperature for 20 min. DCM (20 ml) was added for extraction and saturated saline (20 ml×3) for washing. The organic phase was dried with anhydrous Na$_2$SO$_4$ and then concentrated. The crude product was purified by silica gel column chromatography to obtain a colorless oily product (2.57 g, yield: 92.5%). $^1$H NMR (400 MHz, CDCl$_3$) δ 7.78 (t, J=8.6 Hz, 2H), 7.48 (m, 2H), 7.37 (m, 20H), 7.16 (m, 29H), 6.52 (d, J=8 Hz, 1H), 6.36 (s, 1H), 6.22 (d, J=5.6 Hz, 1H), 4.98 (s, 1H), 4.82 (d, J=5.2 Hz, 1H), 4.43 (m, 1H), 4.22 (m, 1H), 4.10 (m, 2H), 3.91 (m, 2H), 3.52 (m, 1H), 2.61 (m, 5H).

Step 2: Synthesis of (S)-2-amino-N—((S)-1-(((S)-1-amino-1-oxo-3-(tritylthio)propan-2-yl)amino)-1-oxo-3-(tritylthio)propan-2-yl)-3-(tritylthio) propionamide

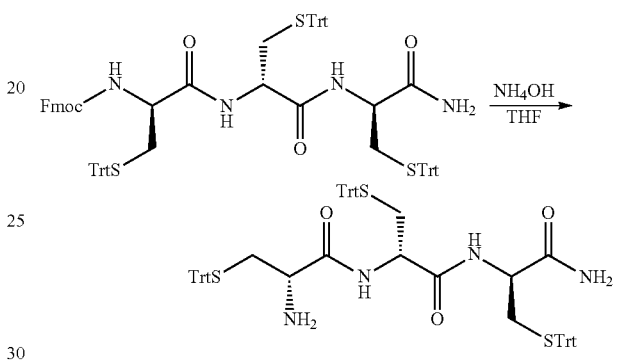

The compound (9H-fluoren-9-yl) methyl ((4S,7S,10S)-4-carbamoyl-6,9-dioxo-1,1,1,13,13,13-hexaphenyl-7-((tritylthio)methyl)-2,12-dithia-5,8-diazatridec-10-yl) carbamate (1.0 g, 0.78 mmol) was dissolved in a single-neck flask of THF (20 ml), NH$_4$OH (25%, 2.40 ml) was added, and stirred at room temperature overnight. After completion of the reaction, the mixture was washed with a saturated saline (10×3 ml) and extracted with EA (20 ml). The organic phases were combined and dried with anhydrous Na$_2$SO$_4$. After concentrating by distillation under reduced pressure, the crude product was separated and purified by silica gel column to obtain a colorless oily product (583.37 mg, yield: 71.0%). $^1$H NMR (400 MHz, CDCl$_3$) δ 7.22 (m, 45H), 6.52 (d, J=8 Hz, 1H), 6.36 (s, 1H), 6.22 (d, J=5.6 Hz, 1H), 4.99 (s, 1H), 4.82 (d, J=5.2 Hz, 1H), 4.22 (m, 1H), 3.90 (m, 2H), 3.52 (m, 1H), 2.60 (m, 5H).

Step 3: Synthesis of (S)-2-amino-N—((S)-1-(((S)-1-amino-3-mercapto-1-oxopropan-2-yl)amino)-3-mercapto-1-oxopropan-2-yl)-3-mercaptopropionamide

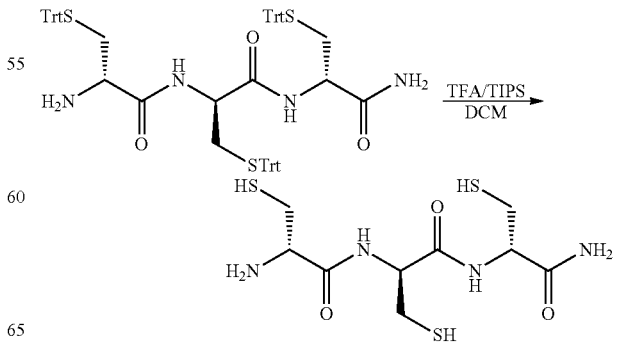

The compound (S)-2-amino-N—((S)-1-(((S)-1-amino-1-oxo-3-(tritylthio)propan-2-yl)amino)-1-oxo-3-(tritylthio) propan-2-yl)-3-(tritylthio) propionamide (1.20 g, 1.14 mmol) was dissolved in a single-neck flask of DCM (30 ml), TFA (5.20 g, 45.56 mmol) and triethyl silicane (795.36 mg, 6.84 mmol) were added, and stirred at room temperature for about 30 min. After the completion of reaction, white solids appeared in the reaction liquid concentrated by distillation under reduced pressure, and anhydrous diethyl ether (50 ml) was added for stirring and washing, and then filtered and repeatedly washed with anhydrous diethyl ether 3 times to obtain the white-like solids (192.78 mg, yield: 51.80%). $^1$H NMR (400 MHz, MeOD) δ 4.54 (m, 1H), 4.42 (m, 1H), 4.05 (t, J=5.2 Hz, 1H), 3.13 (m, 1H), 2.99 (m, 2H), 2.85 (m, 2H), 2.79 (m, 1H). MS: $C_9H_{18}N_4O_3S_3$, the calculated value was 326.05, and the measured value was 327.1, [M+H]$^+$.

Example 7: Synthesis of (S)-3-mercapto-N—((S)-3-mercapto-1-(methylamino)-1-oxopropan-2-yl)-2-(methylamino) propionamide

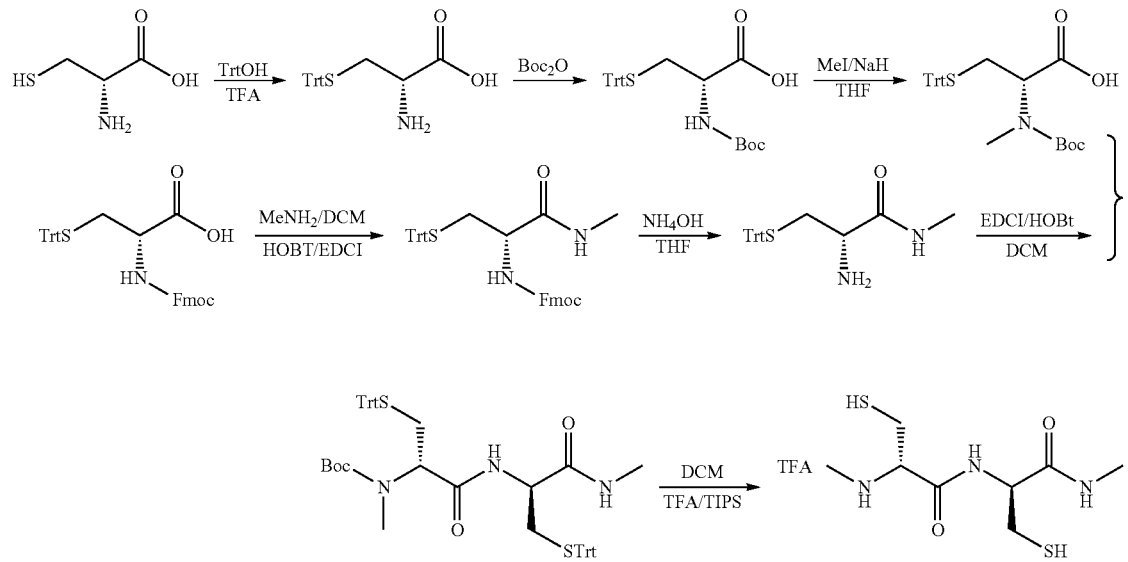

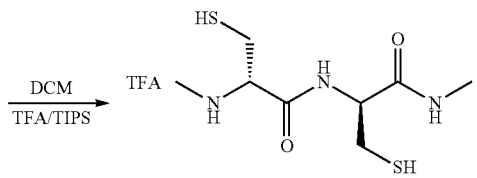

Step 1: Synthesis of S-trityl-D-cysteine:

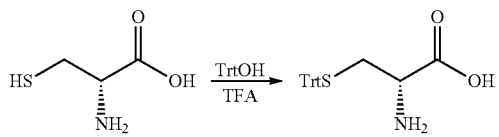

The compound D-cysteine (242.30 mg, 2.0 mmol) was added to a single-neck flask, TFA (4 ml) was added, and stirred at room temperature. Triphenylmethanol (520.68 mg, 2.0 mmol) was added, stirred at room temperature for 2 h, then cooled to 0° C. Anhydrous diethyl ether (30 ml) was added, and a 4 N aqueous NaOH solution was added dropwise with stirring to a pH of about 4-5. A 10% saturated aqueous solution of sodium acetate was added to a pH of about 5-6 and filtered. The filter cake was washed with anhydrous diethyl ether (30 ml×2) to obtain a white powdery product (566.4 mg, yield: 77.90%). $^1$H NMR (400 MHz, DMSO-d6) δ 4.45 (m, 1H), 7.21 (m, 3H), 2.90 (m, 1H), 2.52 (m, 1H), 2.26 (t, J=10.8 Hz, 1H), 1.82 (s, 1H).

Step 2: Synthesis of N-(tert-butoxycarbonyl)-S-trityl-D-cysteine

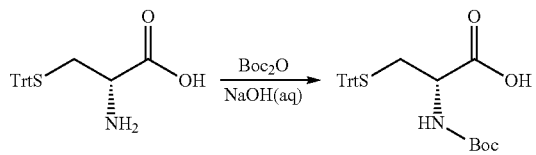

The compound S-trityl-D-cysteine (3.63 g, 10 mmol) was added to a single-neck flask with 2N NaOH (aq) (70 ml), Boc$_2$O (3.43 g, 15.7 mmol) was added, and stirred at room temperature overnight. The reaction liquid was acidified with HCl (aq) to a pH value of about 2, extracted with DCM (20 ml×3), and washed with a saturated saline (20 ml×3). The organic phases were combined, dried with anhydrous Na$_2$SO$_4$, concentrated by distillation under reduced pressure and purified by flash column chromatography to obtain a colorless oily product (4.10 g, yield: 88.40%). $^1$H NMR (400 MHz, CDCl$_3$) δ 7.39 (m, 6H), 7.25 (m, 9H), 4.9 (d, J=7.6 Hz, 1H), 4.10 (m, 1H), 2.65 (d, J=4.4 Hz, 2H), 1.42 (s, 9H).

Step 3: Synthesis of N-(tert-butoxycarbonyl)-N-methyl-S-trityl-D-cysteine

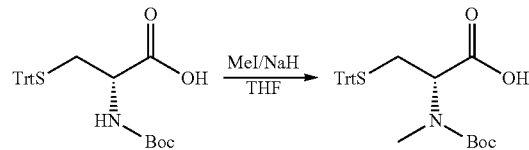

Under the condition of $N_2$ protection, NaH (60%, 1.035 g, 25.88 mmol) was dissolved in a three-neck flask of anhydrous THF (20 ml), and the solution (20 ml) of the compound N-(tert-butoxycarbonyl)-S-trityl-D-cysteine (4.0 g, 8.63 mmol) in anhydrous THF was added dropwise at 0° C. After stirring for 5 min, iodomethane (9.8 g, 69.03 mmol) was added dropwise, and stirred at 0° C. for 1 h and then stirred at room temperature overnight. After completion of the reaction, a phosphate buffer solution (50 ml) with pH=7 was added for quenching reaction, and EA (20 ml) was added for extraction. The mixture was washed with a saturated saline (20 ml×3). The organic phases were combined and dried with anhydrous $Na_2SO_4$. The crude product was separated and purified by silica gel column chromatography to obtain a colorless oily product (3.52 g, yield: 85.44%). $^1$H NMR (400 MHz, $CDCl_3$) δ 7.41 (m, 6H), 7.25 (m, 9H), 3.85 (m, 0.5H), 2.63 (m, 0.5H), 2.79 (m, 1H), 2.65 (d, J=14 Hz, 4H), 1.34 (d, J=10 Hz, 9H).

Step 4: Synthesis of (9H-fluoren-9-yl) methyl (S)-(1-(methylamino)-1-oxo-3-(tritylthio)propan-2-yl) carbamate

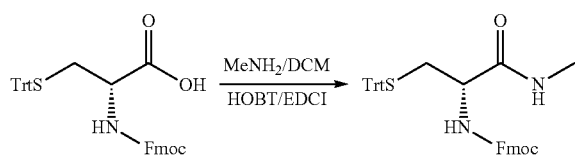

The compound N-(((9H-fluoren-9-yl)methoxy)carbonyl)-S-trityl-D-cysteine (11.75 g, 20 mmol) was dissolved in a single-neck flask of DCM (200 ml), and EDCI (5.75 g, 30 mmol) and HOBT (4.05 g, 30 mmol) were added. The THF solution of methylamine (2.0 mol/L, 15 ml) was added dropwise, stirred at room temperature for 20 min, extracted with DCM (50 ml), washed with a saturated saline (100×3 ml), and dried with anhydrous $Na_2SO_4$. After concentrating by distillation under reduced pressure, anhydrous methanol (200 ml) was added and stirred at room temperature for about 1 h, and filtered to obtain white solids, which were washed repeatedly three times with anhydrous methanol to obtain a white solid (10.84 g, yield: 90.64%). $^1$H NMR (400 MHz, $CDCl_3$) δ 7.73 (t, J=6.6 Hz, 2H), 7.54 (d, J=6.8 Hz, 2H), 7.36 (m, 8H), 7.23 (m, 11H), 5.73 (s, 1H), 4.94 (d, J=6.8 Hz, 1H), 4.39 (d, J=6.4 Hz, 2H), 4.16 (t, J=6.6 Hz, 1H), 3.78 (m, 1H), 2.69 (d, J=4.4 Hz, 3H), 2.62 (m, 2H).

Step 5: Synthesis of (S)-2-amino-N-methyl-3-(tritylthio) propionamide

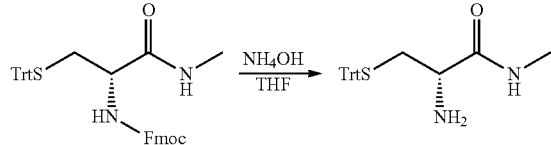

The compound (9H-fluoren-9-yl) methyl (S)-(1-(methylamino)-1-oxo-3-(tritylthio)propan-2-yl) carbamate (10.84 g, 18.10 mmol) was dissolved in a single-neck flask of THF (100 ml), $NH_4OH$ (25%, 28 ml) was added, and stirred at room temperature overnight. After completion of the reaction, the mixture was washed with a saturated saline (30×3 ml) and extracted with EA (30 ml). The organic phases were combined and dried with anhydrous $Na_2SO_4$. After concentrating by distillation under reduced pressure, PE(100 ml) was added and stirred at room temperature for about 1 h, and filtered to obtain white-like crystals, which were washed repeatedly 3 times with PE to obtain a white solid (6.8 g, yield: 99.7%). $^1$H NMR (400 MHz, $CDCl_3$) δ 7.42 (m, 6H), 7.23 (m, 9H), 6.96 (s, 1H), 3.00 (m, 1H), 2.74 (m, 1H), 2.70 (d, J=4.8 Hz, 3H), 2.50 (m, 1H).

Step 6: Synthesis of tert-butyl methyl ((S)-1-(((S)-1-(methylamino)-1-oxo-3-(tritylthio)propan-2-yl) amino)-1-oxo-3-(tritylthio)propan-2-yl) carbamate

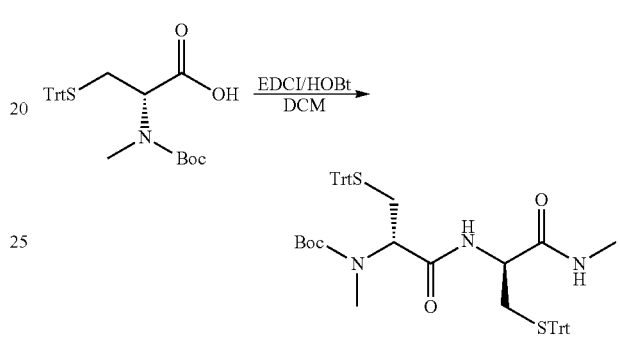

The compound N-(tert-butoxycarbonyl)-N-methyl-S-trityl-D-cysteine (3.52 g, 7.37 mmol) was dissolved in a single-neck flask of DCM (80 ml), EDCI (2.12 g, 11.1 mmol) and HOBT (1.49 g, 11.1 mmol) were added, and the compound (S)-2-amino-N-methyl-3-(tritylthio) propanamide (3.05 g, 8.1 mmol) was added and stirred at room temperature for 20 min. After completion of the reaction, the mixture was washed with a saturated saline (30 ml×3) and extracted with DCM (30 ml). The organic phase was dried with anhydrous $Na_2SO_4$. After concentrating by distillation under reduced pressure, the crude product was purified by silica gel column chromatography to obtain a colorless oily product (5.58 g, yield: 90.58%). $^1$H NMR (400 MHz, $CDCl_3$) δ 7.32 (m, 30H), 6.30 (s, 1H), 6.16 (s, 1H), 3.94 (m, 2H), 2.70 (m, 1H), 2.63 (s, 3H), 2.57 (s, 3H), 2.50 (m, 2H), 2.39 (m, 1H), 1.38 (s, 9H).

Step 7: Synthesis of (S)-3-mercapto-N—((S)-3-mercapto-1-(methylamino)-1-oxopropan-2-yl)-2-(methylamino) propionamide

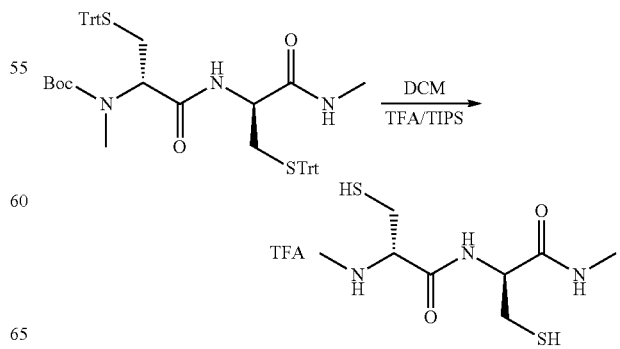

The compound tert-butyl methyl ((S)-1-(((S)-1-(methylamino)-1-oxo-3-(tritylthio)propan-2-yl)amino)-1-oxo-3-(tritylthio)propan-2-yl) carbamate (745.7 mg, 0.89 mmol) was dissolved in a single-neck flask of DCM (10 ml), TFA (5.10 g, 44.6 mmol) and triethyl silicane (622.33 mg, 5.352 mmol) were added, and stirred at room temperature for about 30 min. After the completion of reaction, white solids appeared in the reaction liquid concentrated by distillation under reduced pressure, and anhydrous diethyl ether (20 ml) was added for stirring and washing, and then filtered and repeatedly washed 3 times to obtain a white powdery solid (215.70 mg, yield: 96.21%). $^1$H NMR (400 MHz, MeOD) δ 4.45 (m, 1H), 4.05 (t, J=5.4 Hz, 1H), 3.29 (m, 2H), 3.10 (m, 2H), 2.73 (s, 3H), 2.70 (s, 3H). MS: $C_8H_{17}N_3O_2S_2$, the calculated value was 251.08, and the measured value was 252.1, $[M+H]^+$.

Example 8: Synthesis of (S)-3-mercapto-N—((S)-3-mercapto-1-(((S)-3-mercapto-1-(methylamino)-1-oxopropan-2-yl)amino)-1-oxopropan-2-yl)-2-(methylamino) propanamide

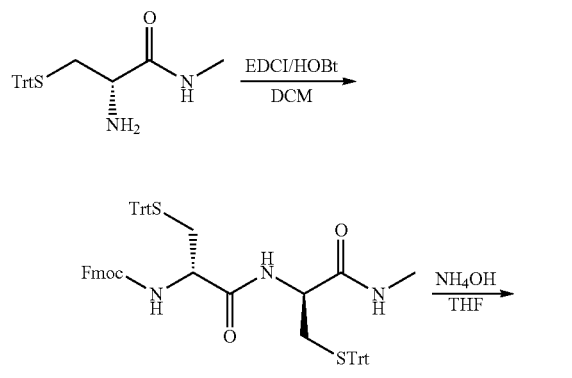

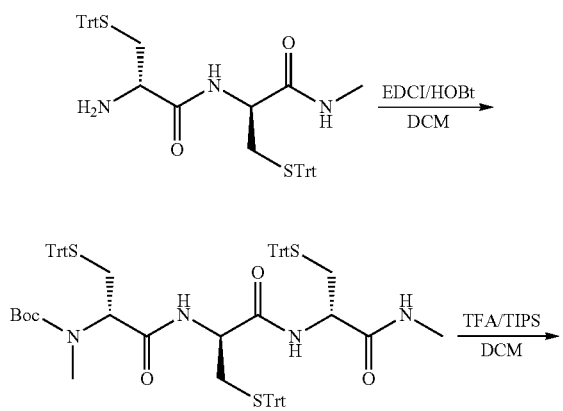

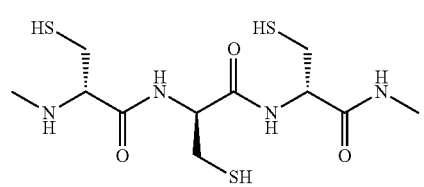

Step 1: Synthesis of (9H-fluoren-9-yl) methyl ((S)-1-(((S)-1-(methylamino)-1-oxo-3-(tritylthio)propan-2-yl)amino)-1-oxo-3-(tritylthio)propan-2-yl) carbamate

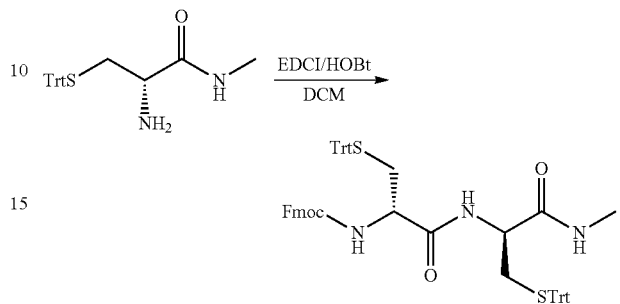

The compound N-(((9H-fluoren-9-yl)methoxy)carbonyl)-S-trityl-D-cysteine (5.63 g, 9.6 mmol) was dissolved in a single-neck flask of DCM (150 ml), EDCI (2.76 g, 14.4 mmol) and HOBT (1.95 g, 14.4 mmol) were added, and the compound (S)-2-amino-N-methyl-3-(tritylthio)propanamide (3.80 mg, 10.1 mmol) was added, and stirred at room temperature for 20 min. After the completion of the reaction, a saturated saline was added for washing (30 ml×3) and extracted with DCM (30 ml). Anhydrous $Na_2SO_4$ was used to dry organic phase, and the reaction liquid was concentrated by distillation under reduced pressure to form solid. PE (50 ml×2) was added and stirred at room temperature for 20 mim for filtration. The filter cake was stirred by adding anhydrous methanol (50 ml×3) at room temperature for 20 min and filtered to obtain white crystalline powder (8.42 g, yield: 92.8%) which was directly used for the next step.

Step 2: Synthesis of (S)-2-amino-N—((S)-1-(methylamino)-1-oxo-3-(tritylthio)propan-2-yl)-3-(tritylthio) propionamide

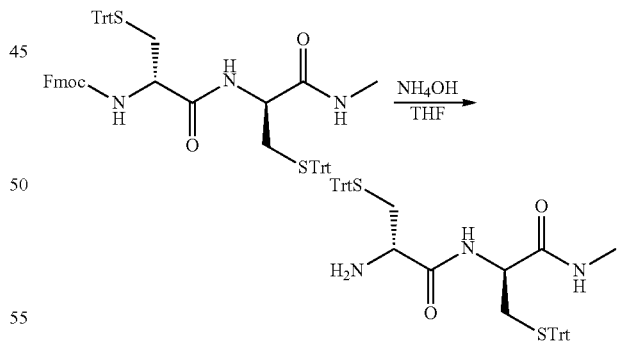

The compound (9H-fluoren-9-yl) methyl ((S)-1-(((S)-1-(methylamino)-1-oxo-3-(tritylthio)propan-2-yl)amino)-1-oxo-3-(tritylthio)propan-2-yl) carbamate (8.42 g, 8.92 mmol) was dissolved in a single-neck flask of THF (100 ml), $NH_4OH$ (25%, 27.5 ml) was added, and stirred at room temperature overnight. After completion of the reaction, the mixture was washed with a saturated saline (30×3 ml) and extracted with EA (30 ml). The organic phases were combined and dried with anhydrous $Na_2SO_4$. After concentrating by distillation under reduced pressure, PE (50 ml×2) was added and stirred at room temperature for about 1 h. After filtration, white solids (5.95 g, yield: 92.4%) were obtained and directly used for the next step.

Step 3: Synthesis of tert-butyl methyl((4S,7S,10S)-3,6,9-trioxo-13,13,13-triphenyl-4,7-bis((tritylthio)methyl)-12-thia-2,5,8-triazatridec-10-yl) carbamate

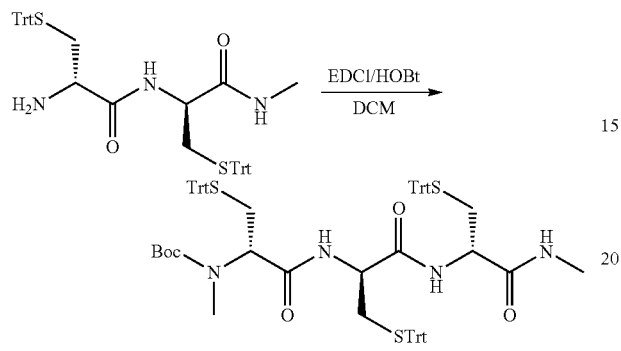

The compound N-(tert-butoxycarbonyl)-N-methyl-S-trityl-D-cysteine (1.97 g, 4.12 mmol) was dissolved in a single-neck flask of DCM (100 ml), EDCI (1.19 g, 6.19 mmol) and HOBT (836.9 mg, 6.19 mmol) were added, and the compound (S)-2-amino-N—((S)-1-(methylamino)-1-oxo-3-(tritylthio)propan-2-yl)-3-(tritylthio)propionamide (3.28 g, 4.54 mmol) was added and stirred at room temperature for 20 min. After completion of the reaction, the mixture was washed with a saturated saline (30 ml×3) and extracted with DCM (20 ml). The organic phase was dried with anhydrous Na$_2$SO$_4$. After concentrating by distillation under reduced pressure, the crude product was purified by silica gel column chromatography to obtain a white-like oily product (2.12 g, yield: 43.2%). $^1$H NMR (400 MHz, CDCl$_3$) δ 7.28 (m, 45H), 6.64 (s, 1H), 5.75 (s, 1H), 4.18 (s, 2H), 3.80 (m, 1H), 3.20 (m, 1H), 2.79 (m, 1H), 2.65 (m, 1H), 2.63 (m, 4H), 2.52 (m, 1H), 2.36 (m, 4H), 2.24 (m, 1H), 1.37 (s, 9H).

Step 4: Synthesis of (S)-3-mercapto-N—((S)-3-mercapto-1-(((S)-3-mercapto-1-(methylamino)-1-oxopropan-2-yl)amino)-1-oxopropan-2-yl)-2-(methylamino) propanamide

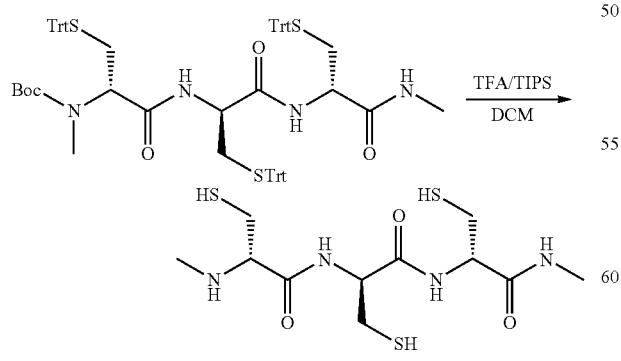

The compound methyl((4S,7S,10S)-3,6,9-trioxo-13,13,13-triphenyl-4,7-bis((tritylthio)methyl)-12-thia-2,5,8-triazatridec-10-yl) carbamate (1.0 g, 0.85 mmol) was dissolved in a single-neck flask of DCM (40 ml), TFA (3.86 g, 33.85 mmol) and triethylsilane (593 mg, 5.1 mmol) were added, and stirred at room temperature for about 30 min. After the completion of reaction, white solids appeared in the reaction liquid concentrated by distillation under reduced pressure, and anhydrous diethyl ether (50 ml×3) was added for stirring and washing, and then filtered to obtain a white solid powder (290 mg, yield: 96.67%). $^1$H NMR (400 MHz, MeOD) δ4.54 (m, 1H), 4.42 (m, 1H), 4.05 (t, J=5.2 Hz, 1H), 3.13 (m, 1H), 2.99 (m, 2H), 2.85 (m, 2H), 2.79 (m, 1H), 2.73 (s, 3H), 2.70 (s, 3H). MS: C$_{11}$H$_{22}$N$_4$O$_3$S$_3$, the calculated value was 354.09, and the measured value was 355.1, [M+H]$^+$.

Example 9: Synthesis of (R)-2-amino-3-(((R)-1-amino-3-mercaptopropan-2-yl)amino)propane-1-thiol hydrochloride

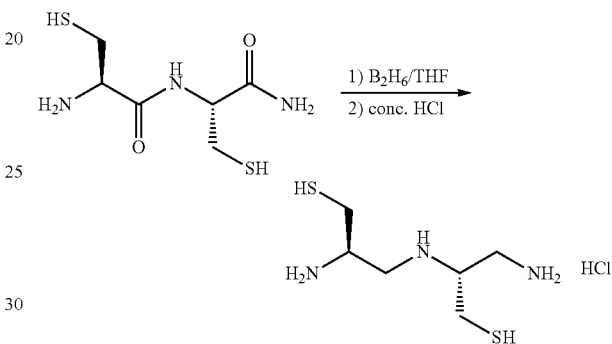

The compound (R)-2-amino-N—((R)-1-amino-3-mercapto-1-oxopropan-2-yl)-3-mercaptopropanamide (0.5 g, 2.24 mmol) (prepared in Example 1) was added to a reaction flask, anhydrous THF (20 ml) was added, and cooled with an ice-salt bath. A borane tetrahydrofuran solution (1M, 13.44 ml, 13.44 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (1 ml) was added for quenching the reaction. After stirring for 30 minutes, concentrated hydrochloric acid (12N, 0.95 ml, 11.42 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (360 mg, yield: 52.6%). $^1$H NMR (400 MHz, D$_2$O) δ 3.18 (m, 2H), 2.91-2.52 (m, 8H). MS (ES+) m/z 196.35 [M+H]$^+$.

Example 10: Synthesis of (R)-2-(((R)-3-mercapto-2-(methylamino)propyl)amino)-3-(methylamino) propane-1-thiol hydrochloride

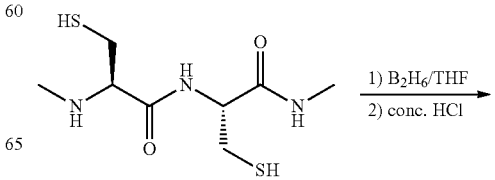

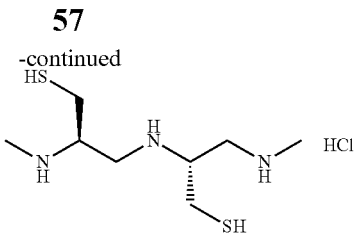

The compound (R)-3-mercapto-N—((R)-3-mercapto-1-(methylamino)-1-oxopropan-2-yl)-2-(methylamino) propanamide (2.0 g, 7.96 mmol) (prepared in Example 2) was added to a reaction flask, anhydrous THF (50 ml) was added, and cooled with an ice-salt bath. A borane tetrahydrofuran solution (1M, 47.76 ml, 47.76 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (1 ml) was added for quenching the reaction. After stirring for 30 minutes, concentrated hydrochloric acid (12N, 3.38 ml, 40.60 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (2.2 g, yield: 84.39%). $^1$H NMR (400 MHz, D$_2$O) δ 3.28 (s, 6H), 3.17 (m, 2H), 2.77-2.75 (m, 4H), 2.52-2.50 (m, 4H). MS (ES+) m/z 224.40 [M+H]$^+$.

Example 11: Synthesis of (R)-2-amino-3-(((R)-1-(((R)-1-amino-3-mercaptopropan-2-yl)amino)-3-mercaptopropan-2-yl)amino)propane-1-thiol hydrochloride

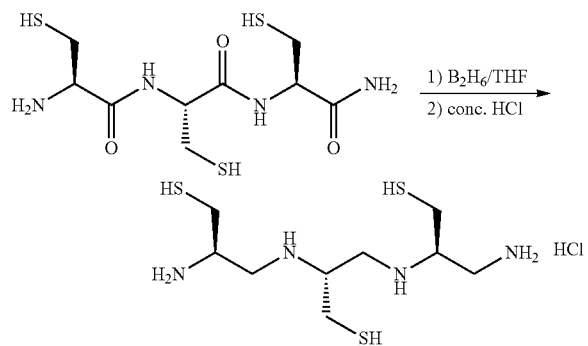

The compound (R)-2-amino-N—((R)-1-((R)-1-amino-3-mercapto-1-oxopropan-2-ylamino)-3-mercapto-1-oxopropan-2-yl)-3-mercaptopropionamide (2.5 g, 7.66 mmol) (prepared in Example 3) was added to a reaction flask, anhydrous THF (50 ml) was added, and cooled with an ice-salt bath. A borane tetrahydrofuran solution (1M, 68.94 ml, 68.94 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (3 ml) was added for quenching the reaction. After stirring for 30 minutes, concentrated hydrochloric acid (12N, 4.7 ml, 57.45 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (2.42 g, yield: 73.44%). $^1$H NMR (400 MHz, D$_2$O) δ 3.17 (m, 3H), 2.92-2.52 (m, 12H). MS (ES+) m/z 285.51 [M+H]$^+$.

Example 12: Synthesis of (R)-2-((R)-3-mercapto-2-((R)-3-mercapto-2-(methylamino)propylamine)propylamino)-3-(methylamino)propane-1-thiol hydrochloride

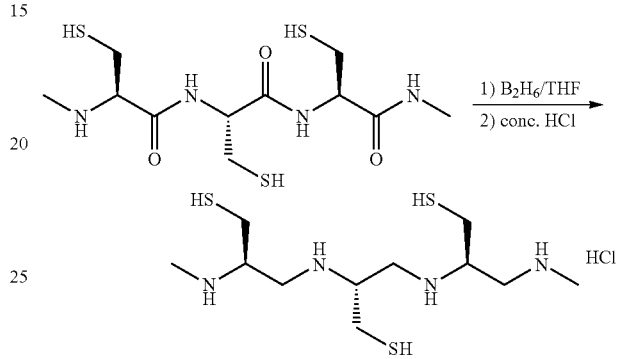

The compound (R)-3-mercapto-N—((R)-3-mercapto-1-((R)-3-mercapto-1-(methylamino)-1-oxopropan-2-ylamino)-1-oxopropan-2-yl)-2-(methylamino) propanamide (1.5 g, 4.59 mmol) (prepared in Example 4) was added to a reaction flask, anhydrous THF (20 ml) was added, and cooled with an ice-salt bath. A borane tetrahydrofuran solution (1M, 41.31 ml, 41.31 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (1 ml) was added for quenching the reaction. After stirring for 30 minutes, concentrated hydrochloric acid (12N, 1.9 ml, 22.8 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (2.1 g, yield: 69.65%). $^1$H NMR (400 MHz, D$_2$O) δ 3.26 (s, 6H), 3.17 (m, 3H), 2.77-2.75 (m, 6H), 2.52-2.50 (m, 6H). MS (ES+) m/z 327.55 [M+H]$^+$.

Example 13: Synthesis of (S)-2-amino-3-(((S)-1-amino-3-mercaptopropan-2-yl)amino)propane-1-thiol hydrochloride

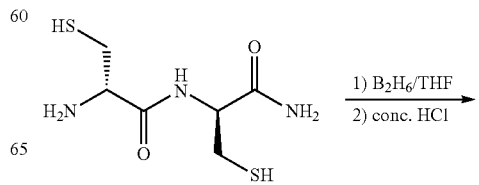

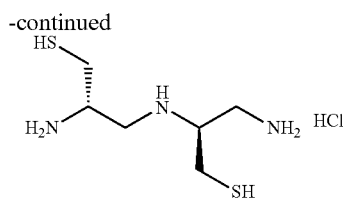

The compound (S)-2-amino-N—((S)-1-amino-3-mercapto-1-oxopropan-2-yl)-3-mercaptopropanamide (1.0 g, 4.48 mmol) (prepared in Example 5) was added to a reaction flask, anhydrous THF (20 ml) was added, and cooled with an ice-salt bath. A borane tetrahydrofuran solution (1M, 26.88 ml, 26.88 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (1 ml) was added for quenching the reaction. After stirring for 30 minutes, concentrated hydrochloric acid (12N, 1.90 ml, 22.84 mmol) was added and heated to 80° C. for 1 hour. After the reaction was completed, the mixture was cooled to room temperature and concentrated. Diethyl ether (10 ml) was added to the solids obtained and stirred for 1 h, filtered, washed with diethyl ether, and dried to obtain the hydrochlorinated target compound as a white solid (780 mg, yield: 57.16%). $^1$H NMR (400 MHz, D$_2$O) δ 3.18 (m, 2H), 2.91-2.52 (m, 8H). MS (ES+) m/z 196.35 [M+H]$^+$.

Example 14: Synthesis of (S)-2-(((S)-3-mercapto-2-(methylamino)propyl)amino)-3-(methylamino)propane-1-thiol hydrochloride

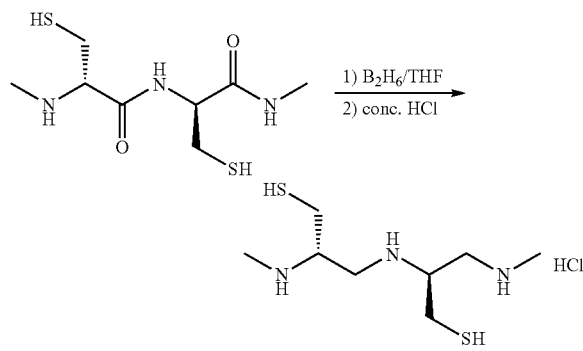

The compound (S)-3-mercapto-N—((S)-3-mercapto-1-(methylamino)-1-oxopropan-2-yl)-2-(methylamino) propanamide (1.0 g, 3.98 mmol) (prepared in Example 7) was added to a reaction flask, anhydrous THF (25 ml) was added, and cooled with an ice-salt bath. A borane tetrahydrofuran solution (1M, 23.88 ml, 23.88 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (1 ml) was added for quenching the reaction. After stirring for 30 minutes, concentrated hydrochloric acid (12N, 1.69 ml, 20.30 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (683 mg, yield: 56.26%). $^1$H NMR (400 MHz, D$_2$O) δ 3.28 (s, 6H), 3.17 (m, 2H), 2.77-2.75 (m, 4H), 2.52-2.50 (m, 4H). MS (ES+) m/z 224.40 [M+H]$^+$.

Example 15: Synthesis of (S)-2-amino-3-(((S)-1-(((R)-1-amino-3-mercaptopropan-2-yl)amino)-3-mercaptopropan-2-yl)amino)propane-1-thiol hydrochloride

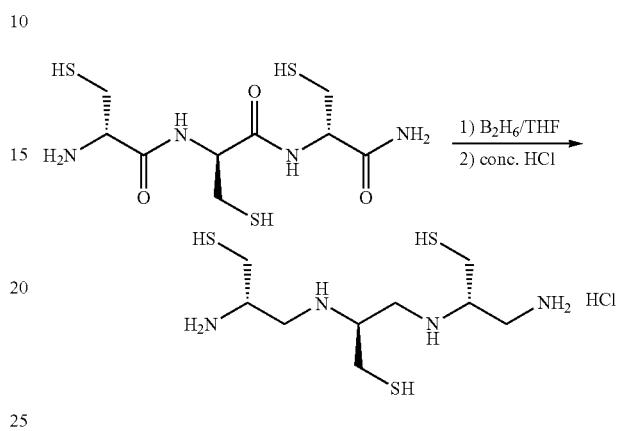

The compound (S)-2-amino-N—((S)-1-((R)-1-amino-3-mercapto-1-oxopropan-2-ylamino)-3-mercapto-1-oxopropan-2-yl)-3-mercaptopropionamide (1.0 g, 3.06 mmol) (prepared in Example 6) was added to a reaction flask, anhydrous THF (10 ml) was added, and cooled with an ice-salt bath. A borane tetrahydrofuran solution (1M, 18.36 ml, 18.36 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (3 ml) was added for quenching the reaction. After stirring for 30 minutes, concentrated hydrochloric acid (12N, 1.3 ml, 15.61 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (760 mg, yield: 63.11%). $^1$H NMR (400 MHz, D$_2$O) δ 3.17 (m, 3H), 2.92-2.52 (m, 12H). MS (ES+) m/z 285.51 [M+H]$^+$.

Example 16: Synthesis of (S)-2-((S)-3-mercapto-2-((S)-3-mercapto-2-(methylamino)propylamine)propylamino)-3-(methylamino)propane-1-thiol hydrochloride

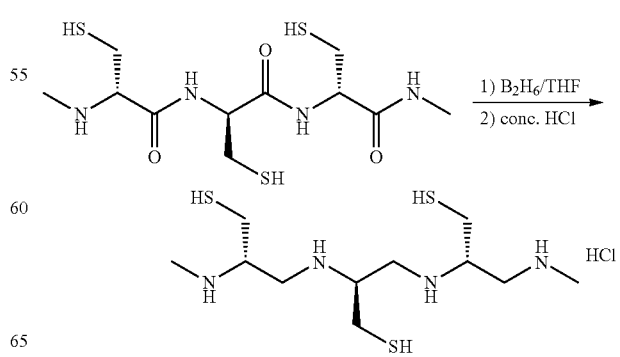

The compound (S)-3-mercapto-N—((S)-3-mercapto-1-((S)-3-mercapto-1-(methylamino)-1-oxopropan-2-ylamino)-1-oxopropan-2-yl)-2-(methylamino) propanamide (1.0 g, 2.82 mmol) (prepared in Example 8) was added to a reaction flask, anhydrous THF (10 ml) was added, and cooled with an ice-salt bath. A borane tetrahydrofuran solution (1M, 16.92 ml, 16.92 mmol) was added dropwise under a nitrogen atmosphere. After the dropwise addition was completed, the mixture was stirred at room temperature for 1 hour and heated to reflux for 18 hours. After the reaction was completed as detected by TLC, the mixture was cooled to 0° C., and methanol (1 ml) was added for quenching the reaction. After stirring for 30 minutes, concentrated hydrochloric acid (12N, 1.20 ml, 14.38 mmol) was added and heated to 80° C. for 1 hour. After the reaction was completed, the mixture was cooled to room temperature and concentrated. Diethyl ether (5 ml) was added to the solids obtained and stirred for 1 h, filtered, washed with diethyl ether, and dried to obtain the hydrochlorinated target compound as a white solid (756 mg, yield: 68.05%). $^1$H NMR (400 MHz, D$_2$O) δ 3.26 (s, 6H), 3.17 (m, 3H), 2.77-2.75 (m, 6H), 2.52-2.50 (m, 6H). MS (ES+) m/z 327.55 [M+H]$^+$.

Example 17: Synthesis of (S)-2-amino-N—((R)-1-amino-3-mercapto-1-oxopropan-2-yl)-3-mercaptopropanamide trifluoroacetate

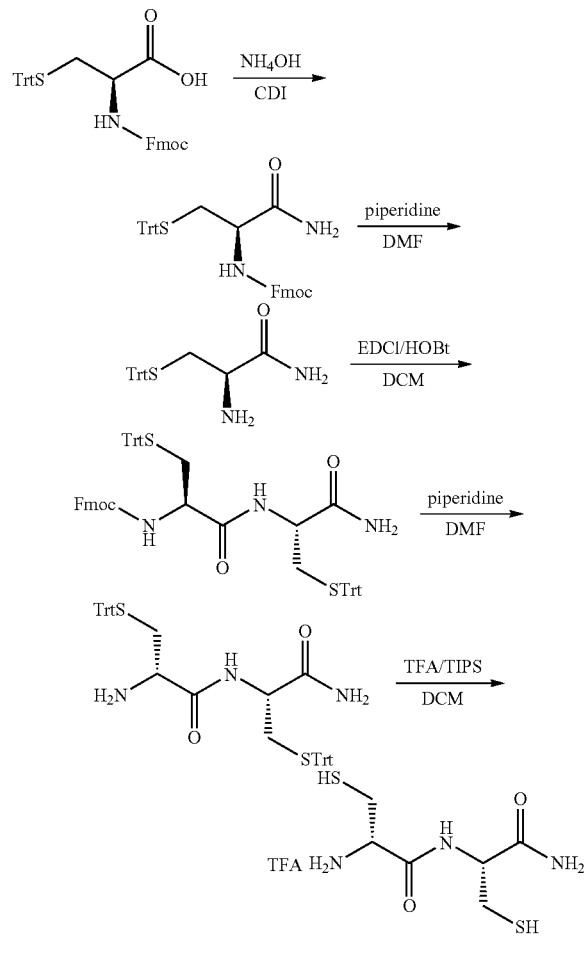

Step 1: Synthesis of (9H-fluoren-9-yl) methyl (R)-(1-amino-1-oxo-3-(tritylthio)propan-2-yl) carbamate

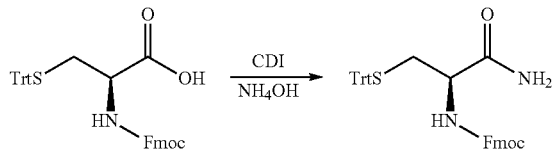

The compound (R)-2-(((9H-fluoren-9-yl)methoxy)carbonyl)amino)-3-(tritylthio) propionic acid (10 g, 17.07 mmol) was dissolved in tetrahydrofuran (50 ml). N,N'-carbonyldiimidazole (5.59 g, 34.48 mmol) was added at 0-5° C. After stirring for 2 hours under nitrogen protection, aqueous ammonia (5 ml, 68.28 mmol) was added, and reacted at 0-5° C. for 30 minutes. After the reaction was completed as detected by TLC, 2 M hydrochloric acid (60 ml) was added for quenching. The reaction mixture was extracted with ethyl acetate, the organic phase was washed with a saturated saline, then dried with sodium sulfate, and concentrated to obtain a crude product. After adding anhydrous methanol (20 ml) and stirring at room temperature overnight, white solids were precipitated, and filtered to obtain the product in the filter cake. The methanol phase was concentrated and separated by column chromatography (methanol:dichloromethane: 1%-5%) to obtain the target product as a white solid (9.3 g, yield: 93.19%). $^1$H NMR (400 MHz, DMSO-d6) δ 7.89 (d, 2H), 7.74 (d, 2H), 7.58 (d, 1H), 7.3 (m, 18H), 7.11 (s, 1H), 4.24 (m, 3H), 4.01 (m, 1H), 2.39 (m, 2H).

Step 2: Synthesis of (R)-2-amino-3-(tritylthio) propionamide

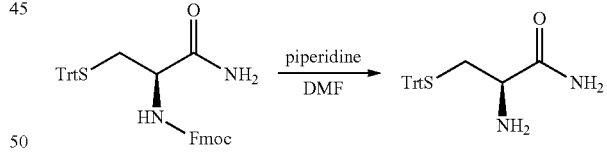

The compound (9H-fluoren-9-yl) methyl (R)-(1-amino-1-oxo-3-(tritylthio)propan-2-yl) carbamate (4 g, 6.84 mmol) was dissolved in N,N-dimethylformamide (20 ml). Piperidine (0.14 ml, 1.368 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane=1%-5%) to obtain the target product as a yellow oil (2.3 g, yield: 92%). $^1$H NMR (400 MHz, DMSO-d6) δ 7.29 (m, 17H), 3.08 (d, 1H), 2.33 (d, 1H), 2.18 (s, 1H), 1.85 (s, 2H).

Step 3: Synthesis of (9H-fluoren-9-yl) methyl ((R)-1-(((R)-1-amino-1-oxo-3-(tritylthio)propan-2-yl)amino)-1-oxo-3-(tritylthio)propan-2-yl) carbamate

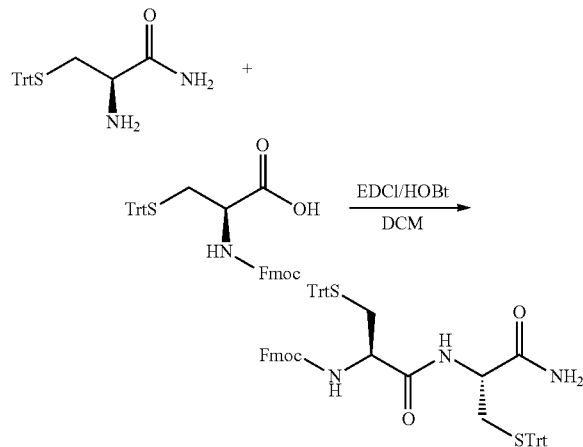

The compound (R)-2-((((9H-fluoren-9-yl)methoxy)carbonyl)amino)-3-(tritylthio) propanoic acid (1.29 g, 2.21 mmol) was dissolved in dichloromethane (15 ml). 1-hydroxybenzotriazole (448 mg, 3.315 mmol) and EDCI (635 mg, 3.315 mmol) were added, and stirred at room temperature for 5 min. (9H-fluoren-9-yl) methyl (R)-(1-amino-1-oxo-3-(tritylthio)propan-2-yl) carbamate (960 mg, 2.65 mmol) was added and reacted at room temperature for 30 minutes. After the reaction was completed as detected by TLC, the mixture was washed with a saturated saline and extracted with dichloromethane. The organic phase was dried with sodium sulfate, concentrated, and separated by column chromatography (methanol:dichloromethane: 1%-5%) to obtain the product as a white solid (2.05 g, yield: 99.76%). $^1$H NMR (400 MHz, DMSO-d6) δ 7.89 (m, 3H), 7.7 (m, 3H), 7.4 (m, 2H), 7.24 (m, 34H), 4.21 (m, 4H), 4.10 (m, 1H), 2.33 (m, 4H).

Step 4: Synthesis of (S)-2-amino-N—((R)-1-amino-1-oxo-3-(tritylthio) propan-2-yl)-3-(tritylthio) propionamide

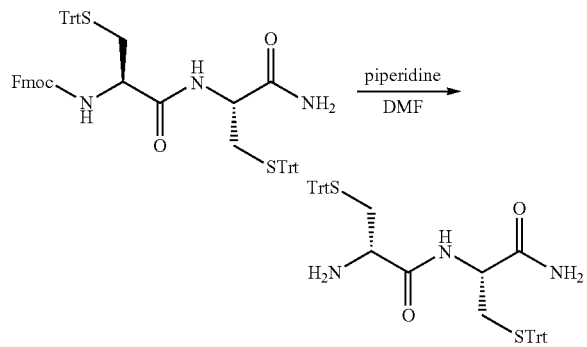

The compound (9H-fluoren-9-yl) methyl ((R)-1-(((R)-1-amino-1-oxo-3-(tritylthio)propan-2-yl) amino)-1-oxo-3-(tritylthio)propan-2-yl) carbamate (2.05 g, 2.2 mmol) was dissolved in N,N-dimethylformamide (20 ml). Piperidine (0.04 ml, 0.44 mmol) was added and stirred at room temperature for 4 hours. After the reaction was completed as detected by TLC detection, the reaction mixture was washed with a saturated saline and extracted with dichloromethane. The organic phase was dried with sodium sulfate, concentrated, and separated by column chromatography (methanol:dichloromethane: 1%-5%) to obtain the product as a white solid (460 mg, yield: 29.54%). $^1$H NMR (400 MHz, DMSO-d6) δ 8.1 (s, 1H), 7.37-7.14 (m, 32H), 4.23 (m, 1H), 3.17 (m, 1H), 2.39 (dd, 1H), 2.33 (d, 2H), 2.19 (m, 1H).

Step 5: Synthesis of (S)-2-amino-N—((R)-1-amino-3-mercapto-1-oxopropan-2-yl)-3-mercaptopropanamide trifluoroacetate

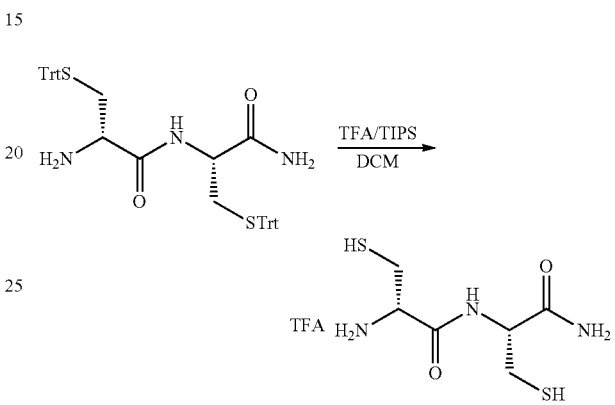

The compound (S)-2-amino-N—((R)-1-amino-1-oxo-3-(tritylthio)propan-2-yl)-3-(tritylthio) propionamide (200 mg, 0.28 mmol) was dissolved in dichloromethane (5 ml). Triisopropylsilane (0.14 ml, 0.7 mmol) and trifluoroacetic acid (1 ml) were added at 0° C. under a nitrogen atmosphere and stirred in an ice bath for 2 hours. After the reaction was completed as detected by TLC, the mixture was concentrated, diethyl ether was added, and stirred in the ice bath. White solids were precipitated, filtered and dried to obtain the product (79 mg, yield: 88.08%). $^1$H NMR (400 MHz, DMSO-d6) δ 8.72 (d, 1H), 8.23 (s, 3H), 7.56 (s, 1H), 7.32 (s, 1H), 4.43 (m, 1H), 4.09 (m, 1H), 2.99 (d, 2H), 2.89 (m, 1H), 2.74 (m, 1H); HESI: 224.05 [M+H]$^+$.

Example 18: Synthesis of (R)-2-amino-N—((S)-1-amino-3-mercapto-1-oxopropan-2-yl)-3-mercaptopropanamide trifluoroacetate

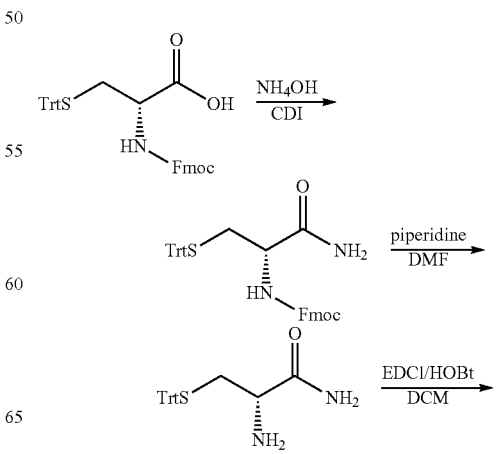

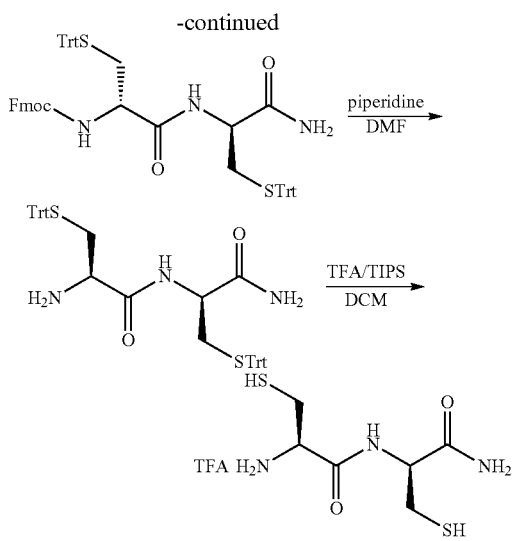

Step 1: Synthesis of (9H-fluoren-9-yl) methyl (S)-(1-amino-1-oxo-3-(tritylthio)propan-2-yl) carbamate

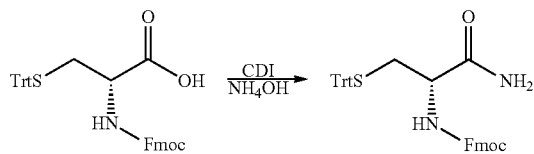

The compound (S)-2-(((9H-fluoren-9-yl)methoxy)carbonyl)amino)-3-(tritylthio) propionic acid (10 g, 17.07 mmol) was dissolved in tetrahydrofuran (50 ml). N,N'-carbonyldiimidazole (5.59 g, 34.48 mmol) was added at 0-5° C. After stirring for 2 hours under nitrogen protection, aqueous ammonia (5 ml, 68.28 mmol) was added, and reacted at 0-5° C. for 30 minutes. After the reaction was completed as detected by TLC, 2 M hydrochloric acid (60 ml) was added for quenching. The reaction mixture was extracted with ethyl acetate, the organic phase was washed with a saturated saline, then dried with sodium sulfate, and concentrated to obtain a crude product. After adding anhydrous methanol (20 ml) and stirring at room temperature overnight, white solids were precipitated, and filtered to obtain the product in the filter cake. The methanol phase was concentrated and separated by column chromatography (methanol:dichloromethane: 1%-5%) to obtain the target product as a white solid (8.93 g, yield: 89.48%). ¹H NMR (400 MHz, DMSO-d6) δ 7.89 (d, 2H), 7.74 (d, 2H), 7.58 (d, 1H), 7.3 (m, 18H), 7.11 (s, 1H), 4.24 (m, 3H), 4.01 (m, 1H), 2.39 (m, 2H).

Step 2: Synthesis of (S)-2-amino-3-(tritylthio) propionamide

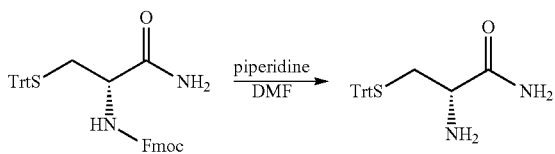

The compound (9H-fluoren-9-yl) methyl (S)-(1-amino-1-oxo-3-(tritylthio)propan-2-yl) carbamate (5.98 g, 10.23 mmol) was dissolved in N,N-dimethylformamide (20 ml). Piperidine (0.2 ml, 2.046 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane=1%-5%) to obtain the target product as a yellow oil (2.68 g, yield: 72.24%). ¹H NMR (400 MHz, DMSO-d6) δ 7.29 (m, 17H), 3.08 (d, 1H), 2.33 (d, 1H), 2.18 (s, 1H), 1.85 (s, 2H).

Step 3: Synthesis of (9H-fluoren-9-yl) methyl ((S)-1-(((S)-1-amino-1-oxo-3-(tritylthio)propan-2-yl) amino)-1-oxo-3-(tritylthio)propan-2-yl) carbamate

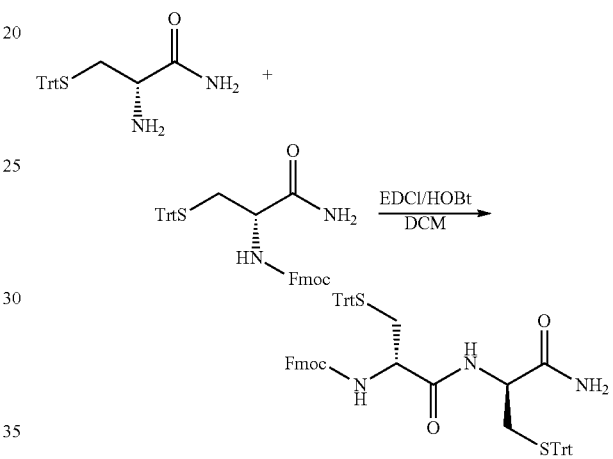

The compound (S)-2-((((9H-fluoren-9-yl)methoxy)carbonyl)amino)-3-(tritylthio) propanoic acid (3.61 g, 6.16 mmol) was dissolved in dichloromethane (25 ml). 1-hydroxybenzotriazole (1.25 mg, 9.24 mmol) and EDCI (1.77 mg, 9.24 mmol) were added, and stirred at room temperature for 5 min. (9H-fluoren-9-yl) methyl (S)-(1-amino-1-oxo-3-(tritylthio)propan-2-yl) carbamate (2.68 mg, 7.39 mmol) was added and reacted at room temperature for 30 minutes. After the reaction was completed as detected by TLC, the mixture was washed with a saturated saline and extracted with dichloromethane. The organic phase was dried with sodium sulfate, concentrated, and separated by column chromatography (methanol:dichloromethane: 1%-5%) to obtain the product as a white solid (5.56 g, yield: 97.03%). ¹H NMR (400 MHz, DMSO-d6) δ 7.89 (m, 3H), 7.7 (m, 3H), 7.4 (m, 2H), 7.24 (m, 34H), 4.21 (m, 4H), 4.10 (m, 1H), 2.33 (m, 4H).

Step 4: Synthesis of (R)-2-amino-N—((S)-1-amino-1-oxo-3-(tritylthio) propan-2-yl)-3-(tritylthio) propionamide

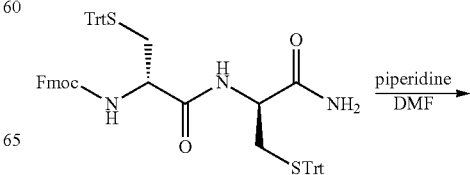

-continued

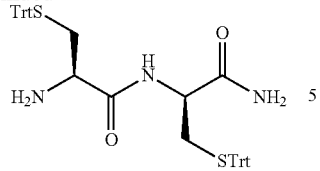

-continued

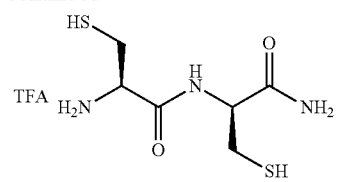

The compound (9H-fluoren-9-yl) methyl ((S)-1-(((S)-1-amino-1-oxo-3-(tritylthio)propan-2-yl) amino)-1-oxo-3-(tritylthio)propan-2-yl) carbamate (5.56 g, 5.98 mmol) was dissolved in N,N-dimethylformamide (25 ml). Piperidine (0.12 ml, 1.196 mmol) was added and stirred at room temperature for 4 hours. After the reaction was completed as detected by TLC detection, the reaction mixture was washed with a saturated saline and extracted with dichloromethane. The organic phase was dried with sodium sulfate, concentrated, and separated by column chromatography (methanol:dichloromethane: 1%-5%) to obtain the product as a white solid (1.27 g, yield: 30%). $^1$H NMR (400 MHz, DMSO-d6) δ 8.1 (s, 1H), 7.37-7.14 (m, 32H), 4.23 (m, 1H), 3.17 (m, 1H), 2.39 (dd, 1H), 2.33 (d, 2H), 2.19 (m, 1H).

Step 5: Synthesis of (R)-2-amino-N—((S)-1-amino-3-mercapto-1-oxopropan-2-yl)-3-mercaptopropanamide trifluoroacetate The compound (R)-2-amino-N—((S)-1-amino-1-oxo-3-(tritylthio)propan-2-yl)-3-(tritylthio) propionamide (40 mg, 0.057 mmol) was dissolved in dichloromethane (5 ml). Triisopropylsilane (0.03 ml, 0.1425 mmol) and trifluoroacetic acid (1 ml) were added at 0° C. under a nitrogen atmosphere and stirred in an ice bath for 2 hours. After the reaction was completed as detected by TLC, the mixture was concentrated, diethyl ether was added, and stirred in the ice bath. White solids were precipitated, filtered and dried to obtain the product (16 mg, yield: 83.2%). $^1$H NMR (400 MHz, DMSO-d6) δ 8.72 (d, 1H), 8.23 (s, 3H), 7.56 (s, 1H), 7.32 (s, 1H), 4.43 (m, 1H), 4.09 (m, 1H), 2.99 (d, 2H), 2.89 (m, 1H), 2.74 (m, 1H); HESI: 224.05 [M+H]$^+$.

Example 19: Synthesis of 3-mercapto-N-(3-mercapto-1-(methylamino)-1-oxopropan-2-yl)-2-(methylamino) propionamide trifluoroacetate

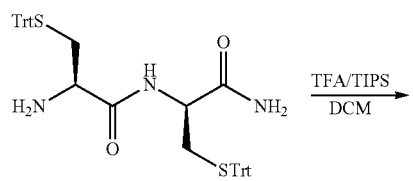

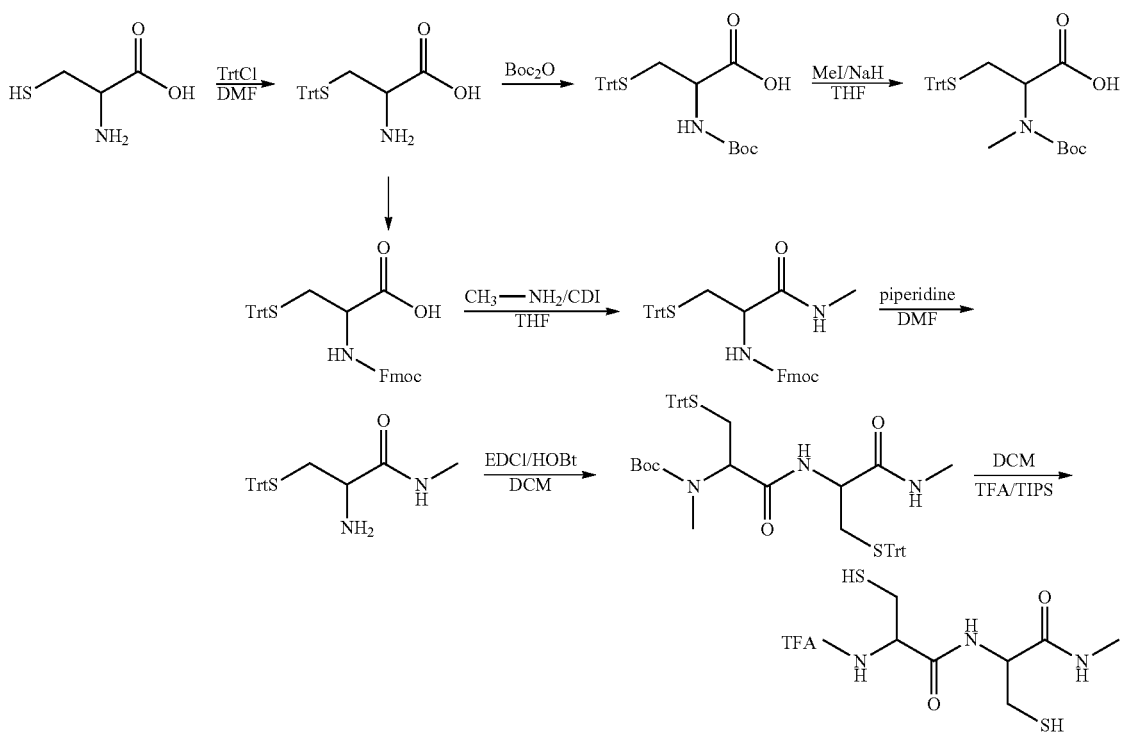

Step 1: Synthesis of S-trityl-DL-cysteine

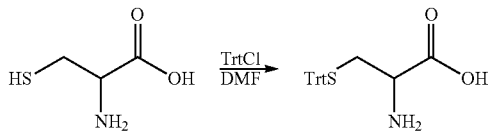

The compound DL-cysteine hydrochloride (10 g, 63.45 mmol) was dissolved in N,N-dimethylformamide (120 ml). Triphenylchloromethane (19.46 g, 69.795 mmol) was added, heated to 60-65° C., and reacted for 8 h. After the reaction was completed as detected by TLC, the reaction was cooled to room temperature, and 10% sodium acetate solution (300 ml) was added. White solids were then precipitated and filtered. Filter residue was washed with pure water (300 ml), then washed with acetone (200 ml), and dried to obtain the product as a white solid (17.54 g, yield: 76.06%). $^1$H NMR (400 MHz, DMSO-d6) δ 7.27 (m, 18H), 2.92 (dd, 1H), 2.59 (dd, 1H), 2.41 (dd, 1H).

Step 2: Synthesis of N-(tert-butoxycarbonyl)-S-trityl-DL-cysteine

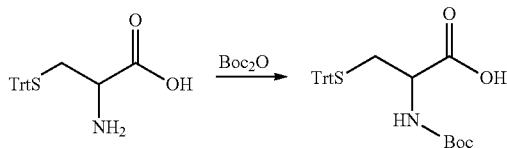

The compound S-trityl-DL-cysteine (5 g, 13.76 mmol) was dissolved in a mixture of dioxane (40 ml), water (20 ml) and 1M sodium hydroxide solution (14 ml), and stirred in an ice bath. Boc-anhydride (3.5 ml, 15.14 mmol) was added, then reacted until the mixture was naturally warmed to room temperature, and stirred for 8 hours. After the reaction was completed as detected by TLC, the reaction mixture was concentrated to 20-25 ml. Ethyl acetate was added, and the sodium bisulfate solution was added dropwise under the ice bath while stirring. After pH was adjusted to 2-3, ethyl acetate was used for extraction. The organic layer was washed with a saturated saline, then dried with sodium sulfate, concentrated, and separated by column chromatography (methanol:dichloromethane: 1%-5%) to obtain the product as a white solid (4.72 g, yield: 73.98%). $^1$H NMR (400 MHz, DMSO-d6) δ 7.26 (m, 16H), 3.77 (d, 1H), 2.51 (m, 1H), 2.36 (dd, 1H), 1.4 (d, 9H).

Step 3: Synthesis of N-(tert-butoxycarbonyl)-N-methyl-S-trityl-DL-cysteine

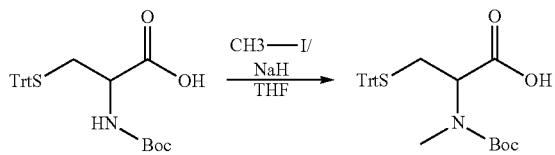

The compound N-(tert-butoxycarbonyl)-S-trityl-DL-cysteine (1 g, 2.16 mmol) was dissolved in anhydrous tetrahydrofuran (6 ml). Sodium hydride (259.2 mg, 6.48 mmol) was dissolved in anhydrous tetrahydrofuran (10 ml). The solution of amino acid in tetrahydrofuran was added dropwise to the solution of sodium hydride in tetrahydrofuran in an ice bath. Then, methyl iodide (1.08 ml, 17.28 mmol) was slowly added dropwise and stirred overnight. After the reaction was completed as detected by TLC, phosphate buffer at pH=7 was added for quenching. pH was adjusted to 6-7 with a saturated ammonium chloride solution, and was extracted with ethyl acetate. The organic layer was washed with a saturated saline, then dried with sodium sulfate, concentrated, and separated by column chromatography (methanol:dichloromethane: 1%-5%) to obtain the product as a white solid (462 mg, yield: 44.85%). $^1$H NMR (400 MHz, DMSO-d6) δ 7.3 (m, 15H), 3.75 (s, 1H), 2.7 (s, 1H), 2.66 (d, 4H), 1.4 (d, 9H).

Step 4: Synthesis of (RS)-2-(((9H-fluoren-9-yl)methoxy)carbonyl)amino)-3-(tritylthio) propionic acid

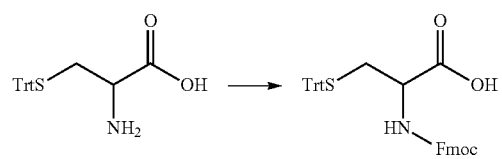

The compound S-trityl-DL-cysteine (5 g, 13.76 mmol) was dissolved in tetrahydrofuran (30 ml) and water (30 ml), sodium hydrogen carbonate (2.31 g, 27.52 mmol) was added with stirring, and 9-fluorenyl methyl-N-succinimidyl carbonate (4.39 g, 13 mmol) was stirred at room temperature for 3.5 hours. After the reactants were consumed, the reaction mixture was extracted with dichloromethane. The organic layer was washed with a saturated saline, then dried with sodium sulfate, concentrated and separated by column chromatography (methanol:dichloromethane: 1%-5%) to obtain a white solid (6.61 g, yield: 82.02%). $^1$H NMR (300 MHz, DMSO) δ 7.89 (d, J=7.5 Hz, 2H), 7.73 (d, J=7.5 Hz, 2H), 7.52-7.14 (m, 19H), 4.38-4.09 (m, 3H), 3.84 (dd, J=8.6, 5.1 Hz, 1H), 2.67-2.56 (m, 1H), 2.41 (dd, J=12.3, 4.6 Hz, 1H).

Step 5: Synthesis of (9H-fluoren-9-yl) methyl (RS)-(1-(methylamino)-1-oxo-3-(tritylthio)propan-2-yl) carbamate

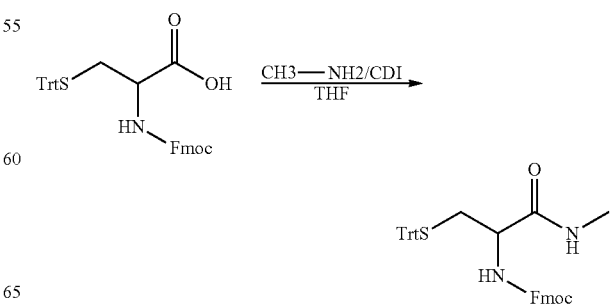

The compound (RS)-2-(((9H-fluoren-9-yl)methoxy)carbonyl)amino)-3-(tritylthio) propionic acid (6.6 g, 11.27 mmol) was dissolved in tetrahydrofuran (25 ml). N,N'-carbonyldiimidazole (3.7 g, 22.77 mmol) was added at 0-5° C. After stirring for 2 hours under nitrogen atmosphere, methylamine (2 ml, 45.08 mmol) was added, and reacted at 0-5° C. for 2 hours. After the reactants were consumed, 2M hydrochloric acid (30 ml) was added for quenching, and the reaction mixture was extracted with dichloromethane. The organic layer was washed with a saturated saline, then dried with sodium sulfate and concentrated to obtain a crude product. Methanol (20 ml) was added and stirred overnight at room temperature. White solids were precipitated, and filtered to obtain the product in filter residue. The methanol phase was concentrated, and separated by column chromatography (methanol:dichloromethane: 1%-5%) to obtain a white solid (6.5 g, yield: 96.32%). $^1$H NMR (400 MHz, DMSO) δ 7.89 (d, 2H), 7.81 (d, 1H), 7.74 (d, 2H), 7.66 (d, 1H), 7.41 (t, 2H), 7.29 (m, 17H), 4.31 (d, 1H), 4.22 (t, 2H), 4.00 (d, 1H), 2.53 (d, 3H), 2.39 (d, 2H).

Step 6: Synthesis of (RS)-2-amino-N-methyl-3-(tritylthio) propionamide

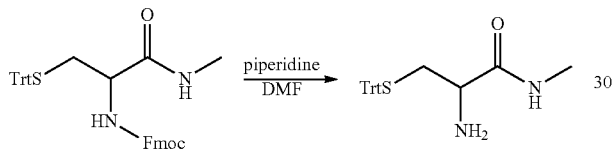

The compound (9H-fluoren-9-yl) methyl (RS)-(1-(methylamino)-1-oxo-3-(tritylthio)propan-2-yl) carbamate (1 g, 1.67 mmol) was dissolved in N,N-dimethylformamide (20 ml). Piperidine (0.03 ml, 0.334 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane: 1%-5%) to obtain the product as a yellowish white solid (540 mg, yield: 85.88%). $^1$H NMR (400 MHz, CDCl$_3$) 7.77 (d, 1H), 7.29 (m, 15H), 3.08 (m, 1H), 2.55 (d. 3H), 2.37 (dd, 1H), 2.19 (dd, 1H), 1.80 (s, 2H).

Step 7: Synthesis of tert-butyl methyl ((RS)-1-(((RS)-1-(methylamino)-1-oxo-3-(tritylthio)propan-2-yl)amino)-1-oxo-3-(tritylthio)propan-2-yl) carbamate

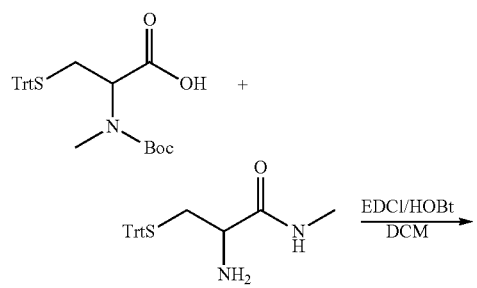

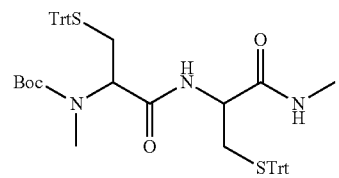

The compound N-(tert-butoxycarbonyl)-N-methyl-S-trityl-DL-cysteine (500 g, 1.328 mmol) was dissolved in dichloromethane (5 ml). 1-hydroxybenzotriazole (269.32 mg, 1.992 mmol) and EDCI (381.87 mg, 1.992 mmol) were added, and stirred at room temperature for 5 min. (RS)-2-amino-N-methyl-3-(tritylthio) propanamide (634 mg, 1.328 mmol) was added and stirred at room temperature for 30 minutes. After the reaction was completed as detected by TLC, the mixture was washed with a saturated saline and extracted with dichloromethane. The organic phase was dried with sodium sulfate, then concentrated and purified with TLC (dichloromethane:methanol: 15:1) to obtain the product as a white solid (940 mg, yield: 84.66%). $^1$H NMR (400 MHz, CDCl$_3$) δ 7.39 (m, 12H), 7.22 (m, 20H), 4.1 (d, 1H), 3.95 (s, 1H), 2.61 (dd, 10H), 1.39 (s, 9H).

Step 8: Synthesis of (RS)-3-mercapto-N—((RS)-3-mercapto-1-(methylamino)-1-oxopropan-2-yl)-2-(methylamino) propionamide trifluoroacetate

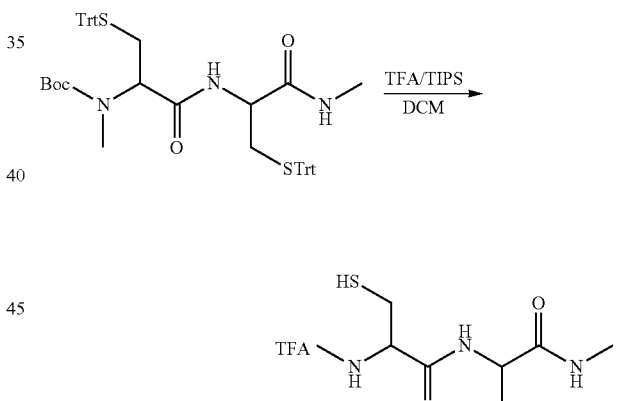

The compound tert-butyl methyl ((RS)-1-(((RS)-1-(methylamino)-1-oxo-3-(tritylthio)propan-2-yl)amino)-1-oxo-3-(tritylthio)propan-2-yl) carbamate (200 mg, 0.239 mmol) was dissolved in dichloromethane:trifluoroacetic acid:triisopropylsilane (50:47:3 by volume) (5 ml), stirred at room temperature for 5 min. After the reaction was completed as detected by TLC, the mixture was concentrated, diethyl ether was added, and stirred in an ice bath. White solids were precipitated, filtered and dried to obtain the product (70 mg, yield: 84.07%). $^1$H NMR (400 MHz, DMSO) δ 8.89 (d, J=8.1 Hz, 2H), 8.12 (d, J=4.3 Hz, 1H), 4.48-4.34 (m, 1H), 4.04 (s, 1H), 3.10 (dt, J=12.5, 6.2 Hz, 1H), 3.04-2.93 (m, 1H), 2.91-2.81 (m, 1H), 2.78-2.65 (m, 1H), 2.62 (d, J=4.6 Hz, 3H), 2.56 (s, 3H), 2.37 (t, J=13.7 Hz, 1H), 1.29 (d, J=7.0 Hz, 1H).

Example 20: Synthesis of 2-amino-N-(1-((1-amino-3-mercapto-1-oxopropan-2-yl)amino)-3-mercapto-1-oxopropan-2-yl)-3-mercaptopropylamide trifluoroacetate

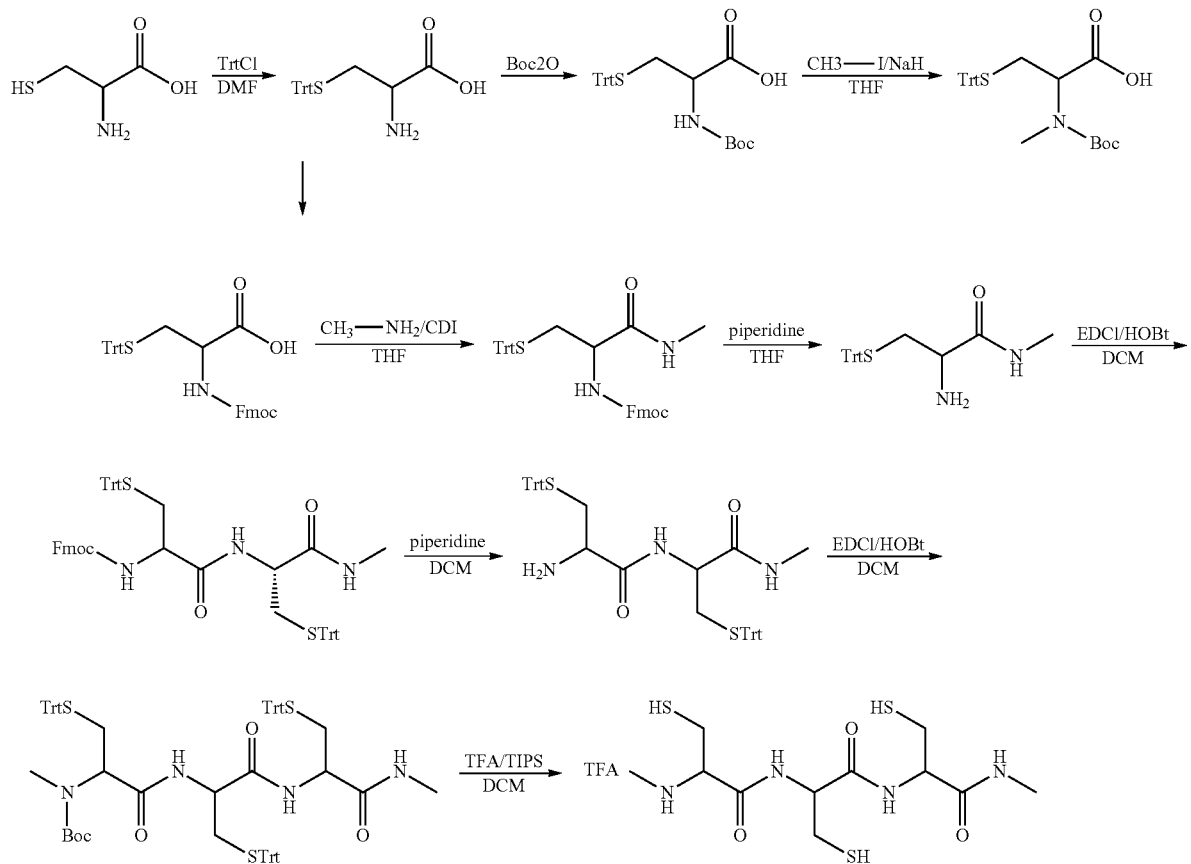

Step 1: Synthesis of S-trityl-DL-cysteine

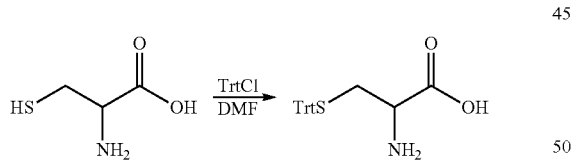

The compound DL-cysteine hydrochloride (10 g, 63.45 mmol) was dissolved in N,N-dimethylformamide (120 ml). Triphenylchloromethane (19.46 g, 69.795 mmol) was added, heated to 60-65° C., and reacted for 8 h. After the reaction was completed as detected by TLC, the reaction was cooled to room temperature, and 10% sodium acetate solution (300 ml) was added. White solids were then precipitated and filtered. Filter residue was washed with pure water (300 ml), then washed with acetone (200 ml), and dried to obtain the product as a white solid (17.54 g, yield: 76.06%). $^1$H NMR (400 MHz, DMSO-d6) δ 7.28 (m, 18H), 2.92 (dd, 1H), 2.59 (dd, 1H), 2.41 (dd, 1H).

Step 2: Synthesis of N-(tert-butoxycarbonyl)-S-trityl-DL-cysteine

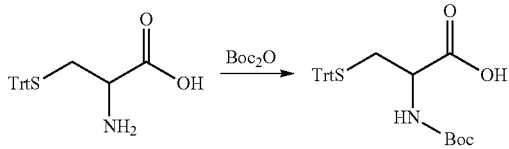

The compound S-trityl-DL-cysteine (5 g, 13.76 mmol) was dissolved in a mixture of dioxane (40 ml), water (20 ml) and 1M sodium hydroxide solution (14 ml), and stirred in an ice bath. Boc-anhydride (3.5 ml, 15.14 mmol) was added, then reacted until the mixture was naturally warmed to room temperature, and stirred for 8 hours. After the reaction was completed as detected by TLC, the reaction mixture was concentrated to 20-25 ml. Ethyl acetate was added, and the sodium bisulfate solution was added dropwise under the ice bath while stirring. After pH was adjusted to 2-3, ethyl acetate was used for extraction. The organic layer was washed with a saturated saline, then dried with sodium sulfate, concentrated, and separated by column chromatography (methanol:dichloromethane: 1%-5%) to obtain the product as a white solid (4.72 g, yield: 73.98%). $^1$H NMR (400 MHz, DMSO-d6) δ 7.26 (m, 16H), 3.78 (d, 1H), 2.51 (m, 1H), 2.36 (dd, 1H), 1.4 (d, 9H).

Step 3: Synthesis of N-(tert-butoxycarbonyl)-N-methyl-S-trityl-DL-cysteine

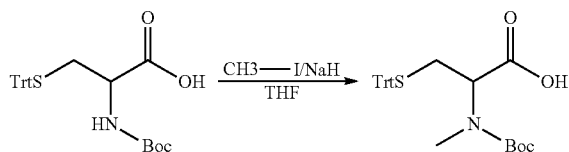

The compound N-(tert-butoxycarbonyl)-S-trityl-DL-cysteine (1 g, 2.16 mmol) was dissolved in anhydrous tetrahydrofuran (6 ml). Sodium hydride (259.2 mg, 6.48 mmol) was dissolved in anhydrous tetrahydrofuran (10 ml). The solution of amino acid in tetrahydrofuran was added dropwise to the solution of sodium hydride in tetrahydrofuran in an ice bath. Then, methyl iodide (1.08 ml, 17.28 mmol) was slowly added dropwise and stirred overnight. After the reaction was completed as detected by TLC, phosphate buffer at pH=7 was added for quenching. pH was adjusted to 6-7 with a saturated ammonium chloride solution, and was extracted with ethyl acetate. The organic layer was washed with a saturated saline, then dried with sodium sulfate, concentrated, and separated by column chromatography (methanol:dichloromethane: 1%-5%) to obtain the product as a white solid (462 mg, yield: 44.85%). $^1$H NMR (400 MHz, DMSO-d6) δ 7.3 (m, 15H), 3.75 (s, 1H), 2.8 (s, 1H), 2.66 (d, 4H), 1.4 (d, 9H).

Step 4: Synthesis of (RS)-2-(((9H-fluoren-9-yl)methoxy)carbonyl)amino)-3-(tritylthio) propionic acid

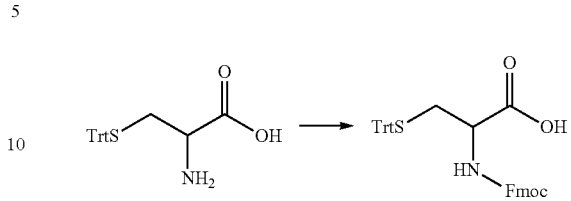

The compound S-trityl-DL-cysteine (5 g, 13.76 mmol) was dissolved in tetrahydrofuran (30 ml) and water (30 ml), sodium hydrogen carbonate (2.31 g, 27.52 mmol) was added with stirring, and 9-fluorenyl methyl-N-succinimidyl carbonate (4.39 g, 13 mmol) was stirred at room temperature for 3.5 hours. After the reactants were consumed, the reaction mixture was extracted with dichloromethane. The organic layer was washed with a saturated saline, then dried with sodium sulfate, concentrated and separated by column chromatography (methanol:dichloromethane: 1%-5%) to obtain a white solid (6.61 g, yield: 82.02%). $^1$H NMR (300 MHz, DMSO) δ 7.89 (d, J=7.5 Hz, 2H), 7.73 (d, J=7.5 Hz, 2H), 7.52-7.14 (m, 19H), 4.38-4.09 (m, 3H), 3.84 (dd, J=8.6, 5.1 Hz, 1H), 2.67-2.56 (m, 1H), 2.41 (dd, J=12.3, 4.6 Hz, 1H).

Step 5: Synthesis of (9H-fluoren-9-yl) methyl (RS)-(1-(methylamino)-1-oxo-3-(tritylthio)propan-2-yl) carbamate

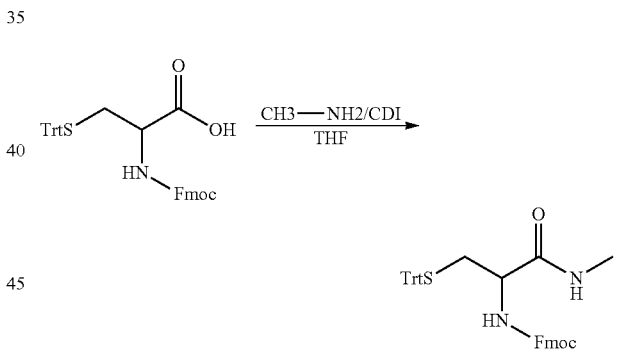

The compound (RS)-2-(((9H-fluoren-9-yl)methoxy)carbonyl)amino)-3-(tritylthio) propionic acid (6.6 g, 11.27 mmol) was dissolved in tetrahydrofuran (25 ml). N,N'-carbonyldiimidazole (3.7 g, 22.77 mmol) was added at 0-5° C. After stirring for 2 hours under nitrogen atmosphere, methylamine (2 ml, 45.08 mmol) was added, and reacted at 0-5° C. for 2 hours. After the reactants were consumed, 2M hydrochloric acid (30 ml) was added for quenching, and the reaction mixture was extracted with dichloromethane. The organic layer was washed with a saturated saline, then dried with sodium sulfate and concentrated to obtain a crude product. Methanol (20 ml) was added and stirred overnight at room temperature. White solids were precipitated, and filtered to obtain the product in filter residue. The methanol phase was concentrated, and separated by column chromatography (methanol:dichloromethane: 1%-5%) to obtain a white solid (6.5 g, yield: 96.32%). $^1$H NMR (400 MHz, DMSO) δ 7.89 (d, 2H), 7.81 (d, 1H), 7.74 (d, 2H), 7.66 (d, 1H), 7.41 (t, 2H), 7.29 (m, 17H), 4.31 (d, 1H), 4.22 (t, 2H), 4.00 (d, 1H), 2.53 (d, 3H), 2.39 (d, 2H).

Step 6: Synthesis of (RS)-2-amino-N-methyl-3-(tritylthio) propionamide

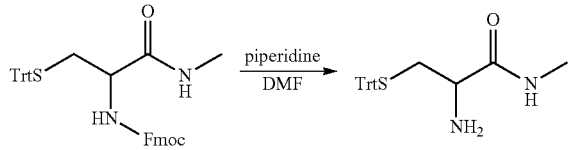

The compound (9H-fluoren-9-yl) methyl (RS)-(1-(methylamino)-1-oxo-3-(tritylthio)propan-2-yl) carbamate (1 g, 1.67 mmol) was dissolved in N,N-dimethylformamide (20 ml). Piperidine (0.03 ml, 0.334 mmol) was added and reacted at room temperature for 4 hours. After the reaction was completed as detected by TLC, the reaction mixture was washed with a saturated saline and extracted with dichloromethane. The organic phase was dried with sodium sulfate, concentrated, and separated by column chromatography (methanol:dichloromethane: 1%-5%) to obtain the product as a yellowish white solid (540 mg, yield: 85.88%). $^1$H NMR (400 MHz, CDCl$_3$) 7.77 (d, 1H), 7.29 (m, 15H), 3.08 (m, 1H), 2.55 (d. 3H), 2.37 (dd, 1H), 2.19 (dd, 1H), 1.80 (s, 2H).

Step 7: Synthesis of (9H-fluoren-9-yl) methyl ((RS)-1-(((RS)-1-(methylamino)-1-oxo-3-(tritylthio)propan-2-yl)amino)-1-oxo-3-(tritylthio)propan-2-yl) carbamate

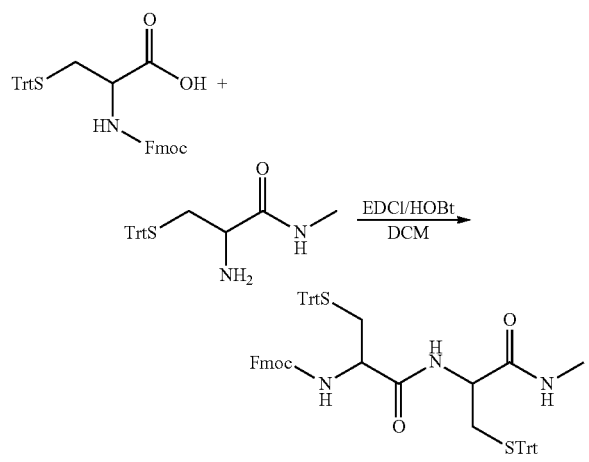

The compound (RS)-2-((((9H-fluoren-9-yl)methoxy)carbonyl)amino)-3-(tritylthio) propanoic acid (1 g, 1.71 mmol) was dissolved in dichloromethane (15 ml). 1-hydroxybenzotriazole (347 mg, 2.565 mmol) and EDCI (492 mg, 2.565 mmol) were added, and stirred at room temperature for 5 min. (R)-2-amino-N-methyl-3-(tritylthio) propanamide (644 mg, 1.71 mmol) was added and reacted at room temperature for 30 minutes. After the reaction was completed as detected by TLC, the mixture was washed with a saturated saline and extracted with dichloromethane. The organic phase was dried with sodium sulfate, then concentrated, and separated by column chromatography (methanol:dichloromethane: 1%-5%) to obtain the product as a white solid (1.06 g, yield: 65.63%). $^1$H NMR (400 MHz, DMSO-d6) δ 7.89 (d, 2H), 7.71 (m, 4H), 7.40 (m, 2H), 7.38-7.25 (m, 30H), 4.25 (m, 4H), 4.01 (m, 1H), 2.50-2.33 (m, 7H).

Step 8: Synthesis of (RS)-2-amino-N—((RS)-1-(methylamino)-1-oxo-3-(tritylthio)propan-2-yl)-3-(tritylthio) propionamide

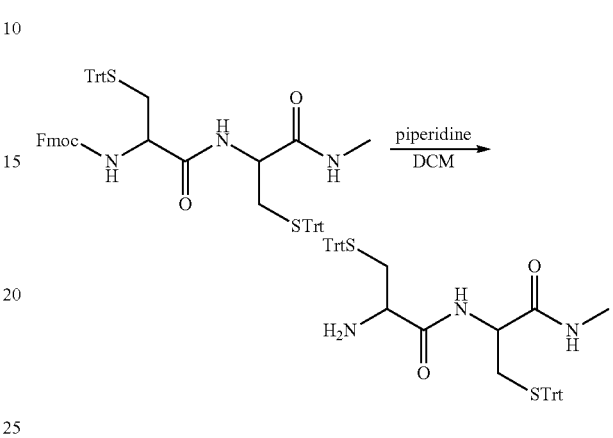

The compound (9H-fluoren-9-yl) methyl ((RS)-1-(((RS)-1-(methylamino)-1-oxo-3-(tritylthio)propan-2-yl) amino)-1-oxo-3-(tritylthio)propan-2-yl) carbamate (1.06 g, 1.12 mmol) was dissolved in N,N-dimethylformamide (10 ml). Piperidine (0.02 ml, 0.224 mmol) was added and reacted at room temperature for 4 hours. After the reaction was completed as detected by TLC detection, the reaction mixture was washed with a saturated saline and extracted with dichloromethane. The organic phase was dried with sodium sulfate, then concentrated, and separated by column chromatography (methanol:dichloromethane: 1%-5%) to obtain the product as a white solid (790 mg, yield: 97.7%). $^1$H NMR (400 MHz, DMSO-d6) δ 8.12 (s, 1H), 7.83 (d, 1H), 7.27 (m, 30H), 4.25 (s, 1H), 3.29 (m, 2H), 3.20 (s, 1H), 2.65-2.23 (m, 5H).

Step 9: Synthesis of tert-butyl methyl((4RS,7RS,10RS)-3,6,9-trioxo-13,13,13-triphenyl-4,7-bis((tritylthio)methyl)-12-thia-2,5,8-triazatridec-10-yl) carbamate

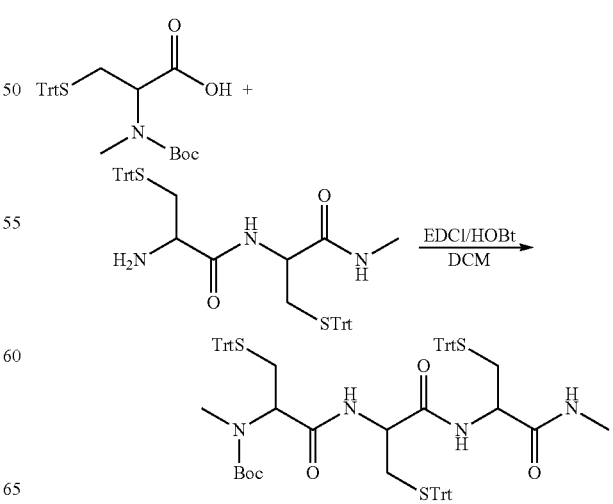

The compound N-(tert-butoxycarbonyl)-N-methyl-S-trityl-DL-cysteine (505 mg, 1.06 mmol) was dissolved in dichloromethane (10 ml). 1-hydroxybenzotriazole (215 mg, 1.59 mmol) and EDCI (304.8 mg, 1.59 mmol) were added, and stirred at room temperature for 5 min. (RS)-2-amino-N—((RS)-1-(methylamino)-1-oxo-3-(tritylthio)propan-2-yl)-3-(tritylthio) propanamide (765.3 mg, 1.06 mmol) was added and reacted at room temperature for 30 minutes. After the reaction was completed as detected by TLC, the mixture was washed with a saturated saline and extracted with dichloromethane. The organic phase was dried with sodium sulfate, concentrated, and separated by column chromatography (methanol:dichloromethane: 1%-5%) to obtain the product as a white solid (1.1 g, yield: 88%). $^1$H NMR (400 MHz, DMSO-d6) δ 8.11 (d, 1H), 7.73 (d, 2H), 7.32-7.21 (m, 45H), 4.25 (m, 3H), 2.62 (m, 1H), 2.49 (m, 6H) 2.47-2.23 (m, 5H), 1.35-1.21 (d, 9H).

Step 10: Synthesis of (RS)-3-mercapto-N—((RS)-3-mercapto-1-(((RS)-3-mercapto-1-(methylamino)-1-oxopropan-2-yl)amino)-1-oxopropan-2-yl)-2-(methylamino) propanamide trifluoroacetate

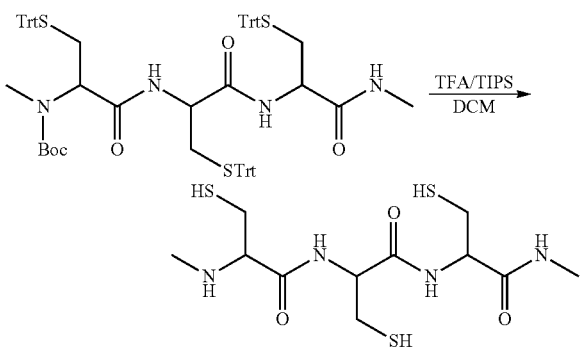

The compound tert-butyl methyl((4RS,7RS,10RS)-3,6,9-trioxo-13,13,13-triphenyl-4,7-bis((tritylthio)methyl)-12-thia-2,5,8-triazatridec-10-yl) carbamate (400 mg, 0.339 mmol) was dissolved in dichloromethane:trifluoroacetic acid:triisopropylsilane (50:47:3 by volume) (10 ml), stirred at room temperature for 5 min. After the reaction was completed as detected by TLC, the mixture was concentrated, diethyl ether was added, and stirred in an ice bath. White solids were precipitated, filtered and dried to obtain the product (131 mg, yield: 85.4%). $^1$H NMR (400 MHz, DMSO) δ 8.92 (dd, J=14.8, 9.8 Hz, 3H), 8.58-8.33 (m, 1H), 7.97 (dd, J=22.8, 4.4 Hz, 1H), 4.64-4.50 (m, 1H), 4.34 (td, J=13.4, 7.9 Hz, 1H), 4.05 (d, J=5.4 Hz, 1H), 3.17-2.66 (m, 7H), 2.60 (d, J=3.9 Hz, 3H), 2.56 (d, J=5.7 Hz, 3H), 2.36-2.27 (m, 1H).

Examples of biological activity:

Example A

The protective effects of compounds 1, 2, 3 and 4 on survival rate, white blood cells and organs of mice 30 days after irradiation.

Material: The gamma ray irradiation device is a $^{137}$Cs irradiator, with a dose rate of 0.7Gy/min. C57BL/6 mice, male, weighing 21-22 g, purchased from Beijing HFK Bioscience Co. Ltd., certificate number SCXK (Beijing) 2014-0004, grouped as: no irradiation group, irradiation and blank solvent group, irradiation and administration group, with 5 mice in each group. The structures of compounds 1, 2, 3 and 4 (prepared from Examples 1, 7, 2 and 3, respectively) are shown in Table 1.

TABLE 1

| Nomenclature and structural formula of compounds 1-4 | | |
|---|---|---|
| Compound No. | Compound name | Structural formula |
| Compound 1 (Example 1) | (R)-2-amino-N-((R)-1-amino-3-mercapto-1-oxopropan-2-yl)-3-mercaptopropanamide trifluoroacetate | |
| Compound 2 (Example 7) | (S)-3-mercapto-N-((S)-3-mercapto-1-(methylamino)-1-oxopropan-2-yl)-2-(methylamino)propionamide trifluoroacetate | |
| Compound 3 (Example 2) | (R)-3-mercapto-N-((R)-3-mercapto-1-(methylamino)-1-oxopropan-2-yl)-2-(methylamino)propionamide trifluoroacetate | |

TABLE 1-continued

Nomenclature and structural formula of compounds 1-4

| Compound No. | Compound name | Structural formula |
| --- | --- | --- |
| Compound 4 (Example 3) | (R)-2-amino-N-((R)-1-(((R)-1-amino-3-mercapto-1-oxopropan-2-yl)amino)-3-mercapto-1-oxopropan-2-yl)-3-mercaptopropanamide trifluoroacetate | (structure shown) |

Method: Irradiation and drug treatment: $^{137}$Cs γ-ray irradiation was carried out on the whole body at an irradiation dose rate of 0.7Gy/min, and the absorbed dose of mice was 6.8Gy, 7.2Gy and 7.5Gy, respectively; aminofostine, compound 1, compound 2, compound 3, and compound 4 were dissolved in normal saline, shaken evenly when administering them (200 mg/kg BW), and injected intraperitoneally 30 min before irradiation. The 30-day survival of the mice in each group was observed, the survival rates were calculated, the body weights were followed, and the organs and white blood cells of mice in each group were compared after 30 days.

Figure 1B:
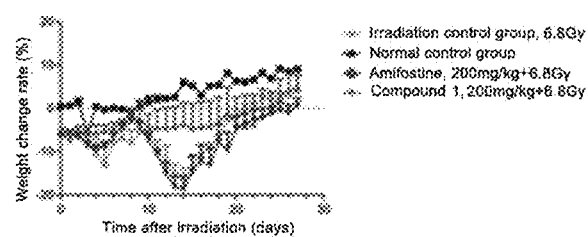
Figure 2A:
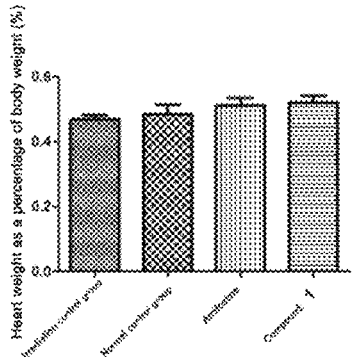
Figure 2B:
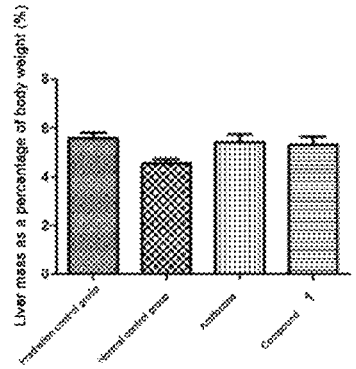
Figure 2C:
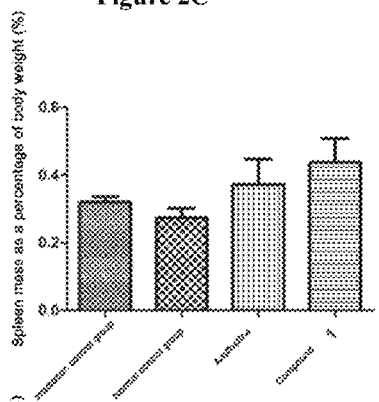
Figure 2D:
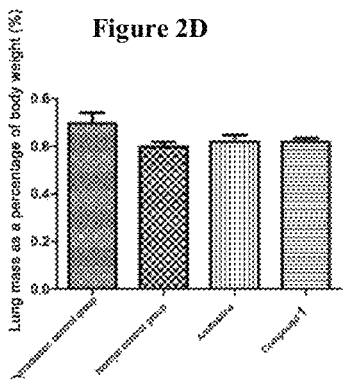
Figure 2E:
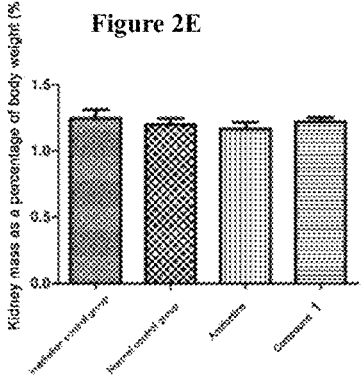
Figure 2F:
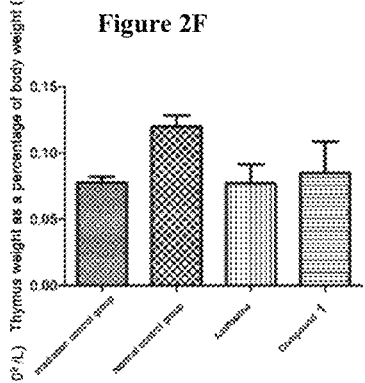
Figure 2G:
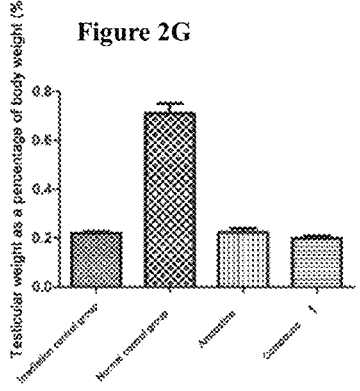
Figure 2H:
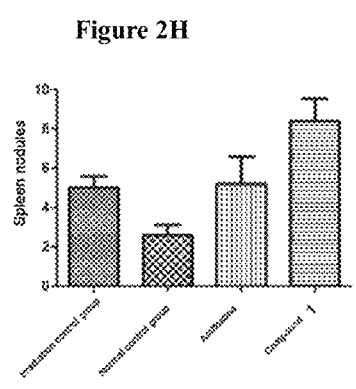
Figure 2I:
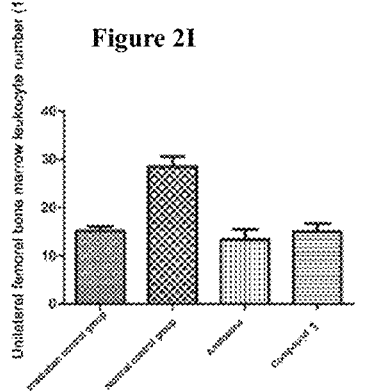
Figure 2J:
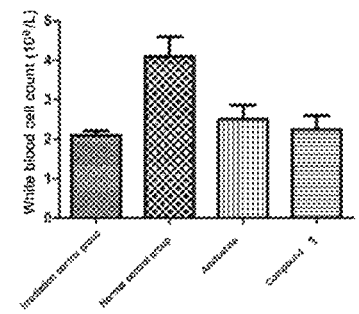
Figure 3A:
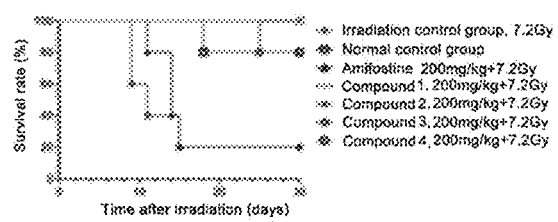
Figure 3B:
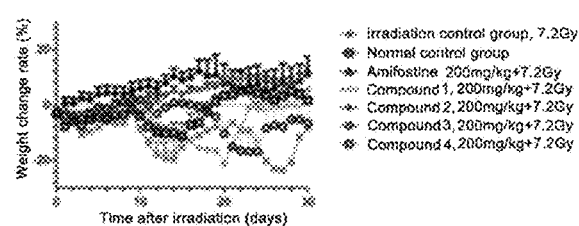
FIG. 3B shows the effect of compounds 1-4 on the body weight of mice irradiated with 7.2Gy γ rays.
Figure 4A:
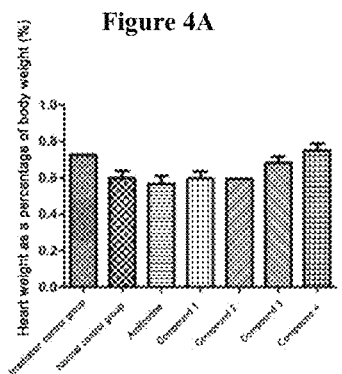
Figure 4B:
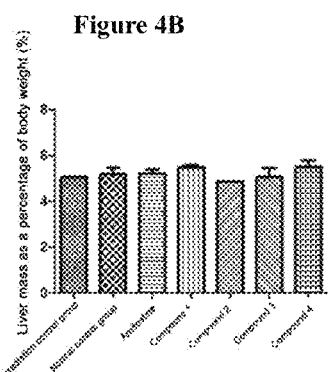
Figure 4C:
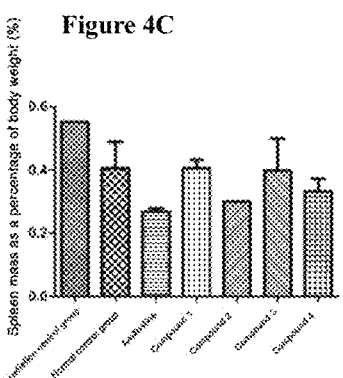
Figure 4D:
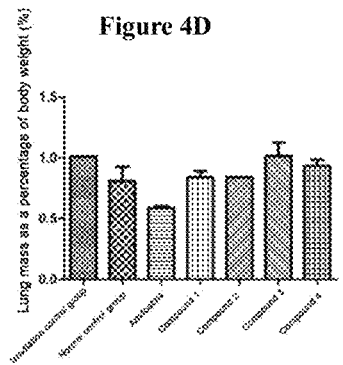
Figure 4E:
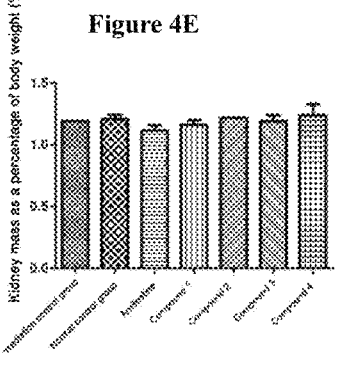
Figure 4F:
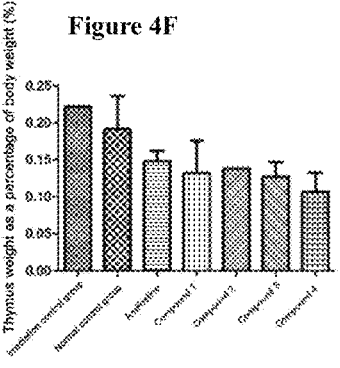
Figure 4G:
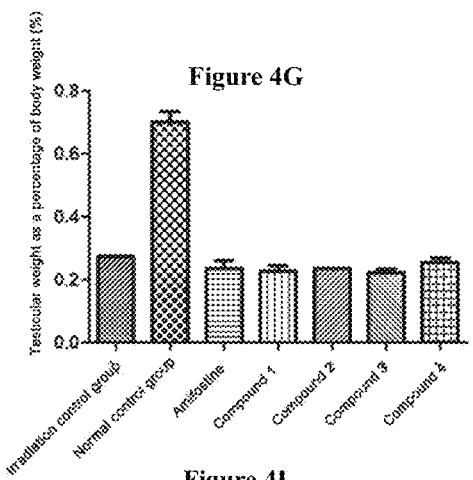
Figure 4H:
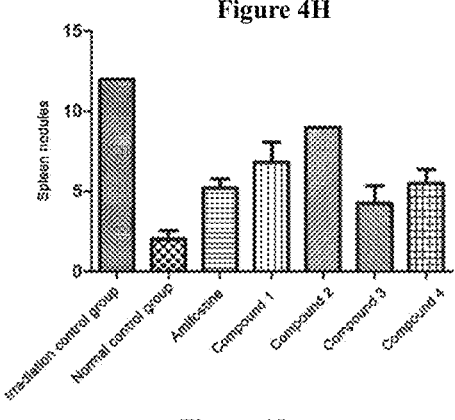
Figure 4I:
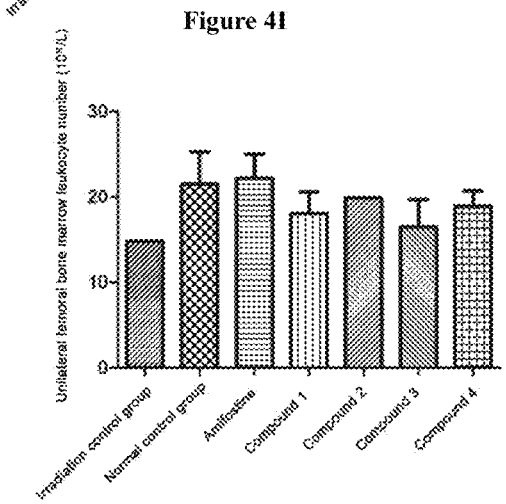
Figure 4J:
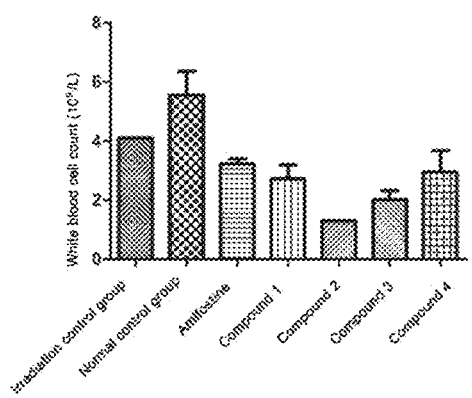
Figure 5A:
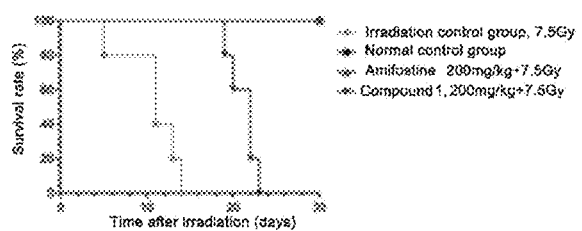
Figure 5B:
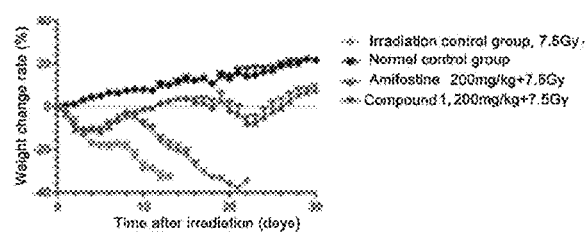
Figure 6A:
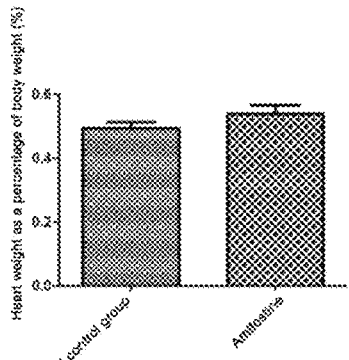
Figure 6B:
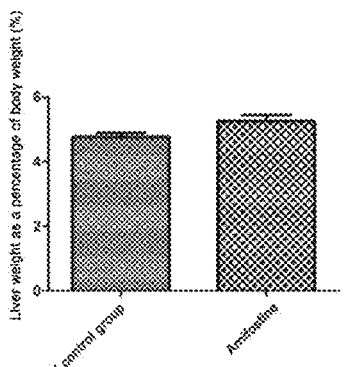
Figure 6C:
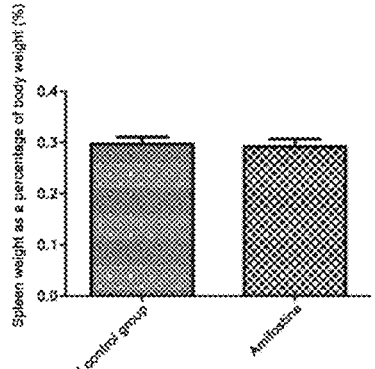
Figure 6D:
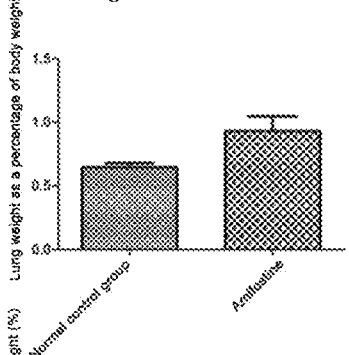
Figure 6E:
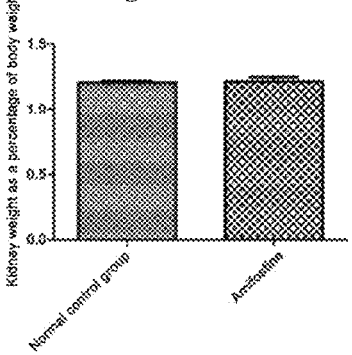
Figure 6F:
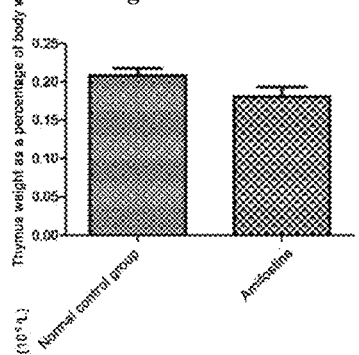
Figure 6G:
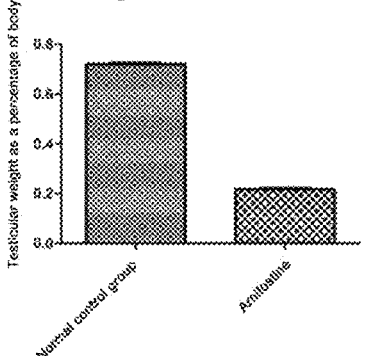
Figure 6H:
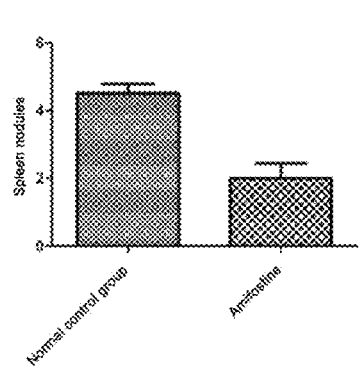
Figure 6I:
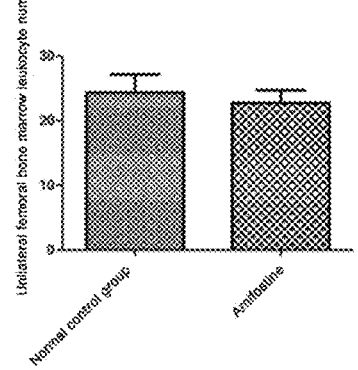
Figure 6J:
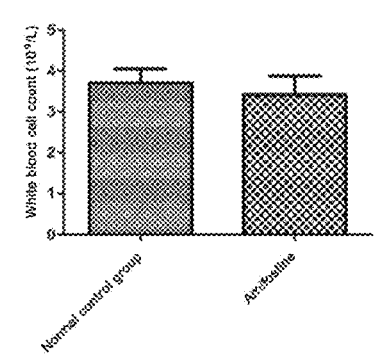

Results: At the same administration dose of the four compounds (200 mg/kg, one dose at 24 hours before irradiation and one dose at 30 minutes before irradiation), one-time whole body irradiation with 6.8Gy, 7.2Gy and 7.5Gy $^{137}$Cs gamma rays was performed, respectively, compared with the radiation and blank solvent group. The 30-day survival rate of mice was 100% when compound 1 was used in the cases of irradiations of 6.8Gy and 7.2Gy, respectively. The survival rate and body weight of mice in each group with different irradiation doses are shown in FIGS. 1, 3 and 5. The effects of normal control group and compound 1, compound 2, compound 3 and compound 4 on organs and leukocytes in mice 30 days after irradiation with 7.2Gy are shown in FIG. 4. The effects of normal control group and compound 1 on organs and leukocytes in mice 30 days after irradiation with 6.8Gy and 7.5Gy, respectively, are shown in FIGS. 2 and 6.

Example B

This example studies the effects of different compounds (i.e., Example 17, Example 2, Example 3, Example 18, Example 8, Example 1, Example 4) on the survival rate of mice without radiation dose, respectively.

Laboratory animals: C57 male mice, 8-10 weeks old, 20-22 g, were divided into 4 groups, 5 or 10 or 15 or 20 or 25 mice in each group. Irradiation conditions: 137Cs-γ rays, the dose rate was 0.7Gy/min, and the absorbed doses of mice were 6.8Gy, 7.2Gy and 7.5Gy, respectively, one-time whole body irradiation (if not specified, the irradiation rays were all 137Cs-γ rays)

Administration and Grouping:

In normal control group, intraperitoneal injection of normal saline was performed.

In irradiation control group, intraperitoneal injection of normal saline was performed 30 min before the irradiation.

In amifostine +6.8Gy (or 7.2Gy or 7.5Gy) group, intraperitoneal injection of amifostine (dissolved in normal saline, at a dosage of 200 mpk) was performed 30 min before the irradiation.

In Example 17 +6.8Gy (or 7.2Gy or 7.5Gy) group, Example 17 (dissolved in normal saline, at a dosage of 200 mpk) was intraperitoneally injected 30 min before the irradiation.

Observation index: The death and weight of the mice were recorded, and the survival rate was calculated on the 30$^{th}$ day. The surviving mice were sacrificed, dissected, and each organ index (the weight of each organ as a percentage of the body weight of the mouse) was calculated.

Experimental Results

| Group | 6.8Gy (Survival number/ Test number Survival rate) | 7.2Gy (Survival number/ Test number Survival rate) | 7.5Gy (Survival number/ Test number Survival rate) |
| --- | --- | --- | --- |
| Irradiation control group | 3/5 60% | 1/10 10% | 0/5 0% |
| Amifostine, 200 mpk, IP | 5/5 100% | 9/10 90% | 5/5 100% |
| Example 17, 200 mpk, IP | 5/5 100% | 9/10 90% | 0/5 0% |

The experimental operation was the same as the above, for the effects of different dosages on the survival rate of mice, except that the intraperitoneal injection of Example 17 was performed 90 min before the irradiation.

| Group | 7.5Gy (Survival number/Test number Survival rate) |
| --- | --- |
| 7.5Gy irradiation group | 0/5 0% |
| Amifostine, 200 mpk, IP | 4/5 80% |
| Example 17, 400 mpk, IP | 0/5 0% (intraperitoneal injection 90 min before irradiation) |
| Example 17, 800 mpk, IP | 0/5 0% intraperitoneal injection 90 min before irradiation |

The irradiation was invalid 90 minutes after administration.

Note: In the toxicity test of Example 17, muscle tremors and other toxic reactions were observed after intraperitoneal injection of 400 mpk and 800 mpk, followed by irradiation 90 min after administration.

Example 2, Example 3, Example 18, Example 8, Example 1 and Example 4 were tested at different absorbed doses using the above similar conditions or operations. The experimental results are as follows

| Group | 7.2Gy (Survival number/Test number Survival rate) |
|---|---|
| 7.2Gy irradiation group | 1/15 6.67% |
| Amifostine, 200 mpk, IP | 12/15 80% |
| Example 2, 200 mpk, IP | 10/15 66.67% |

| Group | 7.2Gy (Survival number/Test number Survival rate) |
|---|---|
| 7.2Gy irradiation group | 1/15 6.67% |
| Amifostine, 200 mpk, IP | 12/15 80% |
| Example 3, 200 mpk, IP | 10/15 66.67% |

| Group | 7.2Gy (Survival number/Test number Survival rate) |
|---|---|
| 7.2Gy irradiation group | 0/5 0% |
| Amifostine, 200 mpk, IP | 4/5 80% |
| Example 18, 200 mpk, IP | 4/5 80% |

| Group | 7.2Gy (Survival number/Test number Survival rate) |
|---|---|
| 7.2Gy irradiation group | 0/5 0% |
| Amifostine, 200 mpk, IP | 4/5 80% |
| Example 8, 200 mpk, IP | 1/5 20% |

| Group | 7.2Gy (Survival number/Test number Survival rate) |
|---|---|
| 7.2Gy irradiation group | 0/10 0% |
| Amifostine, 200 mpk, IP | 7/10 70% |
| Example 1, 200 mpk, IP | 6/10 60% |

| Group | 7.2Gy (Survival number/Test number Survival rate) |
|---|---|
| Irradiation control group | 4/25 16% |
| Amifostine, 200 mpk, IP | 20/25 80% |
| Example 4, 200 mpk, IP | 20/25 80% |

| Group | 7.5Gy (Survival number/Test number Survival rate) |
|---|---|
| 7.5Gy irradiation group | 0/10 0% |
| Amifostine, 200 mpk, IP | 1/10 10% |
| Example 4, 800 mpk, IP | 7/10 70% |

| Group | 7.5Gy (Survival number/Test number Survival rate) |
|---|---|
| 7.5Gy irradiation group | 2/10 20% |
| Amifostine, 365 mpk, IP | 10/10 100% |
| Example 4, 517 mpk, IP | 9/10 90% |

| Group | 10Gy (Survival number/Test number Survival rate) |
|---|---|
| 10Gy irradiation group | 0/20 0% |
| Amifostine, 517 mpk, IP | 15/20 75% |
| Example 4, 365 mpk, IP | 15/20 75% |

| Group | 12.5Gy (Survival number/Test number Survival rate) |
|---|---|
| 12.5Gy irradiation group | 0/10 0% |
| Amifostine, 517 mpk, IP | 5/10 50% |
| Example 4, 365 mpk, IP | 4/10 40% |

The above results indicated that the mice using compounds of Example 17, Example 2, Example 3, Example 18, Example 8, Example 1, and Example 4 had survival rates comparable to those using amifostine when the absorbed dose was 6.8Gy and 7.2Gy, among which the mice using the compound of Example 4 had a survival rate equivalent to those using amifostine when the absorbed dose was even higher, such as as high as 12.5Gy.

Example C: Acute Toxicity Test

Laboratory animals: C57 male mice, 8-10 weeks old, 20-22 g, 5 or 10 mice in each group.

Administration and grouping: Each group was intraperitoneally injected with one corresponding dose of amifostine.

Each group was intraperitoneally injected with one corresponding dose of Example 17 (IP).

The 30-day survival rate of mice in each group was recorded. The results are shown in the table

| Dosage (mpk) | 400 mpk (Survival number/Test number) | 600 mpk (Survival number/Test number) | 800 mpk (Survival number/Test number) | 900 mpk (Survival number/Test number) | 1000 mpk (Survival number/Test number) | 1100 mpk (Survival number/Test number) | 1200 mpk (Survival number/Test number) | 1600 mpk (Survival number/Test number) | 3200 mpk (Survival number/Test number) |
|---|---|---|---|---|---|---|---|---|---|
| Amifostine (IP) | 5/5 | 5/5 | 3/5 | NA | NA | NA | NA | 0/5 | NA |
| Example 17 (IP) | 5/5 | NA | 5/5 | NA | NA | NA | NA | 4/5 | NA |
| Example 4 (IP) | 10/10 | 5/5 | 10/10 | 10/10 | 6/6 10/10 | 8/10 | 6/10 | 3/10 | NA |

Acute toxicity tests indicated that the compound of the present invention, especially Example 4, was as safe as or even better than amifostine at high doses, in which the compound of Example 4 even had a 100% survival rate at a dose of 1000 mpk.

Example D

Protective effect of the compounds in the present invention on the hematopoietic system:
Laboratory animals: C57 male mice, 8-10 weeks old, 20-22 g, 5 mice in each group.
Administration and grouping: In normal control group, intraperitoneal injection of normal saline was performed, without irradiation.
In administration control group, intraperitoneal injection of Example 4 (800 mpk) was performed, without irradiation.
In irradiation control group, intraperitoneal injection of normal saline was performed 30 min before the irradiation at 4Gy.
In irradiation administration group, intraperitoneal injection of Example 4 (800 mpk) was performed 30 min before the irradiation at 4Gy.

The mice were sacrificed on the 15$^{th}$ day after the irradiation, followed by blood collection. Femoral bone marrow cells, spleen and thymus were weighed, and cells were extracted for detecting the peripheral white blood cell (WBC) count, peripheral red blood cell (RBC) count, peripheral hemoglobin (HGB) concentration, peripheral platelet (PLT) count, peripheral blood lymphocyte ratio (LY %), and peripheral blood neutrophil ratio (NE %). The results are shown in FIG. 7. The results showed that the number of WBC and RBC in the peripheral blood of mice was reduced by irradiation, and the number of these cells was increased by administration of Example 4 with significant difference; irradiation reduced LY % and increased NE % in peripheral blood of mice, and administration of Example 4 alleviated this abnormal differentiation with significant difference.

In addition, the number of leukocytes in bone marrow, ratio of hematopoietic stem cell (LSK) in bone marrow cells, ratio of hematopoietic progenitor cells (HPC) in bone marrow cells, ratio of CD34−LSK in bone marrow cells, and ratio of CD34+LSK in bone marrow cells were detected. The results are shown in FIG. 8. The results showed that the number of WBC, LSK % and HPC % in the bone marrow of mice was decreased by irradiation, and the number of these cells was increased by administration of Example 4 with significant difference; irradiation increased CD34−LSK % and decreased CD34+LSK % in the bone marrow of mice, and administration of Example 4 alleviated this abnormal differentiation with significant difference.

The effects of irradiation on LSK intracellular reactive oxygen species (ROS) level and HPC intracellular ROS level were also detected. The results are shown in FIG. 9. The results showed that irradiation increased the ROS levels in LSK and HPC cells in the bone marrow of mice, and administration of Example 4 reduced the ROS levels with significant difference.

Example E: Protective Effect of the Compounds of the Present Invention on the Intestinal Tract Example E1: Survival Rate of Radiation Intestinal Damage Laboratory animals: C57 male mice, 8-10 weeks old, 20-22 g, 5 mice in each group.

Administration and grouping: In irradiation control group, intraperitoneal injection of normal saline was performed 30 min before the irradiation, with local abdominal irradiation at 18Gy.
In amifostine group, intraperitoneal injection was performed 30 min before the local abdominal irradiation at 18Gy, wherein amifostine was dissolved in normal saline, 200 mpk.
In Example 4 group, intraperitoneal injection was performed 30 min before the local abdominal irradiation at 18Gy, wherein Example 4 was dissolved in normal saline, 800 mpk.

Figure 10:
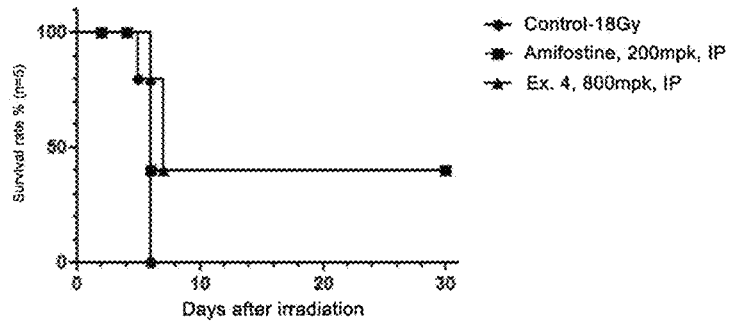
FIG. 10 shows the 30-day survival rate of Example 4 and amifostine in mice exposed to local abdominal radiation of 18Gy.

The 30-day survival rate of mice in each group was recorded. The results are shown in FIG. 10.

Example E2: HE Staining on the 5$^{th}$ Day after Local Intestinal Irradiation

Laboratory animals: C57 male mice, 8-10 weeks old, 20-22 g, 3 mice in each group
Administration and grouping: In normal control group, intraperitoneal injection of normal saline was performed, with false irradiation.
In irradiation control group, intraperitoneal injection of normal saline was performed 30 min before the irradiation, with local abdominal irradiation at 16Gy
In amifostine group, intraperitoneal injection was performed 30 min before the local abdominal irradiation at 16Gy, wherein amifostine was dissolved in normal saline, 365 mpk.
In Example 4 group, intraperitoneal injection was performed 30 min before the local abdominal irradiation at 16Gy, wherein Example 4 was dissolved in normal saline, 517 mpk.

Figure 11:
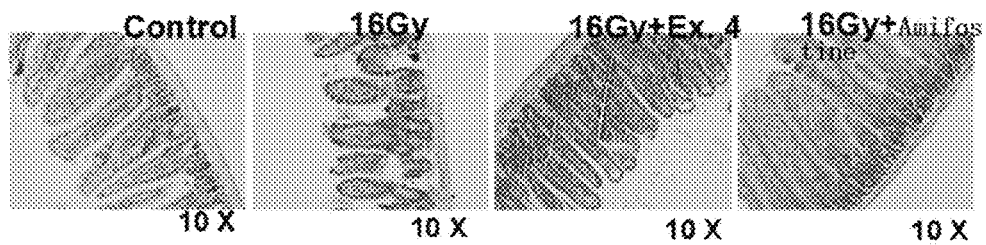
FIG. 11 shows the protective effect of Example 4 on the intestinal tract.

The mice were sacrificed on the 5$^{th}$ day after the irradiation, and the small intestine was taken and sectioned for HE staining. The results are shown in FIG. 11, and FIG. 11 shows that the normal unirradiated intestinal villi had clear and dense structures; the structure of villi in the small intestine changed after irradiation; the intestinal villi in the Example 4 irradiation group and the amifostine irradiation group showed slight changes compared with the irradiation group.

Example F: Effect of Example 4 on Radiation Pneumonia

Figure 12:
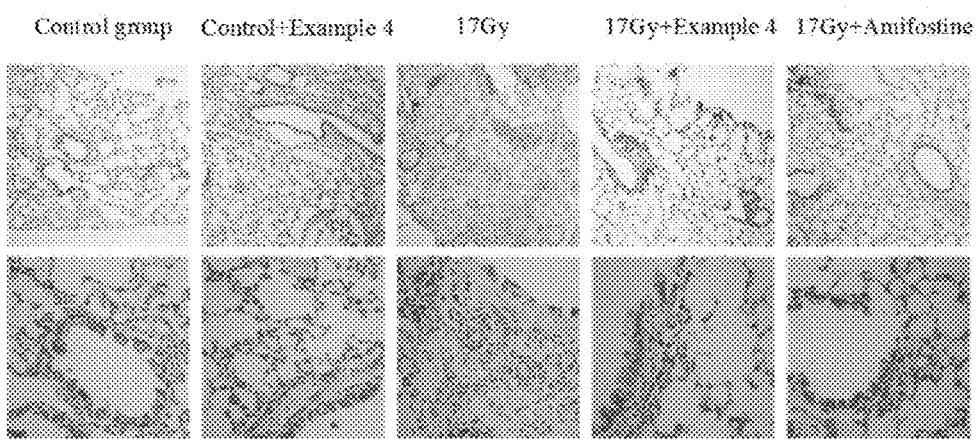
FIG. 12 shows the effect of Example 4 and amifostine on radiation pneumonia.

Laboratory animals: C57 male mice, 8-10 weeks old, 20-22 g, 3 mice in each group
Administration and grouping: Mice were intraperitoneally injected with normal saline, Example 4 (400 mpk), and amifostine (200 mpk) respectively 30 min before irradiation, and the right lungs were irradiated at 17Gy by X rays. The right lungs were taken on the 60$^{th}$ day for HE staining (n=3):

Two months after irradiation of the unilateral lung, the most important lung manifestation was radiation pneumonia. The lung tissues in mice of the control group showed obvious vacuolar structure, and no alveolar wall thickening was observed. The alveolar structure of mice in the 17Gy group was changed, which was manifested as a large area of inflammatory infiltration of the lung (the blue dots were inflammatory cells), and the alveoli were filled with inflammatory cells. Both amifostine and Example 4 could partially relieve inflammatory cell infiltration and reduce the incidence of radiation pneumonia. The results are shown in FIG. 12.

Example G: This Example Investigated the Effect of Stereoisomerism on Survival Rate In this Example, the effects of compounds such as Example 1

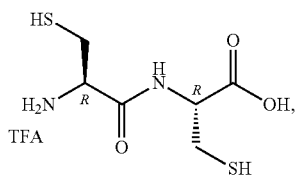

Example 2

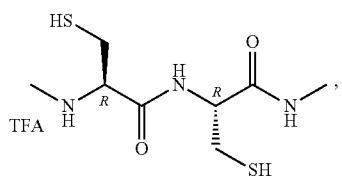

Example 3

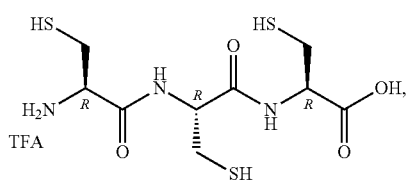

Example 4

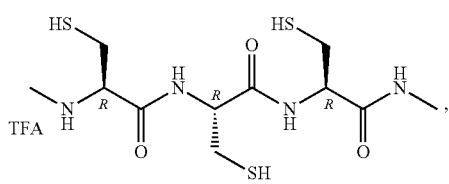

Example 19

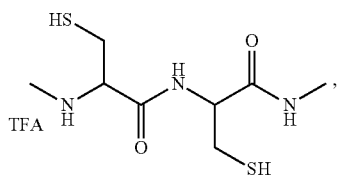

Example 20

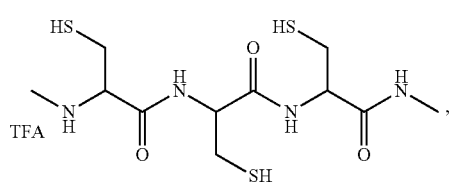

as well as L-cysteine

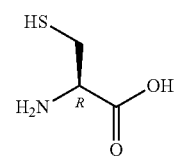

and D-cysteine

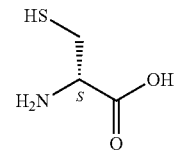

on the survival rate of mice under irradiation were further studied.

Laboratory animals: C57 male mice, 19-21 g, purchased from Beijing HFK Bioscience Co. Ltd., license number SCXK (Beijing), 9 mice in each group.

Administration and grouping: In 7.5Gy irradiation control group, intraperitoneal injection of normal saline was performed 30 min before the irradiation.

The other administration groups were treated by intraperitoneal injection of normal saline solutions of the corresponding drugs, 200 mg/kg, 30 min before the irradiation.

Figure 13:
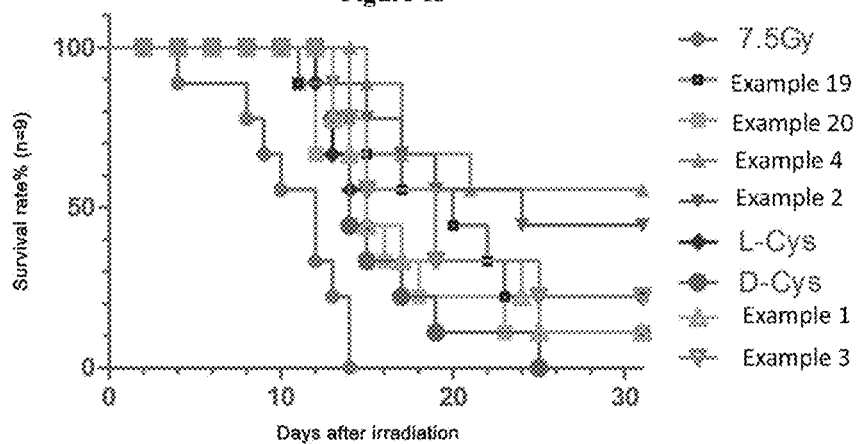
FIG. 13 shows the effect of stereoisomerism of the compound on the survival rate.

The experimental results are shown in the table below and FIG. 13:

|  | 7.5Gy (Survival number/Test number) | 7.5Gy (Survival number/ Test number) | 7.5Gy (Survival number/ Test number) |
| --- | --- | --- | --- |
| Irradiation control group | 0/9 (9 deaths) | | |
| L-Cys | 1/9 (8 deaths) | | |
| D-Cys | 0/9 (9 deaths) | | |

| | 7.5Gy (Survival number/Test number) | | 7.5Gy (Survival number/ Test number) | | 7.5Gy (Survival number/ Test number) |
|---|---|---|---|---|---|
| Example 4 | 5/9 (4 deaths) | Example 20 | 1/9 (8 deaths) | Example 3 | 2/9 (7 deaths) |
| Example 2 | 4/9 (5 deaths) | Example 19 | 2/9 (7 deaths) | Example 1 | 1/9 (8 deaths) |

The survival rate in the case of Example 4 was approximately 56%, significantly higher than that of cysteine trimer of Example 3 (approximately 22%) and the racemate of Example 20; the survival rate in the case of Example 2 was approximately 44%, significantly higher than that of cysteine dimer of Example 1 (approximately 11%) and the racemate of Example 19. It indicates that N-methylation of cysteine polymer can significantly improve the survival rate of irradiated mice and further enhance the irradiation protection ability of the compounds.

At this point, a person skilled in the art should realize that although the present invention has illustrated and described several exemplary embodiments of the present invention in detail, many other variations or modifications conforming to the principle of the present invention can be directly determined or deduced according to the disclosed contents of the present invention without departing from the spirit and scope of the present invention. Therefore, the scope of the present invention shall be understood and deemed to cover all such other variations or modifications.

We claim:

1. A compound of formula (I):

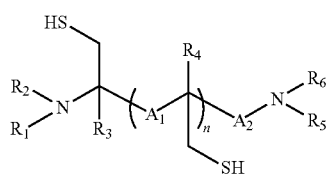

(I)

wherein $A_1$ is selected from: —C(O)NR$^8$—, —S(O)$_2$—NR$^8$—, —S(O)NR$^8$—, and —R$^7$—NR$^8$—;

$A_2$ is selected from: carbonyl, sulfonyl, sulfinyl, substituted or unsubstituted $C_{1-6}$ alkyl;

$R^1$ is selected from: hydrogen, substituted or unsubstituted $C_1$-$C_5$ alkyl or substituted or unsubstituted heteroalkyl;

$R^2$ is selected from substituted or unsubstituted $C_1$-$C_5$ alkyl or substituted or unsubstituted heteroalkyl;

$R^5$ is selected from hydrogen, substituted or unsubstituted $C_1$-$C_5$ alkyl or substituted or unsubstituted heteroalkyl;

$R^6$ is selected from substituted or unsubstituted $C_1$-$C_5$ alkyl or substituted or unsubstituted heteroalkyl;

n is an integer from 1 to 20,000;

$R^3$ and $R^4$ are independently selected from: hydrogen, X, substituted or unsubstituted $C_{1-6}$ alkyl;

X is selected from: F, Cl, Br and I; and $R^7$ is selected from: substituted or unsubstituted $C_1$-$C_6$ alkyl; $R^8$ is selected from: hydrogen, substituted or unsubstituted $C_1$-$C_6$ alkyl;

or a stereoisomer thereof or a pharmaceutically acceptable salt, a prodrug or a solvate thereof.

2. The compound of claim 1, wherein $A_2$ is selected from: carbonyl, sulfonyl, sulfinyl, substituted or unsubstituted $C_{1-3}$ alkyl;

$R^1$ is selected from: hydrogen, $C_{1-3}$ alkyl, and hydroxy or amino-substituted $C_1$-$C_3$ alkyl or substituted or unsubstituted heteroalkyl;

$R^2$ is selected from $C_1$-$C_3$ alkyl, hydroxy or amino-substituted $C_1$-$C_3$ alkyl or substituted or unsubstituted heteroalkyl;

$R^5$ is selected from hydrogen, $C_1$-$C_3$ alkyl, hydroxy or amino-substituted $C_1$-$C_3$ alkyl or substituted or unsubstituted heteroalkyl;

$R^6$ is selected from unsubstituted $C_1$-$C_3$ alkyl, hydroxy or amino-substituted $C_1$-$C_3$ alkyl or substituted or unsubstituted heteroalkyl;

n is an integer from 1 to 2,000;

$R^3$ and $R^4$ are independently selected from: hydrogen, X, substituted or unsubstituted $C_{1-3}$ alkyl;

X is selected from: F and Cl;

$R^7$ is selected from: substituted or unsubstituted $C_1$-$C_3$ alkyl;

$R^8$ is selected from: hydrogen, substituted or unsubstituted $C_1$-$C_3$ alkyl; and wherein the chiral carbon directly attached to $R^3$ and $R^4$ is in R configuration or S configuration.

3. The compound of claim 1, wherein $A_2$ is selected from: carbonyl, sulfonyl, sulfinyl, methylene;

$R^1$ is selected from: hydrogen, methyl, and ethyl;

$R^2$ is selected from: methyl, and ethyl;

$R^5$ is selected from: hydrogen, methyl, and ethyl;

$R^6$ is selected from: methyl, and ethyl;

n is an integer from 1 to 200;

$R^3$ and $R^4$ are independently selected from: hydrogen, X, methyl;

X is F;

$R^7$ is methylene; and $R^8$ is selected from: hydrogen, methyl, and ethyl.

4. The compound of claim 1, wherein the compound has the following general formula:

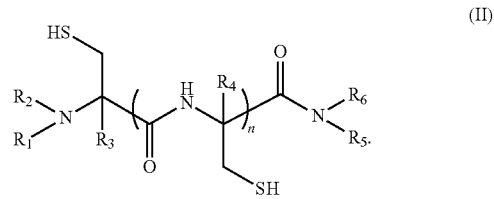

(II)

5. The compound of claim 1, wherein the compound has the following general formulas:
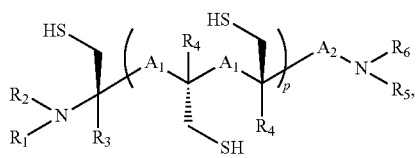
(III)
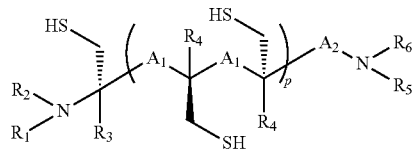
(IV)
wherein p is an integer from 1 to 10,000.
6. The compound of claim 1, wherein the compound is selected from:
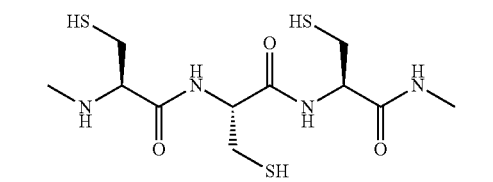
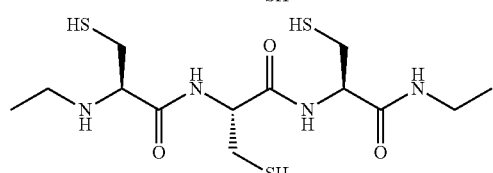
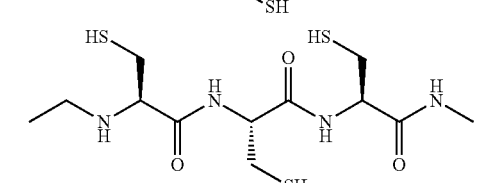
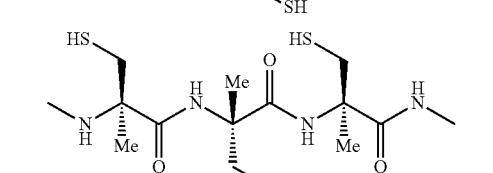
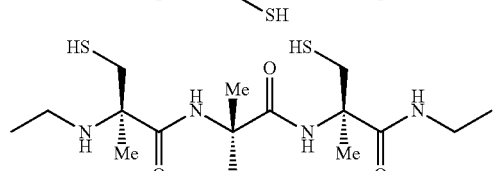
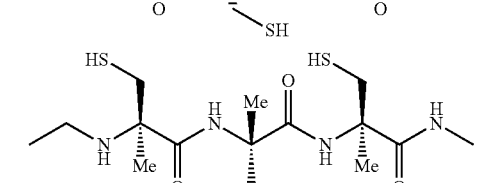
-continued
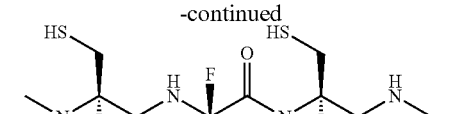
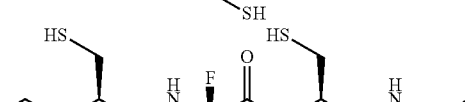
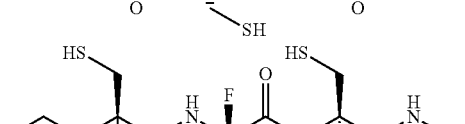
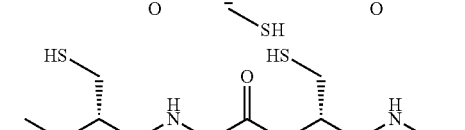
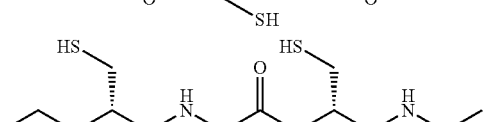
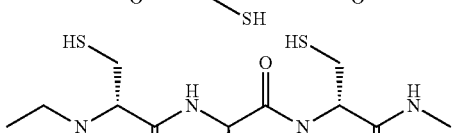
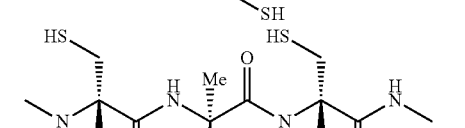
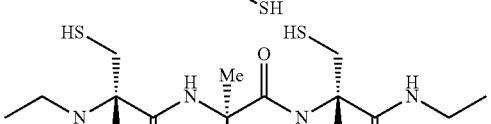
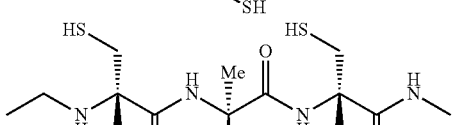
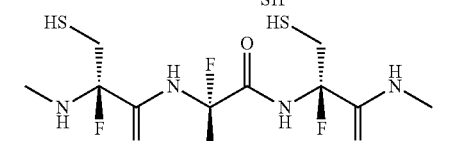

-continued
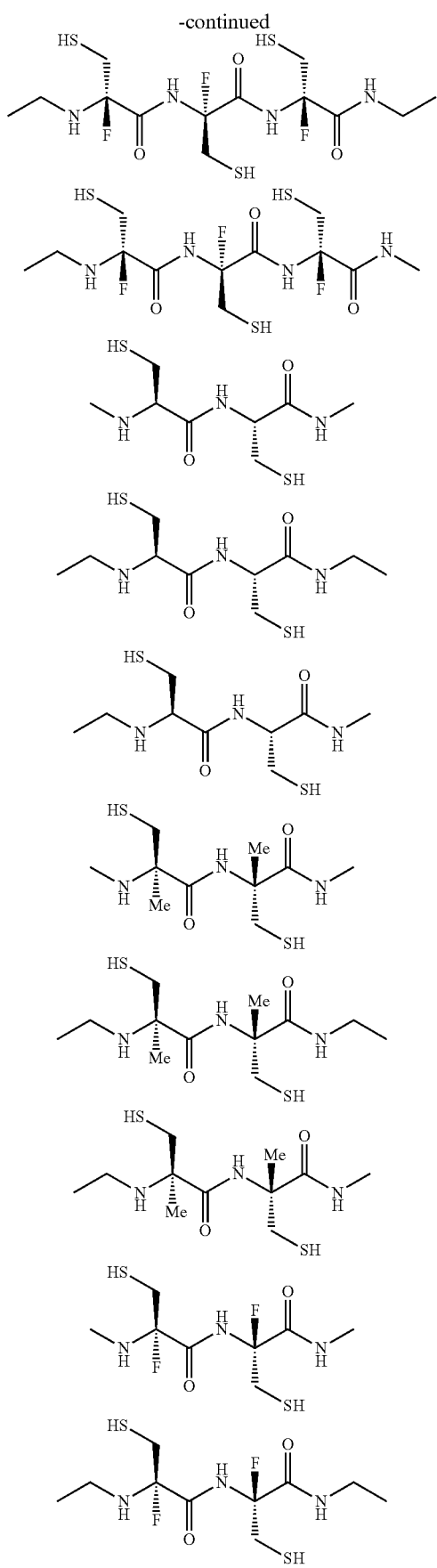
-continued
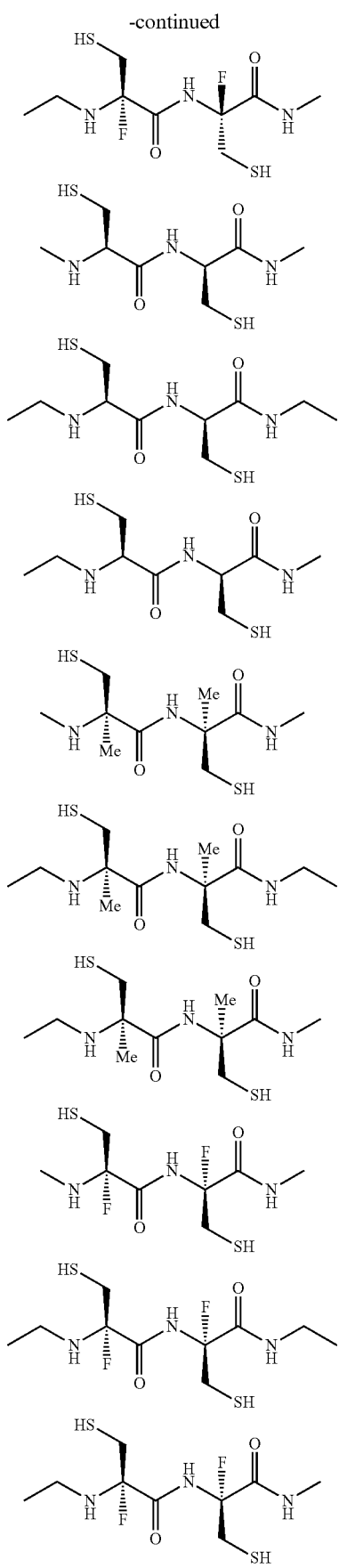

95
-continued
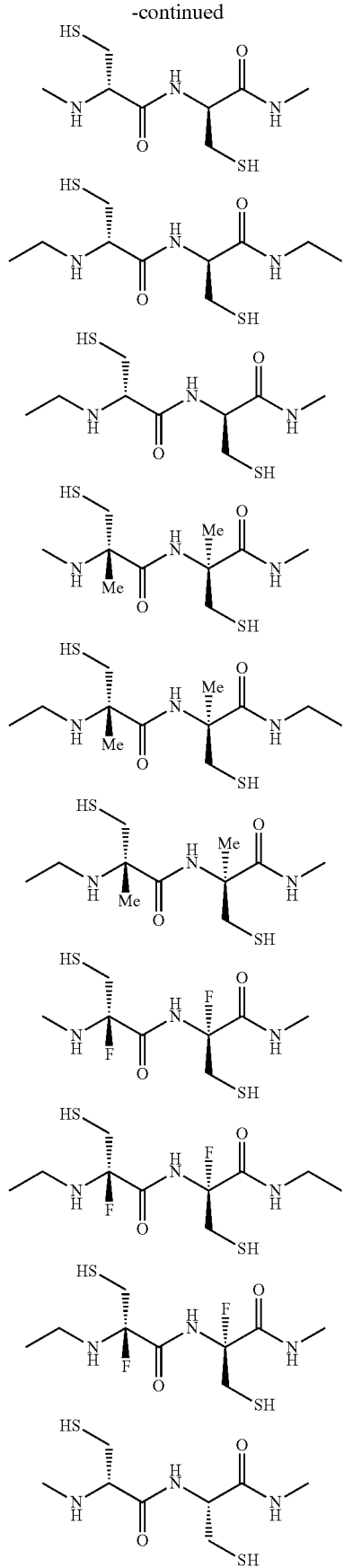
96
-continued
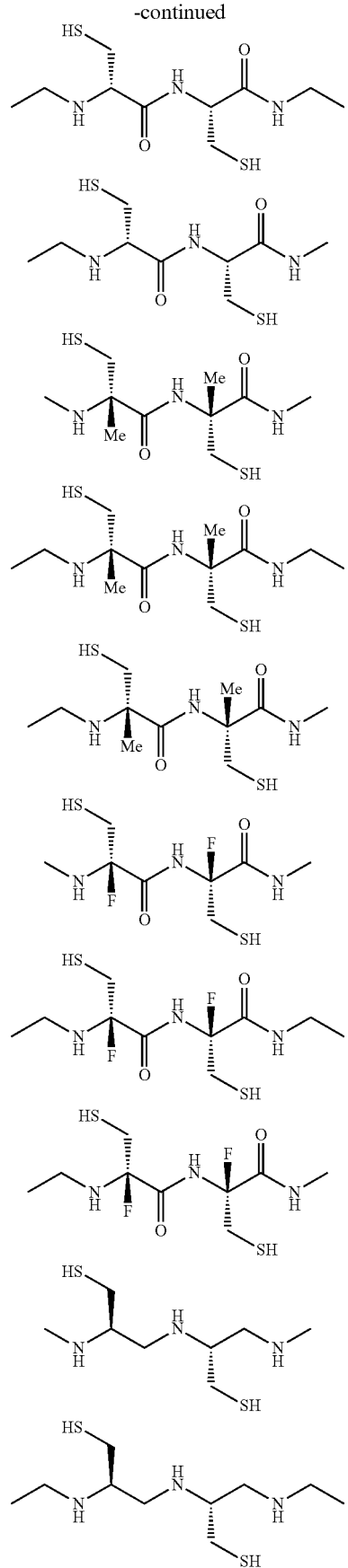

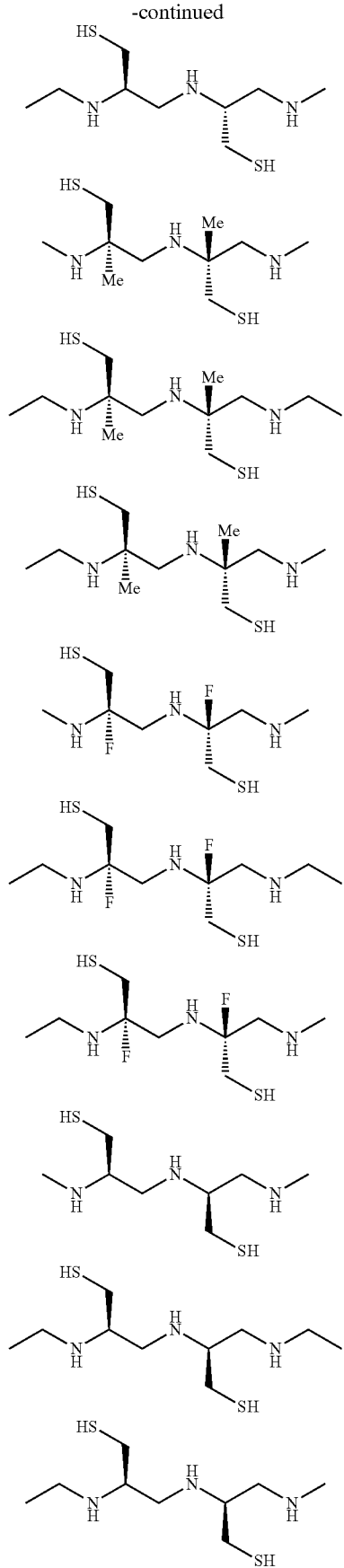
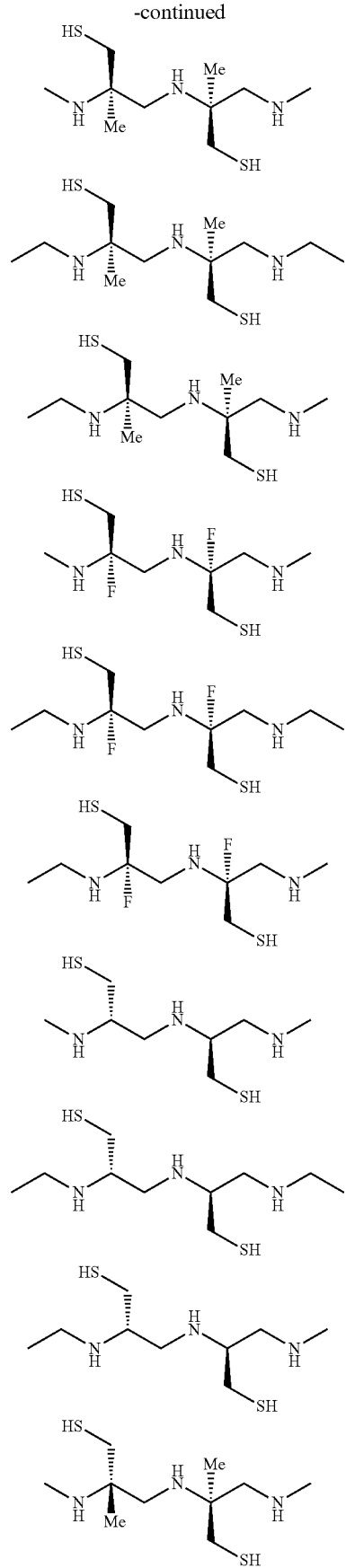

99
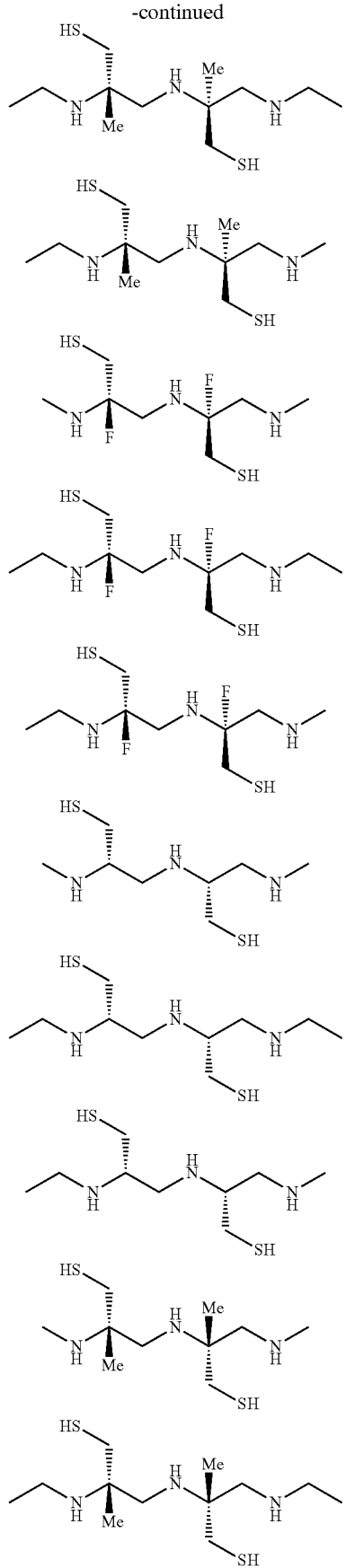
100
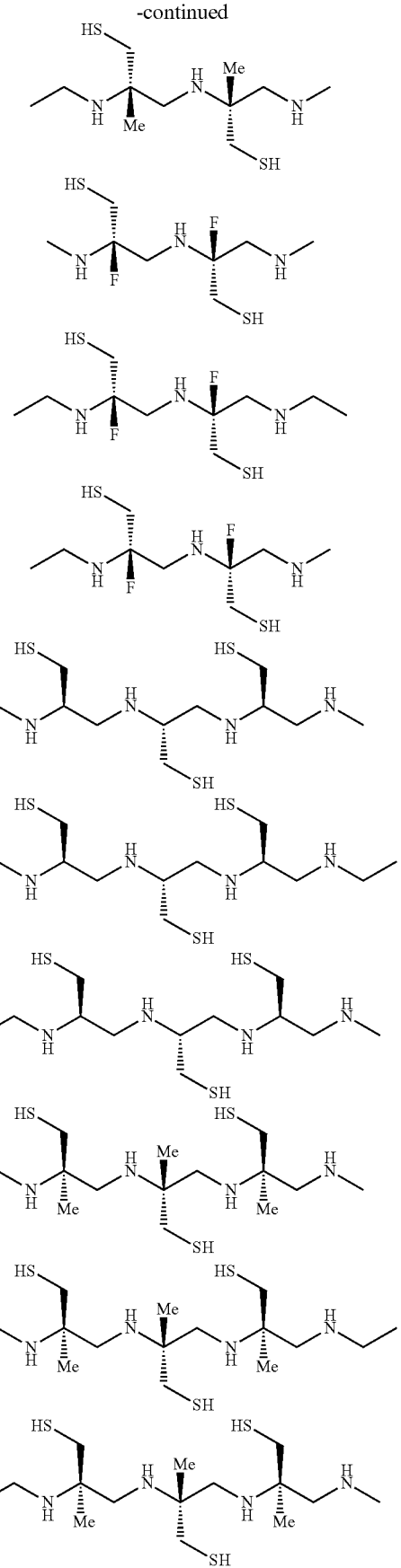

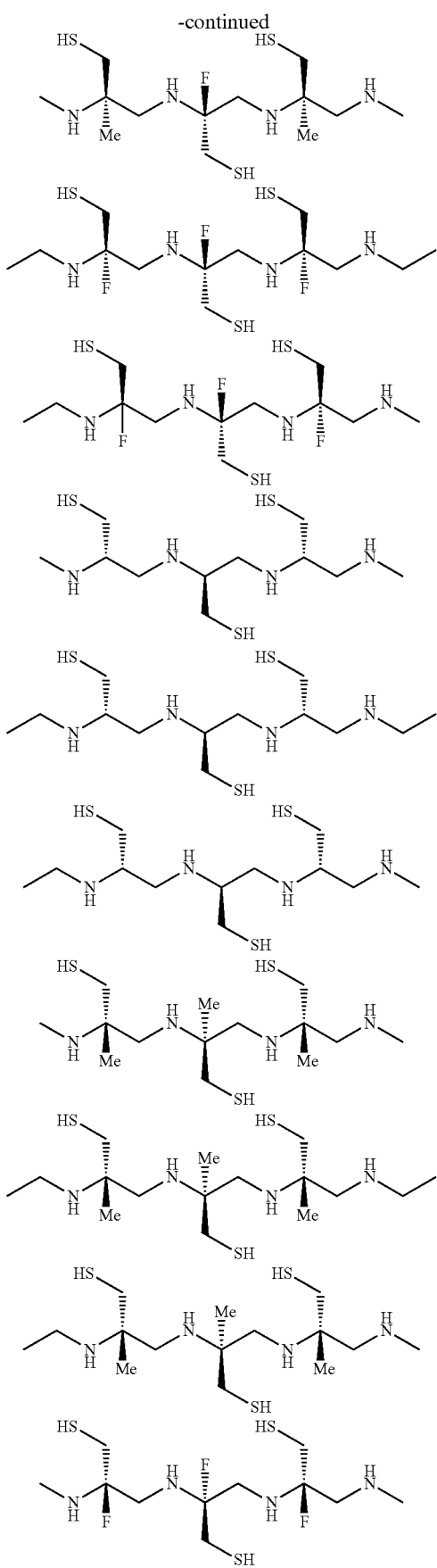

-continued

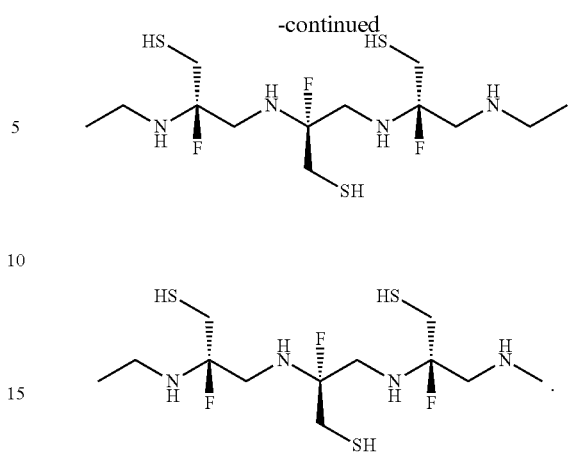

7. A pharmaceutical composition comprising a compound of formula (I):

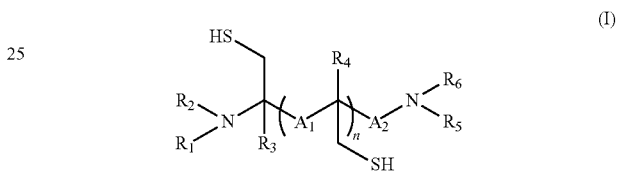

wherein $A_1$ is selected from: —C(O)NR$^8$—, —S(O)$_2$—NR$^8$—, —S(O)NR$^8$—, and —R$^7$—NR$^8$—;

$A_2$ is selected from: carbonyl, sulfonyl, sulfinyl, substituted or unsubstituted $C_{1-6}$ alkyl;

$R^1$ is selected from: hydrogen, substituted or unsubstituted $C_1$-$C_5$ alkyl or substituted or unsubstituted heteroalkyl;

$R^2$ is selected from substituted or unsubstituted $C_1$-$C_5$ alkyl or substituted or unsubstituted heteroalkyl;

$R^5$ is selected from hydrogen, substituted or unsubstituted $C_1$-$C_5$ alkyl or substituted or unsubstituted heteroalkyl;

$R^6$ is selected from substituted or unsubstituted $C_1$-$C_5$ alkyl or substituted or unsubstituted heteroalkyl;

n is an integer from 1 to 20,000;

$R^3$ and $R^4$ are independently selected from: hydrogen, X, substituted or unsubstituted $C_{1-6}$ alkyl;

X is selected from: F, Cl, Br and I; and $R^7$ is selected from: substituted or unsubstituted $C_1$-$C_6$ alkyl; $R^8$ is selected from: hydrogen, substituted or unsubstituted $C_1$-$C_6$ alkyl;

or a stereoisomer thereof or a pharmaceutically acceptable salt, a prodrug or a solvate thereof, and one or more pharmaceutically acceptable vehicles, carriers, adjuvants, auxiliaries or diluents.

8. The pharmaceutical composition of claim 7, wherein the dosage form of the pharmaceutical composition is selected from injections, emulsions, microemulsions, sub-microemulsions, nanoparticles, tablets, capsules, pills, inhalants, lozenges, gels, powders, suppositories, suspensions, creams, jellies, and sprays.

9. A method for the treatment and/or prevention of radiation damage or chemotherapy damage or a tumor, comprising:
administrating to a subject in need thereof a compound of formula (I):

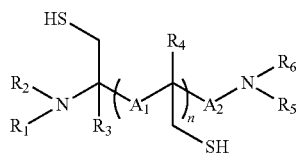

wherein
$A_1$ is selected from: —C(O)NR$^8$—, —S(O)$_2$—NR$^8$—, —S(O)NR$^8$—, and —R$^7$—NR$^8$—;
$A_2$ is selected from: carbonyl, sulfonyl, sulfinyl, substituted or unsubstituted $C_{1-6}$ alkyl;
$R^1$ is selected from: hydrogen, substituted or unsubstituted $C_1$-$C_5$ alkyl or substituted or unsubstituted heteroalkyl;
$R^2$ is selected from substituted or unsubstituted $C_1$-$C_5$ alkyl or substituted or unsubstituted heteroalkyl;
$R^5$ is selected from hydrogen, substituted or unsubstituted $C_1$-$C_5$ alkyl or substituted or unsubstituted heteroalkyl;
$R^6$ is selected from substituted or unsubstituted $C_1$-$C_5$ alkyl or substituted or unsubstituted heteroalkyl;
n is an integer from 1 to 20,000;
$R^3$ and $R^4$ are independently selected from: hydrogen, X, substituted or unsubstituted $C_{1-6}$ alkyl;
X is selected from: F, Cl, Br and I; and
$R^7$ is selected from: substituted or unsubstituted $C_1$-$C_6$ alkyl; $R^8$ is selected from: hydrogen, substituted or unsubstituted $C_1$-$C_6$ alkyl;
or a stereoisomer thereof or a pharmaceutically acceptable salt, a prodrug or a solvate thereof.

10. The method of claim 9, wherein the radiation comprises ionizing radiation, non-ionizing radiation or a combination of various types of radiation;
the ionizing radiation comprises alpha rays, beta rays, gamma rays, X rays, and neutron radiation;
the radiation damage comprises direct damage and indirect damage caused by radiation;
the chemotherapeutic drugs refer to the anti-tumor drugs acting on DNA, RNA and tubulin; and
the compound of formula (I) is used alone or in combination with a radioprotective agent to prepare drugs and/or cosmetics for the treatment and/or prevention of radiation damage and chemotherapy damage.

11. The method of claim 9 wherein the radiation damage is sunburn damage.

* * * * *